(12) United States Patent
Vajdy et al.

(10) Patent No.: US 10,561,720 B2
(45) Date of Patent: *Feb. 18, 2020

(54) PHARMACEUTICAL COMPOSITIONS, COMPRISING A COMBINATION OF SELECT CARRIERS, VITAMINS, TANNINS AND FLAVONOIDS AS ANTIGEN-SPECIFIC IMMUNO-MODULATORS

(75) Inventors: Michael Vajdy, Orinda, CA (US); Shore Padrah, Orinda, CA (US)

(73) Assignee: EpitoGenesis, Inc., Walnut Creek, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/531,433

(22) Filed: Jun. 22, 2012

(65) Prior Publication Data

US 2013/0028961 A1    Jan. 31, 2013

Related U.S. Application Data

(60) Provisional application No. 61/500,993, filed on Jun. 24, 2011, provisional application No. 61/513,840, filed on Aug. 1, 2011.

(51) Int. Cl.
*A61K 39/12* (2006.01)
*A61K 39/39* (2006.01)
*A61K 39/00* (2006.01)

(52) U.S. Cl.
CPC .............. *A61K 39/12* (2013.01); *A61K 39/39* (2013.01); *A61K 2039/55505* (2013.01);
(Continued)

(58) Field of Classification Search
None
See application file for complete search history.

(56) References Cited

U.S. PATENT DOCUMENTS 4,698,221 A * 10/1987 Straub .................. 424/245.1
5,135,855 A    8/1992 Moss et al.
(Continued)

FOREIGN PATENT DOCUMENTS

DE    19935763 A1 *  2/2001  ............... A61K 8/06
EP    0378881 A1    12/1989
(Continued)

OTHER PUBLICATIONS

Deryabin P et al, Effects of a nutrient mixture on infectious properties of the highly pathogenic strain of avian influenza virus A/H5N1, 2008, BioFactors, 33, 85-97, IOS Press.*

(Continued)

*Primary Examiner

(52) U.S. Cl.
CPC . *A61K 2039/55511* (2013.01); *A61K 2039/57* (2013.01); *A61K 2039/572* (2013.01); *A61K 2039/575* (2013.01); *A61K 2039/577* (2013.01); *C12N 2740/16034* (2013.01); *C12N 2760/16134* (2013.01)

(56) References Cited

U.S. PATENT DOCUMENTS

| | | | |
|---|---|---|---|
| 5,139,941 | A | 8/1992 | Muzyczka et al. |
| 5,149,650 | A * | 9/1992 | Wertz .................. A61K 39/155 435/243 |
| 5,173,414 | A | 12/1992 | Lebkowski et al. |
| 5,219,740 | A | 6/1993 | Miller et al. |
| 5,229,130 | A | 7/1993 | Sharma et al. |
| 5,399,346 | A | 3/1995 | Anderson et al. |
| 5,484,596 | A | 1/1996 | Hanna, Jr. et al. |
| 5,580,859 | A | 12/1996 | Felgner et al. |
| 5,589,466 | A | 12/1996 | Felgner et al. |
| 5,614,413 | A | 3/1997 | Morrow |
| 5,676,950 | A | 10/1997 | Small, Jr. et al. |
| 6,063,384 | A | 5/2000 | Morrow et al. |
| 6,329,201 | B1 | 12/2001 | Polo et al. |
| 6,342,372 | B1 | 1/2002 | Dubensky, Jr. et al. |
| 6,746,677 | B2 * | 6/2004 | Cobb .................. A61K 9/0019 424/184.1 |
| 7,544,816 | B2 | 6/2009 | Chan et al. |
| 7,601,754 | B2 | 10/2009 | Caldwell et al. |
| 2002/0071846 | A1 | 6/2002 | Deckers et al. |
| 2002/0150593 | A1 * | 10/2002 | Hymas ................ A61K 39/0241 424/201.1 |
| 2003/0147898 | A1 | 8/2003 | Van Nest et al. |
| 2004/0076614 | A1 | 4/2004 | Schur |
| 2006/0088485 | A1 * | 4/2006 | Ishida .................. A61K 8/4973 424/62 |
| 2006/0217443 | A1 * | 9/2006 | Huang et al. .................. 514/568 |
| 2006/0233816 | A1 | 10/2006 | Schryvers et al. |
| 2007/0082073 | A1 | 4/2007 | Van Olphen et al. |
| 2008/0254188 | A1 | 10/2008 | Borowy-Borowski et al. |
| 2008/0299200 | A1 * | 12/2008 | Leser .................. B01F 17/0028 424/484 |
| 2009/0324584 | A1 | 12/2009 | Hoerr et al. |
| 2010/0172941 | A1 | 7/2010 | Vajdy et al. |

FOREIGN PATENT DOCUMENTS

| | | | |
|---|---|---|---|
| EP | 0372501 | A2 | 6/1990 |
| EP | 0427347 | A1 | 11/1990 |
| EP | 0471177 | A2 | 7/1991 |
| JP | 2004-527615 | A | 9/2004 |
| JP | 2006-206539 | A | 8/2006 |
| JP | 2007-530607 | A | 11/2007 |
| JP | 2009-165450 | A | 7/2009 |
| JP | 2011-072311 | A | 4/2011 |
| JP | 2011-105652 | A | 6/2011 |
| WO | 89/03429 | A1 | 4/1989 |
| WO | 91/12882 | A1 | 9/1991 |
| WO | 92/01070 | A1 | 1/1992 |
| WO | 92/03545 | A1 | 3/1992 |
| WO | 92/19265 | A1 | 11/1992 |
| WO | 93/03769 | A1 | 3/1993 |
| WO | 93/13202 | A1 | 7/1993 |
| WO | 93/17712 | A2 | 9/1993 |
| WO | 94/26911 | A1 | 11/1994 |
| WO | 95/17211 | A1 | 6/1995 |
| WO | 96/29412 | A1 | 9/1996 |
| WO | 98/18928 | A1 | 5/1998 |
| WO | 98/58668 | A2 | 12/1998 |
| WO | 99/24578 | A3 | 5/1999 |
| WO | 99/27105 | A3 | 6/1999 |
| WO | 99/28475 | A2 | 6/1999 |
| WO | 99/36544 | A2 | 7/1999 |
| WO | 99/57280 | A3 | 11/1999 |
| WO | 00/22430 | A3 | 4/2000 |
| WO | 00/27994 | A2 | 5/2000 |
| WO | 00/37494 | A2 | 6/2000 |
| WO | 00/56360 | A2 | 9/2000 |
| WO | 00/61761 | A2 | 10/2000 |
| WO | 01/22993 | A2 | 4/2001 |
| WO | 01/52885 | A1 | 7/2001 |
| WO | 01/92552 | A2 | 12/2001 |
| WO | 02/02606 | A2 | 1/2002 |
| WO | WO-02-02606 | * | 1/2002 |
| WO | WO-2005-121378 | * | 12/2005 |
| WO | WO-2009-131995 | * | 10/2009 |
| WO | WO 2010/078556 | A1 | 7/2010 |

OTHER PUBLICATIONS

Heurtault B, Liposomes as delivery systems for nasal vaccination: strategies and outcomes, 2010, Expert Opinion in Drug Delivery, 7 (7), 829-844.*

Choo et al., "Recovered Oil from Palm-Pressed Fiber: A Good Source of Natural Carotenoids, Vitamin E, and Sterols," JAOCS, 1996, vol. 73, No. 5, pp. 599-602 (Year: 1996).*

Gale et al., "An ab Initio Study of the Structure and Properties of Aluminum Hydroxide: Gibbsite and Bayerite," J. Phys. Chem., 2001, vol. 105, pp. 10236-10242 (Year: 2001).*

Kalinova et al., "Distribution of Vitamin E, Squalene, Epicatechin, and Rutin in Common Buckwheat Plants (Fagopyrum esculentum Moench)," J. Agric. Food Chem., 2006, vol. 54, pp. 5330-5335 (Year: 2006).*

Lin et al., "Antibacterial Mechanism of Allyl Isothiocyanate," J. of Food Protection, 2000, vol. 63, No. 6, pp. 727-734 (Year: 2000).*

Mustakas et al., "Enzymatic Process for Mustard Seed to Produce Oil, Meal, and Allyl Isothiocyanate," Biotechnology and Bioengineering, 1963, vol. V, pp. 27-39 (Year: 1963).*

Teres et al., "Oleic acid content is responsible for the reduction in blood pressure induced by olive oil," PNAS, 2008, vol. 105, No. 37, pp. 13811-13816 (Year: 2008).*

Shirai, et al. (2000). "Comparison of outer membrane protein genes omp and pmp in the whole genome sequences of Chlamydia pneumoniae isolates from Japan and the United States." J. Infect. Dis. 181(Suppl3):S524-S527.

Sood, N. N., et al. (1985). "Epidemic dropsy following transcutaneous absorption of Argemone mexicana oil." Transactions of the Royal Society of Tropical Medicine and Hygiene 79(4): 510-512.

Studier, F. W., et al. (1986). "Use of bacteriophage T7 RNA polymerase to direct selective high-level expression of cloned genes." Journal of Molecular Biology 189(1): 113-130.

Sutter, R. W., et al. (2000). "Poliovirus vaccines: progress toward global poliomyelitis eradication and changing routine immunization recommendations in the United States." Pediatric clinics of North America 47(2): 287-308 (Abstract).

Tengerdy RP, et al. (1983) Vitamin E-enhanced humoral antibody response to Clostridium perfringens type D in sheep. British Veterinary Journal139, 147-152.

Tengerdy, R. P. (1990). "The role of vitamin E in immune response and disease resistance." Annals of the New York Academy of Sciences 587: 24-33.

Tengerdy, R. P., et al. (1991). "Vitamin E adjuvant formulations in mice." Vaccine 9(3): 204-206.

Tengerdy, R. P., et al. (1991). "Serological responses of rams to a *Brucella ovis*—vitamin E adjuvant vaccine." Vaccine 9(4): 273-276.

Tettelin, H., et al. (2000). "Complete Genome Sequence of Neisseria meningitidis Serogroup B Strain MC58." Science 287(5459): 1809.

Tomasetti, et al. (2007). "Vitamin E Analogues and Immune Response in Cancer Treatment." Vitamins & Hormones 76: 463-491.

Van Der Stede, et al. (2001). "Enhanced induction of the IgA response in pigs by calcitriol after intramuscular immunization." Vaccine 19(15-16): 1870-1878.

Wagner, E., et al. (1992). "Coupling of adenovirus to transferrin-polylysine/DNA complexes greatly enhances receptor-mediated gene delivery and expression of transfected genes." Proceedings of the National Academy of Sciences of the United States of America 89(13): 6099-6103.

(56) References Cited

OTHER PUBLICATIONS

Wang, J., et al. (2002). "Effects of Anthocyanins and Other Phenolic Compounds on the Production of Tumor Necrosis Factor a in LPS/IFN-y-Activated RAW 264.7 Macrophages." Journal of Agricultural and Food Chemistry 50 (15): 4183-4189.
Watson, W. (2000). "Pneumococcal conjugate vaccines." The Pediatric Infectious Disease Journal 19(4): 331-332.
Wiedermann, U., et al. (1993). "Impaired mucosal antibody response to cholera toxin in vitamin A-deficient rats immunized with oral cholera vaccine." Infect. Immun. 61(9): 3952-3957.
Yamamoto, Y., et al. (2004). "Protective effects of green tea catechins on alveolar macrophages against bacterial infections." Biofactors 21 (1-4): 119-121.
Yu, S., et al. (2005). "All-trans retinoic acid biases immune response induced by DNA vaccine in a Th2 direction." Vaccine 23(44): 5160-5167.
Zhou, S., et al. (1994). "Adeno-associated virus 2-mediated high efficiency gene transfer into immature and mature subsets of hematopoietic progenitor cells in human umbilical cord blood." J. Exp. Med. 179(6): 1867-1875.
Zimmerman, R. K. (1999). "Poliovirus vaccine options." Am. Fam. Physician 59:113-118, 125-126.
Kuroda, M., et al. (2001). "Whole genome sequencing of meticillin-resistant *Staphylococcus aureus*." Lancet 357 (9264): 1225.
http://skipthepie.org/fats-and-oils/oil-mustard/compared-to/usda-commodity-food-oil-vegetable-soybean-refined/ (Retrieved on Jun. 17, 2011.).
Cejpek, et al. (1998) "Effect of Sulphite Treatment on Allyllsothiocyanate in Mustard Paste" Food Chemistry 62 1 (1 ):53-57; Abstract; [online], [retrieved on Mar. 16, 2010]. Retrieved from the Interne!: <URL:http://cal.inisl.frl? DaModele=afficheN&cpsidt=2261722>ab.
Kurata, T., et al. (1977). "Suppressed tumor growth and metastasis by vitamin A + BCG in Lewis lung tumor bearing mice." Oncology 34(5): 212-215.
McMurray, D.N., et al. (1990). "Micronutrient status and immune function in tuberculosis." Annals of the New York Academy of Sciences 587, 59-69.
International Search Report and Written Opinion issued in International Application No. PCT/US2012/043890 dated Sep. 13, 2012—17 pages.
Afzal, M., et al. (1984). "Protection of rams against epididymitis by a –vitamin E adjuvant vaccine." Veterinary Immunology and Immunopathology 7(3-4): 293-304.
Ala' Aldeen, D., et al (2001) "Unveiling of Genetic Basis of Resistance of *S aureus* to Antibiotics" The Lancet 357 (9264):1218-1219.
Athanassiades, T. (1981) "Adjuvant effect of vitamin A palmitate and analogs on cell-mediated immunity." Journal of the National Cancer Institute. 67(5): 1153-6.
Ballow, M., et al. (1996). "Modulation of B-Cell Immunoglobulin Synthesis by Retinoic Acid." Clinical Immunology and Immunopathology 80(3): S73-S81.
Banic, S. (1982). "Immunostimulation by vitamin c." Int J Vitam Nutr Res Suppl. 23:49-52.
Banvolgyi, A., G. Pozsgai, et al. (2004). "Mustard oil induces a transient receptor potential vanilloid 1 receptor-independent neurogenic inflammation and a non-neurogenic cellular inflammatory component in mice." Neuroscience 125(2): 449-459.
Barr, E., et al. (1994). "Efficient catheter-mediated gene transfer into the heart using replication defective adenovirus." Gene Therapy 1(1): 51-58.
Barrnet, S., et al. (2008) "Protection of Macaques against Vaginal SHIV Challenge by Systemic or Mucosal and Systemic Vaccinations with HIV-Envelope" AIDS 22(3):339-348.
Bell, B. P. (2000). "Hepatitis A Vaccine." The Pediatric Infectious Disease Journal 19(12): 1187-1188.
Berkner, K.L. (1988). "Development of Adenovirus vector for the expression of heterologous genes." BioTechniques 6: 616-629.
Bett, A. J., et al. (1993). "Packaging capacity and stability of human adenovirus type 5 vectors." J. Virol. 67(10): 5911-5921.

Bjune, G., et al.(1991). "Effect of outer membrane vesicle vaccine against group B meningococcal disease in Norway." Lancet 338(8775): 1093.
Boris-Lawrie, K. A. and H. M. Temin (1993). "Recent advances in retrovirus vector technology." Current Opinion in Genetics & Development 3(1): 102-109.
Budka, H. (1997) "The Human Prion Diseases: From Neuropathology to Pathobiology and Molecular Genetics" Neuropathol. Appl. Neurobiol. 23(5):416-422.
Burns, J. C., T. Friedmann, et al. (1993). "Vesicular stomatitis virus G glycoprotein pseudotyped retroviral vectors: concentration to very high titer and efficient gene transfer into mammalian and nonmammalian cells." Proceedings of the National Academy of Sciences of the United States of America 90(17): 8033-8037.
Carter, B. J. (1992). "Adeno-associated virus vectors." Current Opinion in Biotechnology 3:533-539.
Chen, X., Y. Li, et al. (1994). "A self-initiating eukaryotic transient gene expression system based on cotransfection of bacteriophage T7 RNA polymerase and DNA vectors containing a T7 autogene." Nucl. Acids Res. 22(11): 2114-2120.
Costantino, P., F. Norelli, et al. (1999). "Size fractionation of bacterial capsular polysaccharides for their use in conjugate vaccines." Vaccine 17(9-10): 1251-1263.
Dale, J. (1999). "Group A *Streptococcal* vaccines." Infectious disease clinics of North America 13(1): 227-243.
Darmstadt, G., et al. (2003). "Neonatal Oil Massage." Indian Pediatrics 40(11): 1098-1099.
Darmstadt, G., et al. (2002). "Impact of topical oils on the skin barrier: possible implications for neonatal health in developing countries." Acta Paediatrica 91(5): 546-554.
Darmstadt, G., et al. (2002) "Traditional ractice of Oil Message of Neonates in Bangladesh" J. Health Popul. Nutr. 20(2):184-188.
Del Giudice, G., et al. (1998). "Molecular basis of vaccination." Molecular Aspects of Medicine 19(1): 1-70.
Deng, H., et al.(1994). "Self-amplifying expression from the T7 promoter in 3T3 mouse fibroblasts." Gene 143(2): 245-249.
Doe, B., et al. (1994). "Induction of HIV-I envelope (gp120)-specific cytotoxic T lymphocyte responses in mice by recombinant CHO cell-derived gp120 is enhanced by enzymatic removal of N-linked glycans." European Journal ofImmunology 24(10): 2369-2376.
Dreesen, D. W. (1997). "A global review of rabies vaccines for human use." Vaccine 15(Supplement 1): S2-S6.
Elroy-Stein, O. et al. (1990). "Cytoplasmic expression system based on constitutive synthesis of bacteriophage T7 RNA polymerase in mammalian cells." Proceedings of the National Academy of Sciences of the United States of America 87(17): 6743-6747.
Enioutina, E. Y., et al. (2000). "Enhancement of common mucosal immunity in aged mice following their supplementation with various antioxidants." Vaccine 18(22): 2381-2393.
Enioutina, E. Y., et al. (2000). "The induction of systemic and mucosal immune responses to antigen-adjuvant compositions administered into the skin: alterations in the migratory properties of dendritic cells appears to be important for stimulating mucosal immunity." Vaccine 18(24): 2753-2767.
Erickson, A., et al. (1993). "Hepatitis C virus-specific CTL responses in the liver of chimpanzees with acute and chronic hepatitis c." J Immunol151(8): 4189-4199.
Ferretti, J. J., et al. (2001). "Complete genome sequence of an M1 strain of *Streptococcus pyogenes*." Proceedings of the National Academy of Sciences of the United States of America 98(8): 4658-4663.
Franchini, A., M., et al. (1991). "Vitamin E as adjuvant in emulsified vaccine for chicks." Poultry Sci. 70:1709-1715.
Franchini, A, et al. (1995) "Vitamin E in viral inactivated vaccines." Poultry Sci. 74: 666-671.
Fuerst, T. R, et al. (1986). "Eukaryotic transient-expression system based on recombinant vaccinia virus that synthesizes bacteriophage T7 RNA polymerase." Proceedings of the National Academy of Sciences of the United States of America 83(21): 8122-8126.

(56) References Cited

OTHER PUBLICATIONS

Fukasaw A, et al. (1999). "Neisseria meningitidis serogroup C polysaccharide and serogroup B outer membrane vesicle conjugate as a bivalent meningococcus vaccine candidate." Vaccine 17(23-24): 2951-2958.
Gao, X. et al.(1994). "A Sustained, Cytoplasmic Transgene Expression System Delivered by Cationic Liposomes." Biochemical and Biophysical Research Communications 200(3): 1201-1206.
Gerlich, et al. (1990). "Eradication strategies for HBV: Discussion, part 1." Vaccine 8(Supplement 1): S93-S94.
Gerlich, et al. (1990). "Recombinant DNA vaccines: Discussion." Vaccine 8(Supplement 1):S79-S80.
Gustafsson, L., et al. (1996). "A controlled trial of a two-component acellular, a five-component acellular, and a whole-cell pertussis vaccine." The New England Journal of Medicine 334(6): 349-355.
Hai-Ahmad, Y. et al. (1986). "Development of a helper-independent human adenovirus vector and its use in the transfer of the herpes simplex virus thymidine kinase gene." 1. Virol. 57(1): 267-274.
Hirano, T., et al. (2004). "Flavonoids such as Luteolin, Fisetin and Apigenin Are Inhibitors of Interleukin-4 and Interleukin-13 Production by Activated Human Basophils." International Archives of Allergy and Immunology 134(2): 135-140.
Hogan, J. S., et al. (1990). "Relationships Among Vitamin E, Selenium, and Bovine Blood Neutrophils." 1. Dairy Sci. 73(9): 2372-2378.
Hogan, J. S., et al. (1992). "Bovine Neutrophil Responses to Parenteral Vitamin E." 1. Dairy Sci. 75(2): 399-405.
Hogan, J. S., et al. (1993). "Vitamin E as an Adjuvant in an *Escherichia coli* 15 Vaccine." 1. Dairy Sci. 76(2): 401-407.
Hsu, H.,et al. (1999) "Prospects for a hepatitis C virus vaccine." Clin. Liver Dis. 3:901-15.
Inoue, H., et al. (1997). "Mechanism of mustard oil-induced skin inflammation in mice." European Journal of Pharmacology 333(2-3): 231-240.
Ivanov, A. et al. (2006). "1,25—Dihydroxyvitamin D3 Enhances Systemic and Mucosal Immune Responses to Inactivated Poliovirus Vaccine in Mice." The Journal of Infectious Diseases 193(4): 598-600.
Iwarson, S. (1995). "New approaches to hepatitis A and B vaccines." APMIS 103(1-6): 321-326.
Allyl isothiocyanate—http://en.wikipedia.org/wiki/Allyl_isothiocyanate.
Rubefacient—http://en.wikipedia.org/wiki/Rubefacient.
Jason, J., et al. (2002). "Vitamin A Levels and Immunity in Humans." Clin. Diagn. Lab. Immunol. 9(3): 616-621.
Jedrzejas, M. J. (2001). "Pneumococcal virulence factors: structure and function." Microbiol. Mol. Biol. Rev. 65(2): 187-207.
Jeffery, H., et al. (1993). "The preparation and characterization of poly(lactide-co-glycolide) microparticles. II. The entrapment of a model protein using a (water-in-oil)-in-water emulsion solvent evaporation technique." Pharmaceutical Research 10(3): 362-368.
Jin, Y., et al. (2006). "Separation of catechin compounds from different teas." Biotechnology Journal 1(2): 209-213.
Kalman, S., et al. (1999). "Comparative genomes of Chlamydia pneumoniae and C. trachomatis." Nature Genetics 21(4): 385.
Kang, T. H., et al. (2007). "Epigallocatechin-3-Gallate Enhances CD8+ T Cell-Mediated Antitumor Immunity Induced by DNA Vaccination." Cancer Res 67(2): 802-811.
Katiyar, S. K., et al. (1999). "Prevention of UVB-induced immunosuppression in mice by the green tea polyphenol (−)-epigallocatechin-3-gallate may be associated with alterations in IL-10 and IL-12 production." Carcinogenesis 20(11): 2117-2124.
Kirk, D. D., et al. (2004). "Application of Quillaja saponaria extracts as oral adjuvants for plantmade vaccines." Expert Opinion on Biological Therapy 4(6): 947-958.
Kotin, R. M. (1994). "Prospects for the use of adeno-associated virus as a vector for human gene therapy." Human Gene Therapy 5:793-801.
Lalv Ani, A., et al. (1997). "Rapid Effector Function in CD8+ Memory T Cells." J. Exp. Med. 186(6): 859-865.

Lebkowski, J. S., et al. (1988). "Adeno-associated virus: a vector system for efficient introduction and integration of DNA into a variety of mammalian cell types." Mol. Cell. Biol. 8(10): 3988-3996.
Lim, S.-Y., et al. (2006). "Phytol-based novel adjuvants in vaccine formulation: 1. assessment of safety and efficacy during stimulation of humoral and cell-mediated immune responses." Journal of Immune Based Therapies and Vaccines 4(1): 6-17.
Lindberg, A. A. (1999). "Glycoprotein conjugate vaccines." Vaccine 17(Supplement 2): S28-S36.
Louis, A. J., et al. (1989). "The role of substance P and calcitonin gene-related peptide in neurogenic plasma extravasation and vasodilatation in the rat." Neuroscience 32(3): pp. 581-586.
Ma, Y., et al. (2005). "The anti-tetanus immune response of neonatal mice is augmented by retinoic acid combined with polyriboinosinic:polyribocytidylic acid." Proceedings of the National Academy of Sciences of the United States of America 102(38): 13556-13561.
Manesh et al. Effect of Naturally Occurring Isothiocyanates on the Immune System. Immunopharmacology and Immunotoxicology 25(3): 451-459 (2003).
Mantena, S., et al. (2005). "Epigallocatechin-3-Gallate Inhibits Photocarcinogenesis Through Inhibition of Angiogenic Factors and Activation of CD8J\sup +J\ T Cells in Tumors." Photochemistry and Photobiology 81(5), 1174-9.
Mason, L., et al. (2004). "Systematic review of efficacy of topical rubefacients containing salicylates for the treatment of acute and chronic pain." BMJ 328(7446): 995-997.
Matsunaga, K., et al. (2001). "Legionella pneumophila Replication in Macrophages Inhibited by Selective Immunomodulatory Effects on Cytokine Formation by Epigallocatechin Gallate, a Major Form of Tea Catechins." Infect. Immun. 69(6): 3947-3953.
McGee, J. P., et al. (2009). "The encapsulation of a model protein in poly (D, L lactide-coglycolide) microparticles of various sizes: an evaluation of process reproducibility." Journal of Microencapsulation 14(2): 197-210.
Mcheyzer-Williams, M.G., et al. (1996). "Enumeration and characterization of memory cells in the TH compartment" Immunol. Rev. 50: 1-21.
McMichael, A. J., et al. (1998). "A New Look at T Cells." J. Exp. Med. 187(9): 1367-1371.
McMichael, J. C. (2000). "Vaccines for Moraxella catarrhalis." Vaccine 19(Supplement 1):S101-S107.
Michael, S. I., et al. (1993). "Binding-incompetent adenovirus facilitates molecular conjugatemediated gene transfer by the receptor-mediated endocytosis pathway." Journal of Biological Chemistry 268(10): 6866-6869.
Miller, A. D. (1990). "Retrovirus Packaging Cells." Human Gene Therapy 1(1): 5-14.
Miller, A.D., et al. (1989). "Improved retroviral vectors for gene transfer and expression." Biotechniques.7:980-990.
Miller, M., et al. (2001). "Dietary antioxidants protect gut epithelial cells from oxidant-induced apoptosis." BMC Complementary and Alternative Medicine 1(1): 11.
Mittereder, N., et al. (1994). "Evaluation of the efficacy and safety of in vitro, Adenovirusmediated transfer of the human cystic fibrosis transmembrane conductance regulator cDNA." Human Gene Therapy 5(6): 717-729.
Muzyczka, N. Viral Expression Vectors: Current Topics in Microbiology and Immunology. New York: Springer-Verlag, 1992.97-129.
Nair, N., et al. (2002). "Grape Seed Extract Activates Thl Cells In Vitro." Clin. Diagn. Lab. Immunol. 9(2): 470-476.
Nash, Kevin, et al. (2008) "Complete In Vitro Reconstruction of Adeno-Associated Virus DNA Replication Requires the Minichromosome Maintenance Complex" Journal of Virology 82(3): 1458-1464.
Nuez, B. et al.(1993). "Bacteriophage Nf DNA region controlling late transcription: structural and functional homology with bacteriophage {varphi} 29." Nucl. Acids Res. 21(12): 2861-2865.
O'Hagan, D. T., et al. (1993). "Biodegradable microparticles for oral immunization." Vaccine 11(2): 149-154.

(56) References Cited

OTHER PUBLICATIONS

Pizza, M., et al. (2000). "Identification of Vaccine Candidates Against Serogroup B Meningococcus by Whole-Genome Sequencing." Science 287(5459): 1816.

Prinz, W., et al. (1980). "A systematic study of the effect of vitamin C supplementation on the humoral immune response in ascorbic-dependent mammals." Int. J. Vit. Nutr. Res. 50: 294-300.

Ramanathapuram, L. V., et al. (2006). "Vesiculated alpha-tocopheryl succinate enhances the anti-tumor effect of dendritic cell vaccines." Cancer Immunology, Immunotherapy: CII 55(2):166-177.

Ramsay, M. E., et al. (2001). "Efficacy of meningococcal serogroup C conjugate vaccine in teenagers and toddlers in England." Lancet 357(9251): 195-6.

Rappuoli, R., et al. (1991). "Towards third-generation whooping cough vaccines." Trends in Biotechnology 9(1): 232-238.

Read, R. C, et al. (2000). "Genome sequences of Chlamydia trachomatis MoPn and Chlamydia pneumoniae AR39". Nucleic Acids Research, 28(6), 1397-1406.

Rich, D. P., et al. (1993). "Development and analysis of recombinant Adenoviruses for gene therapy of cystic fibrosis." Human Gene Therapy 4(4): 461-476.

Romanowski, et al. "Thiocyanates and Isothiocyanates, Organic" in Ullmann's Encyclopedia of Industrial Chemistry, 2000, Wiley-VCH: Weinheim.

Rosenqvist et al. (1998) Effect of Aluminium Hydroxide and meningococcal Serogroup C Capsular Polysaccharide on the Immunogencity and Reactogenicity of a Group B Neisseria meningitidis Outer Membrane Vesicle Vaccine, Dev. Biol. Stand. 92:323-333.

Ross, B. C, L. Czajkowski, et al. (2001). "Identification of vaccine candidate antigens from a genomic analysis of Porphyromonas gingivalis." Vaccine 19(30): 4135-4142.

Rubin, L. (2000). "Pneumococcal vaccine." Pediatric clinics of North America 47(2): 269-285.

Saurer, L., et al. (2007). "In Vitro Induction of Mucosa-Type Dendritic Cells by All-Trans Retinoic Acid." Ilmmunol. 179(6): 3504-3514.

Scarp A, M., et al. (1991). "Characterization of recombinant helper retroviruses from moloney-based vectors in ecotropic and amphotropic packaging cell lines." Virology 180(2): 849.

Schuchat, A. (1999). "Group B *Streptococcus*." Lancet 353(9146): 51-56.

Schultze V., et al. (2008). "Safety of MF59™ adjuvant." Vaccine, 26 (26), 3209-3222.

Seth et al., (1994) "Mechanism of enhancement of DNA expression consequent to cointernalization of a replication-deficient adenovirus and unmodified plasmid DNA." 1. Virol. 68(2): 933-940.

Shelling, A. N., et al. (1994). "Targeted integration of transfected and infected adenoassociated virus vectors containing the neomycin resistance gene." Gene Therapy 1(3): 165-169.

Mingke Yu et. al. (2011), "A novel retinoic acid, catechin hydrate and mustard oil-based emulsion for enhanced cytokine and antibody responses against multiple strains of HIV-1 following mucosal and systemic vaccinations", Vaccine, Elsevier Ltd, GB, vol. 29, No. 13, pp. 2429-2436.

Examination Report No. 1 issued in corresponding Australian Application No. 2017221829 dated Apr. 6, 2018.

Office Action issued in corresponding Canadian Application No. 2,839,507 dated May 17, 2018.

Pre-Appeal Reexamination Report issued in corresponding Japanese Application No. 2014-517233 dated Feb. 23, 2018 and its English Translation.

Office Action issued in corresponding Japanese Application No. 2014-517233 dated Sep. 10, 2018 and its English Translation.

First Examination Report issued in corresponding Indian Application No. 394/CHENP/2014 dated Jan. 31, 2019.

Vaccine Handbook, Maruzen, Inc., 1996, pp. 36-46.

* cited by examiner

PHARMACEUTICAL COMPOSITIONS, COMPRISING A COMBINATION OF SELECT CARRIERS, VITAMINS, TANNINS AND FLAVONOIDS AS ANTIGEN-SPECIFIC IMMUNO-MODULATORS

CROSS REFERENCE TO RELATED APPLICATIONS

This application claims priority under 35 U.S.C. § 119(e) to U.S. Provisional Application No. 61/500,993, filed Jun. 24, 2011 and U.S. Provisional Application No. 61/513,840, filed Aug. 1, 2011. This application claims priority under 35 U.S.C. § 120 as a continuation-in-part of U.S. patent application Ser. No. 12/651,975, filed on Jan. 4, 2010, which claims priority under 35 U.S.C. § 119(e) to U.S. Provisional Application No. 61/204,316, filed Jan. 5, 2009.

GOVERNMENT SUPPORT

This invention was made with government support under Grant No. 1R43AI084690-01 awarded by the National Institute of Health. Thus, the government may have certain rights in this invention.

TECHNICAL FIELD

The present disclosure relates to adjuvant compositions and methods for using the same.

BACKGROUND

Vaccines are very cost effective medical interventions. However, although many diseases have been prevented through vaccinations, many others remain to be prevented and/or treated. Moreover, improved vaccines are needed for a number of diseases for which vaccines already exist. A major hurdle in producing effective vaccines is the lack of or low immunogenicity of the vaccine. The effectiveness of a vaccine can be enhanced by using adjuvants and delivery systems.

SUMMARY

The present invention provides adjuvant compositions that are capable of modulating the immune response in a subject, including enhancing or suppressing the immune response. These adjuvant compositions may also be used to enhance or suppress the immunogenicity of antigens by enhancing or suppressing antigen-presentation activity, enhancing or suppressing innate immune responses through activation or suppression of, e.g., natural killer cells, and/or direct activation of subsets of B and/or T cells, or other cells. Also provided are methods of making the adjuvant compositions as well as methods of using the adjuvant compositions.

In certain embodiments, the compositions include a pharmaceutically acceptable carrier; at least one flavonoid and/or at least one tannin and at least one vitamin.

In certain cases, the pharmaceutically acceptable carrier may be an organic carrier or an inorganic carrier. Examples of inorganic carriers include an aluminum salt, e.g., aluminum hydroxide or aluminum phosphate. Examples of organic carriers include liposomes, oils, and the like. In certain embodiments, the pharmaceutically acceptable carrier may be an oil, such as animal oil, vegetable oil, fossil oil, synthetic oil, and the like. Examples of animal oil include fish oil, shark liver oil, etc. Examples of vegetable oil include mustard oil, coconut oil, safflower oil, etc.

In certain embodiments, the flavonoid is a derivative and/or salt thereof. Nonlimiting examples of the flavonoids of the invention include, a catechin, a flavonoid derivative, and a flavonoid derivative salt. In certain cases, the flavonoid is a catechin, or a derivative or a salt thereof.

In certain embodiments, the tannin is a derivative and/or salt thereof. Nonlimiting examples of the tannins of the invention include, gallic acid, a gallic acid derivative, and a gallic acid derivative salt. In certain cases, the tannin is a gallic acid, or a derivative or a salt thereof.

In certain embodiments, the vitamin, is a derivative and/or salt thereof. The vitamin may be a water soluble vitamin, such as, Vitamin B and Vitamin C or a fat-soluble vitamin such as, Vitamin A, D, K and E.

In certain embodiments, the composition may include a pharmaceutically acceptable carrier, a catechin, or a derivative or salt thereof, gallic acid or a derivative thereof, and Vitamin A, or a derivative or a salt thereof. In certain embodiments, the composition includes a pharmaceutically acceptable carrier, a catechin, or a derivative or salt thereof, and Vitamin E, or a derivative or a salt thereof.

The compositions of the present invention may further comprise allyl isothiocyanate, particularly where the route of administration is mucosal, or trans-epithelial through the skin. Accordingly, in certain embodiments, the composition includes the a pharmaceutically acceptable carrier, a flavonoid, such as catechin, a vitamin, such as Vitamin A and allyl isothiocyanate.

In certain embodiments, physical conjugation by any means of an antigen of interest to a flavonoid, and mixture with a pharmaceutically acceptable carrier through the mucosal routes, e.g. oral, sublingual, intra-nasal, may induce immune-suppression, e.g. in the form of oral tolerance, i.e. systemic and/or mucosal immune unresponsiveness to subsequent antigenic contact of the host. If the pharmaceutically acceptable carrier is a lipid or fatty acids, then the antigen of interest can be physically conjugated to the lipid or fatty acids in addition to or instead of the physical conjugation by any means of the antigen to the flavonoid.

In certain other aspects, the composition includes an antigen. In certain embodiments the antigen may be conjugated to pharmaceutically acceptable carrier, the flavonoid or the vitamin of the composition. In certain embodiments the pharmaceutically acceptable carrier may comprise one or more fatty acid, e.g. Oleic Acid, Linoleic Acid, Alpha Linolenic Acid, or lipids to which the antigen is conjugated or physically linked by any means.

The compositions may be administered to a subject, such as a mammal, by a number of routes, such as, intranasal, pulmonary, sublingual, oral, buccal, intra-vaginal, intra-rectal, ocular, intradermal, transdermal, transcutaneous, subcutaneous, intra-venous and intramuscular.

Also provided are methods for making the compositions, the method includes admixing the pharmaceutically acceptable carrier, the flavonoid and the vitamin to produce the compositions.

Methods of using the compositions are also provided herein. The methods comprise administering the compositions to a subject to modulate an immune response in the subject.

Before the present invention and specific exemplary embodiments of the invention are described, it is to be understood that this invention is not limited to particular embodiments described, which may, of course, vary. It is also to be understood that the terminology used herein is for the purpose of describing particular embodiments only.

Although any methods and materials similar or equivalent to those described herein can also be used in the practice or testing of the present invention, certain preferred methods and materials are now described. All publications mentioned herein are incorporated herein by reference to disclose and describe the methods and/or materials in connection with which the publications are cited.

It must be noted that as used herein, the singular forms "a", "an", and "the" include plural referents unless the context clearly dictates otherwise. Thus, for example, reference to "a composition" or "an adjuvant composition" includes one and/or a plurality of such compositions, reference to "a vitamin" includes one, two, or more vitamins, and reference to "a flavonoid" or "a tannin" includes one, two, or more flavonoids, or tannins and so forth.

BRIEF DESCRIPTION OF THE DRAWINGS

For a more complete understanding of the present invention and the advantages thereof and by way of nonlimiting example only, reference is made to the following descriptions, taken in conjunction with the accompanying illustrative drawings, in which.

DETAILED DESCRIPTION OF EXEMPLARY EMBODIMENTS

Figure 1A:
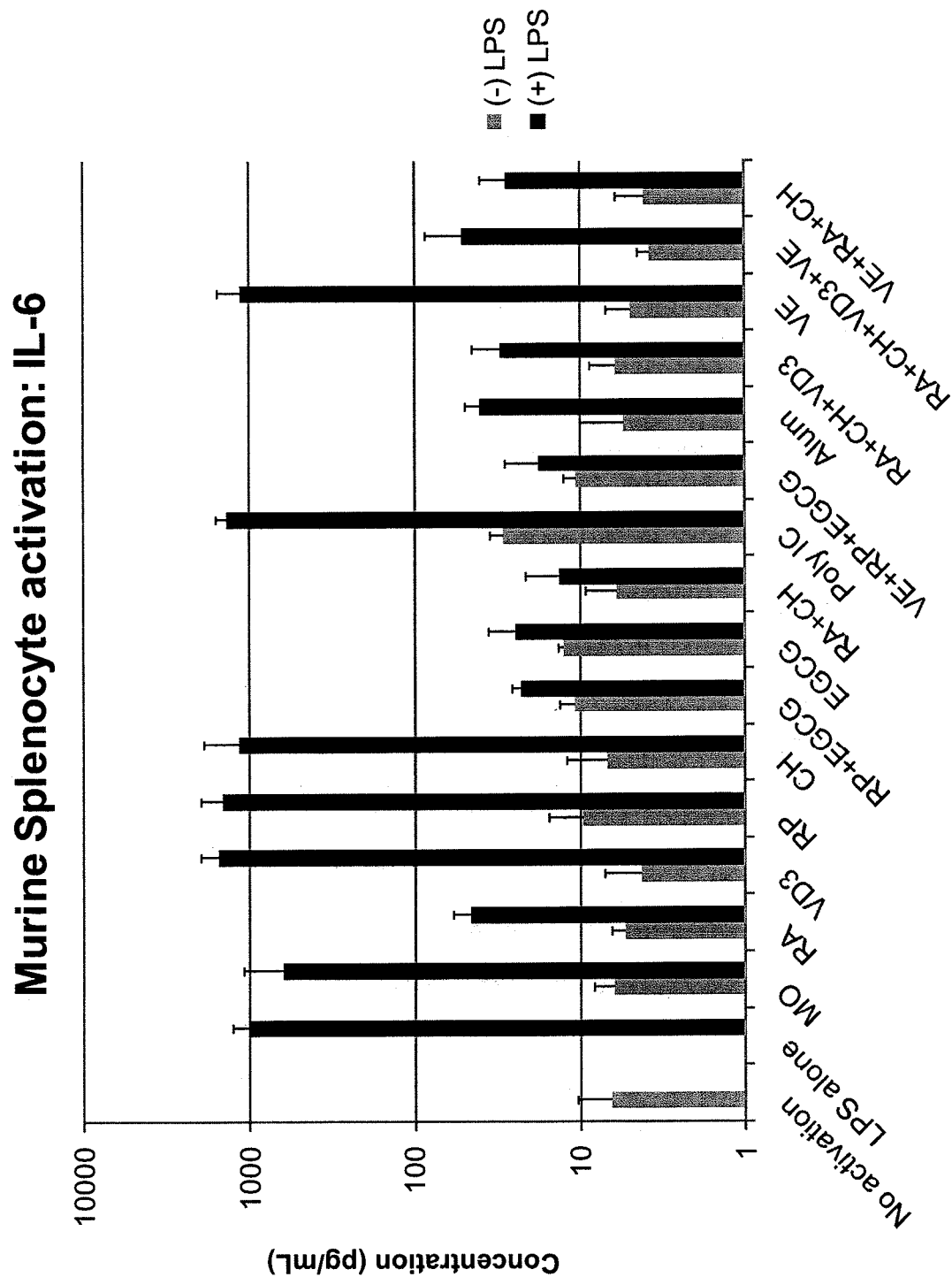
FIG. 1A is a bar graph showing interleukin 6 (IL-6) production by murine splenocytes following four days of in vitro activation with various components (MO: mustard oil; RA: retinoic acid; VD3: vitamin D3; RP: retinyl palmitate; CH: catechin hydrate; EGCG: epigallo catechin gallate; VE: vitamin E (α-tocopherol)), poly (I:C), alum (imject) or no activation, in the presence or absence of LPS.

The present disclosure provides adjuvant compositions that are capable of modulating the immune response in a subject. These adjuvant compositions may also be used to enhance the immunogenicity of antigens by enhancing antigen-presentation, enhancing innate immune responses through activation of, e.g., natural killer T cells, and/or direct B or T (or other) cell activation. Also provided are methods of making the adjuvant compositions as well as methods of using the adjuvant compositions.

Definitions

The phrases "adjuvant composition(s)" refer to a composition that when administered to a subject is capable of inducing an immune response in the subject. When administered in combination with an antigen, the "adjuvant compositions" are capable of eliciting an antigen-specific immune response.

An "immune response" to an antigen or composition is the development in a subject of an innate, humoral and/or a cellular immune response to molecules present in the antigen or composition of interest. An innate immune response is an early (within hours and days) immune response by any cells of the immune system and or epithelial cells, endothelical cells, etc. A "humoral immune response" refers to an immune response mediated primarily by antibody molecules, while a "cellular immune response" is one mediated primarily by T-lymphocytes and/or other white blood cells.

The phrase "pharmaceutically acceptable" refers to a substance that is generally safe and is acceptable for veterinary pharmaceutical use when the subject is a non-human and human pharmaceutical use, when the subject is a human.

The term "antigen component" refers to any substance that can be recognized by the immune system (e.g., bound by an antibody or processed so as to elicit a cellular immune response by, e.g. T cells) under appropriate conditions. An antigen component contains one or more epitopes. A B-cell epitope includes at least about 3-5 amino acids, for example, 4 or more amino acids. A hapten or a polysaccharide may also serve as a B cell epitope. A T-cell epitope, such as a cytotoxic T-cell (CTL) epitope, may include at least about 7-9 amino acids, for example, 8 or more amino acids. A helper T-cell epitope may include at least about 12-20 amino acids. The term "antigen component" denotes both subunit antigens (i.e., antigens which are separate from the whole organism with which the antigen is associated in nature), as well as, killed, attenuated or inactivated bacteria, viruses, fungi, parasites or other microbes, prions, allergens or any other disease causing agents. An antigen component may be a modified protein that includes modifications, such as deletions, additions and substitutions (generally conservative in nature) to the native protein sequence. The term antigen component also denotes nucleic acids (DNA or RNA) encoding a protein or peptide antigen.

"Penetration enhancement" or "permeation enhancement" as used herein refers to increasing the permeability of skin or mucosa to an antigen so as to increase the rate at which the antigen passes through the skin or mucosa and enters the lymph node or the blood stream.

A "therapeutically effective amount" or "efficacious amount" means the amount of a compound that, when administered to a mammal or other subject for preventing or treating a disease, is sufficient to affect such prevention or treatment for the disease. The "therapeutically effective amount" will vary depending on the compound, the disease and its severity and the age, weight, etc., of the subject to be treated.

Overview

The present invention provides adjuvant compositions that are capable of modulating an immune response. These adjuvant compositions may be used to induce an immune response in the absence of antigen or enhance the immunogenicity of antigens by enhancing antigen-presentation, enhancing innate immune responses through activation of, e.g. natural killer cells, and/or by direct B and T cell or other cell (e.g. epithelial, endothelial, etc) activation. The adjuvant compositions may also be sued to suppress an immune response. Also provided are methods of making the adjuvant compositions as well as methods of using the adjuvant compositions.

Compositions

Adjuvant compositions provided herein may include: a pharmaceutically acceptable carrier; a flavonoid; a tannin, and a vitamin. The vitamin may be a fat-soluble vitamin, e.g., Vitamin A, Vitamin E, and Vitamin D, or a water-soluble vitamin, e.g., Vitamin C and Vitamin B, and/or derivatives or salts of such vitamins. The compositions may contain two or more vitamins. In certain embodiments, the adjuvant composition may include two or more flavonoids and/or two or more vitamins. In particularly preferred embodiments, the vitamin is Vitamin A, Vitamin E, Vitamin D and combinations thereof.

In certain cases, the pharmaceutically acceptable carrier may be an organic carrier or an inorganic carrier. Examples of inorganic carriers include alum and other aluminum salts, e.g., aluminum hydroxide (Alum) or aluminum phosphate. Examples of organic carriers include liposomes, oils, and the like. In certain embodiments, the pharmaceutically acceptable carrier may be oil, such as, animal oil, vegetable oil, fossil oil, synthetic oil, and the like. Examples of animal oil include fish oil, shark liver oil, squalene oil, squalene, etc. Examples of vegetable oil include mustard oil, corn oil, olive oil, grape seed oil, coconut oil, safflower oil, etc. In a particularly preferred embodiment, the pharmaceutically acceptable carrier is a fish oil, such as fish squalene oil, or squalene.

In another embodiment, the compositions provided herein include: pharmaceutically acceptable oil with or without allyl isothiocyanate (essential oil of mustard); and at least one flavonoid, at least one tannin and at least one vitamin.

In some embodiments, the compositions comprise an oil in water emulsion. The oil in water emulsion may be produced by use of a high pressure homogenization process, which applies pressures of 500-30000 psi to force the emulsion through a narrow nozzle, resulting in a homogeneous emulsion. In certain embodiments, the homogeneous emulsion comprises droplets/particle sizes of 30-100 nm.

In some embodiments, where an antigen is included in the composition, the antigen is added during the preparation of the emulsion, while in other embodiments the antigen is added after the emulsion has been prepared, and is simply mixed with the already formed emulsion. An antigen may also be administered separately from the compositions.

In certain embodiments, the adjuvant compositions provided herein include: a pharmaceutically acceptable oil; at least one flavonoid and/or tannin; and at least one vitamin. In certain embodiments, the oil may be an animal oil, such as fish oil, or a vegetable oil, such as mustard oil.

In another embodiment, the compositions provided herein include: mustard oil with or without allyl isothiocyanate (essential oil of mustard); at least one flavonoid; and at least one vitamin.

In certain embodiments the pharmaceutically acceptable oil does not include oil bodies. The pharmaceutically acceptable oil may be isolated from any cell that contains oil bodies (or oil body-like structures) including plant cells, animal cells, fungal cells and bacterial cells. In certain embodiments, the pharmaceutically acceptable oil is a vegetable oil.

In the seeds of oilseed crops, which include economically important crops, such as soybean, rapeseed, sunflower and palm, the water insoluble oil fraction is stored in discrete subcellular structures known in the art as oil bodies, oleosomes, lipid bodies or spherosomes (Huang 1992, Ann. Rev. Plant Mol. Biol. 43: 177-200). Besides a mixture of oils (triacylglycerides), which chemically are defined as glycerol esters of fatty acids, oil bodies comprise phospholipids and a number of associated proteins, collectively termed oil body proteins. From a structural point of view, oil bodies are considered to be a triacylglyceride matrix encapsulated by a monolayer of phospholipids in which oil body proteins are embedded (Huang, 1992, Ann. Rev. Plant Mol. Biol. 43: 177-200). The seed oil present in the oil body fraction of plant species is a mixture of various triacylglycerides, of which the exact composition depends on the plant species from which the oil is derived.

In certain embodiments, the pharmaceutically acceptable oil of the present invention does not include substantially intact oil bodies. The term "substantially intact oil bodies" as used herein means that the oil bodies have not released greater than 50% (v/v) of their total seed oil content in the form of free oil. In certain embodiments, the pharmaceutically acceptable oil is free oil that has been released from the rupturing of the oil bodies. In certain embodiments, the pharmaceutically acceptable oil is free oil and the oil bodies present in the free oil have released greater than 50% (v/v) of their total seed oil content in the form of free oil.

In certain embodiments, the pharmaceutically acceptable oil in the compositions described herein is free oil that is prepared by a process that results in rupture of oil bodies such that the free oil does not include substantial levels of intact oil bodies. In certain embodiments, the pharmaceutically acceptable oil is prepared by a process by which 40% to 95%, such as about 45%-90%, about 50%-90%, about 60%-90%, about 70% to 90%, for example, about 40%, about 50%, about 60%, about 70%, about 80%, about 90% of the oil present in a cell is released in the form of free oil, where free oil is oil that is not present in the form of oil bodies. In other words, free oil in the form of fatty acids or triacylglycerides that is not surrounded or encapsulated by oil body proteins, such as oleosins or containing a monolayer of phospholipids. In certain embodiments, the pharmaceutically acceptable carrier is free oil which is not surrounded or encapsulated by a monolayer of phospholipids.

In certain embodiments, the pharmaceutically acceptable carrier is free oil which does not include significant levels of plant proteins, such as, proteins found in oil bodies, e.g., oil body proteins, such as, oleosin. In certain embodiments, the compositions provided herein do not include more than 0.001%-50% weight/volume (w/v) of plant protein, for example, more than about 0.001%, more than about 0.01%, more than about 0.1%, more than about 1%, more than about 10%, more than about 20%, more than about 30%, more than about 40%, more than about 50% w/v of plant protein.

In certain embodiments, the pharmaceutically acceptable carrier may be vegetable oil. The vegetable oil may be isolated from plants, such as, plant seeds. The vegetable oil may be prepared by a process by which the oil present in a plant seed is released in the form of free oil that does not include significant levels of oil bodies.

In certain embodiments, the pharmaceutically acceptable carrier may be free oil as described above. The free oil does not include significant levels of oil bodies. In certain embodiments, the free oil does not include more that 0.0000001% weight/volume to 50% weight/volume of oil bodies. In certain cases, the oil bodies are present at less than 50% weight/volume, less than 40% weight/volume, less than 30% weight/volume, less than 20% weight/volume, less than 10% weight/volume, less than 5% weight/volume, less than 1% weight/volume, less than 0.5% weight/volume, less than 0.1% weight/volume in the free oil present in the compositions described herein.

In certain embodiments, the free oil present in the compositions provided herein does not include more than 0.001%-50% weight/volume (w/v) of plant protein, e.g., oil body protein, for example, more than about 0.001%, more than about 0.01%, more than about 0.1%, more than about 1%, more than about 10%, more than about 20%, more than about 30%, more than about 40%, more than about 50% w/v of plant protein.

The flavonoid comprises flavonoid derivatives, salts and salts of derivatives. In certain embodiments, the flavonoid is a flavone, a flavonol, a flavonone, a catechin, anthocyanid, or isoflavone, or derivatives, salts, or salts of the derivatives thereof. In certain embodiments, the flavonoid is a catechin, such as, catechin hydrate.

The vitamin includes vitamin derivatives, salts and salts of derivatives. In certain embodiments, the vitamin includes one or more vitamins, such as, Vitamin A, Vitamin E, Vitamin D, Vitamin C and Vitamin B, and derivatives, salts and salts of derivatives thereof. In certain preferred embodiments, the vitamin is Vitamin A. In other preferred embodiments, the vitamin is Vitamin E.

The adjuvant compositions may additionally include other additives, such as preservatives, colorants, flavorants, etc. The adjuvant compositions may additionally include an antigen.

Pharmaceutically Acceptable Organic Carriers

A "pharmaceutically acceptable vegetable oil carrier" as used herein refers to a vegetable oil that is suitable for administration to a human or non-human animal by a desirable route, e.g., systemic or mucosal route, including oral and topical routes of delivery. Edible adjuvant compositions are contemplated by the present disclosure.

"Vegetable oil" refers to oil obtainable from a plant or a plant product, and encompasses oil obtainable from seeds (including nuts, grains), fruits, roots, flowers, stems, etc. Examples include corn oil, mustard oil, olive oil, grape seed oil, coconut oil, safflower oil, soybean oil, squalene oil or squalene, and the like. Vegetable oils of the present disclosure encompass oils obtainable from non-genetically modified and from genetically modified plants. Vegetable oils encompass vegetable oils having properties of a rubefacient, i.e., oils that promotes dilation of capillaries and an increase in blood circulation, e.g., when applied topically to skin. Vegetable oil may be derived from a plant or plant product (e.g., a non-genetically modified or genetically modified plant or plant product), or may be produced synthetically, e.g., by mixing the individual components found in vegetable oils, where the individual components may be derived from any source, such as, plants or plant products, animals, animal products, fossil oils, or produced synthetically. The plants which provide the source for the vegetable oil or the individual fatty acids may be genetically modified.

In certain embodiments, the vegetable oil is a mustard oil. "Mustard oil" as used herein refers to oil that is obtainable from seeds of a mustard plant of Brassicacae, where the oil is obtainable from the mustard plant without application of heat during extraction (e.g., obtainable by a cold-press extraction method). Mustard oil obtainable from seeds of a mustard plant without application of heat have a lower amounts of (e.g., no significant or detectable) allyl isothiocyanate than oil that may be obtainable from the same seeds using a heat-based extraction method (e.g., by application of steam). Mustard plants of Brassicacae from which mustard oils useful as carriers in the compositions of the present disclosure may be obtainable include, but are not necessarily limited to, *Brassica rapa* (edible greens), *Brassica nigra* (black mustard), *Brassica juncea* (brown mustard), *Brassica hirta* (white or yellow mustard), *Brassica carinata* (Ethiopian mustard), *Brassica oleracea* (wild mustard), *Brassica campestris* (including *Brassica napus* L. and *B. campestris* L.), and *Brassica napus*. Oils contemplated by "mustard oil" can include oil obtainable from rapeseed.

As noted in the preceding section, the vegetable oil is preferably free oil and as such does not comprise substantial levels of substantially intact oil bodies. In certain embodiments, the vegetable oil is canola oil. Such canola oil may have the following composition: 6-8% Saturated Fatty Acids (with 3.5 Palmitic Acid); 14.4% Monounstaurated Fatty Acids (with 60% Oleic Acid); and 69.3% Polyunsaturated Fatty Acids (with 20% Linoleic Acid, 10% Alpha Linolenic Acid).

In certain embodiments, the vegetable oil used in the compositions described herein may comprise about 14%-70% monounsaturated fatty acids, about 18%-22% polyunsaturated fatty acids and about 5%-12% saturated fatty acids. The monounsaturated fatty acids may have about 18%-51% erucic acid and about 7%-22% oleic acid, the polyunsaturated fatty acids may have about 9-15% linolenic acid and about 6-24% linoleic acid, and the saturated fatty acids may have about 3-4% palmitic acid.

In certain embodiments, the vegetable oil used in the compositions described herein may comprise about 14%-70% monounsaturated fatty acids, 18%-22% polyunsaturated fatty acids and 5%-12% saturated fatty acids.

In certain embodiments, the vegetable oil used in the compositions described herein may comprise about 14%-20% monounsaturated fatty acids, 18%-20% polyunsaturated fatty acids and 5%-6% saturated fatty acids.

In certain embodiments, the vegetable oil used in the compositions described herein may comprise about 60%-70% monounsaturated fatty acids, about 18%-22% polyunsaturated fatty acids and about 5%-6% saturated fatty acids.

Where the vegetable oil is a mustard oil, in certain embodiments, the mustard oil may have the following composition: monounsaturated fatty acids (erucic acid (18-51%), oleic acid (7-22%)), polyunsaturated fatty acids (linolenic (9-15%) and linoleic (6-24%)), and 5% saturated fatty acids. The mustard oil may additionally also include other components, such as, proteins (30%), phenolics, phytin and dithio]thiones. Mustard oil may also contain 490 mg/100 gm of calcium. Mustard oil may also contain 9-15% omega 3 fatty acids.

In some embodiments, the mustard oil is one obtainable from *Brassica rapa*. Mustard oil obtainable from *Brassica rapa* includes an oil having the following composition: 5.4% Saturated Fatty Acids (with 2.7% Palmitic Acid, 1.0% Stearic Acid, 0.6% Behenic, and 1.1% other saturated fatty acids); 67.3% Monounsaturated Fatty Acids (with 23.3% Oleic, 10.0% Gadoleic, 33.8% Erucic); and 20.6% Polyunsaturated Fatty Acids (with 9.4% Linoleic Acid, 9.9% Alpha Linolenic Acid).

In certain embodiments, the vegetable oil carrier may be a mixture of one or more vegetable oils, for example, mustard oil (with or without added AIT) and corn oil; mustard oil (with or without added AIT) and soy bean oil; mustard oil (with or without AIT) and coconut oil. The present disclosure also contemplates compositions having a vegetable oil carrier that itself is a rubifacient and/or combined with a rubefacient oil. Examples of rubefacient oils include Oil of Wintergreen (Methyl Salicylate), mustard oil, and Rosemary oil (*Rosmarinus officinalis*).

In other embodiments, the oil carrier may be a single fatty acid (e.g. oleic acid) or combinations of two or more fatty acids.

In certain embodiments, the pharmaceutically acceptable carrier may be oil in the form of fatty acids, such as omega 3 (e.g. eicosapentaenoic acid (EPA), and docosahexaenoic acid (DHA)) or omega-6 fatty acids (e.g. linoleic acid), in various proportions, e.g. 1:1, isolated from plant or animal oils or genetically modified microorganisms or produced by chemical synthesis In certain embodiments the vegetable oil may contain or be solely squalene from vegetables including but not limited to amaranth seed, rice bran, wheat germ, and olive.

Pharmaceutically Acceptable Animal Oil Carriers

In certain embodiments, the pharmaceutically acceptable carrier may be an oil, such as an animal oil. Animal oils include oils derived from an animal source or synthesized from individual fatty acids and mixed to produce an oil similar to animal oil. Examples of animal oils include fish oil, shark liver oil, cod oil, animal squalene, butter, chicken fat, lard, dairy butterfat, or combinations thereof, and the like. In a preferred embodiment, the pharmaceutically acceptable carrier comprises fish oil.

Pharmaceutically Acceptable Fossil Oil Carriers

In certain embodiments, the pharmaceutically acceptable carrier may be an oil, such as a fossil oil. In certain embodiments, the pharmaceutically acceptable carrier may be mineral oil. Mineral oil or liquid petroleum is a by-product in the distillation of petroleum to produce gasoline and other petroleum based products from crude oil. Mineral oil is composed mainly of alkanes (typically 15 to 40 carbons) and cyclic paraffins, related to petroleum jelly (also known as "white petrolatum"). It has a density of around 0.8 g/cm$^3$. Mineral oil is available in light and heavy grades, and can often be found in drug stores. There are three basic classes of refined mineral oils: paraffinic oils, based on n-alkanes; naphthenic oils, based on cycloalkanes; and aromatic oils, based on aromatic hydrocarbons.

Other Pharmaceutically Acceptable Carriers

It is contemplated that the carrier of the invention can be any suitable pharmaceutically acceptable carrier. In certain embodiments the pharmaceutically acceptable carrier may be virosomes, liposomes, or ISCOMS.

Pharmaceutically Acceptable Inorganic Carriers

In certain embodiments, the adjuvant compositions described herein may include a pharmaceutically acceptable inorganic carrier such as mineral-based adjuvants, e.g., salts of calcium (e.g., calcium phosphate), a salt of aluminum, such as alum, for example, aluminum hydroxide or aluminum phosphate.

A suitable alum adjuvant sold under the name Imject (Pierce, Rockford, Ill.), that consists of an aqueous solution of aluminum hydroxide (45 mg/ml) and magnesium hydroxide (40 mg/ml) plus inactive stabilizers may be used as an inorganic carrier in the compositions described herein.

Aluminum hydroxide may be aluminum hydroxide salts, which are usually at least partially crystalline. Aluminum oxyhydroxide, which can be represented by the formula AlO(OH), can be distinguished from other aluminum compounds, such as aluminum hydroxide $Al(OH)_3$, by infrared (IR) spectroscopy.

Aluminum phosphate may be aluminum hydroxyphosphates, often also containing a small amount of sulfate (i.e., aluminum hydroxyphosphate sulfate). They may be obtained by precipitation, and the reaction conditions and concentrations during precipitation influence the degree of substitution of phosphate for hydroxyl in the salt. Hydroxyphosphates generally have a $PO_4/Al$ molar ratio between 0.3 and 1.2. Hydroxyphosphates can be distinguished from strict $AlPO_4$ by the presence of hydroxyl groups. The aluminum phosphate will generally be amorphous, particularly for hydroxyphosphate salts. A typical adjuvant is amorphous aluminum hydroxyphosphate with $PO_4/Al$ molar ratio between 0.84 and 0.92. The aluminum phosphate will generally be particulate (e.g., plate-like morphology as seen in transmission electron micrographs). Typical diameters of the particles are in the range 0.5-20 µm (e.g. about 5-10 µm) after any antigen adsorption.

The concentration of aluminum salt in an adjuvant composition described herein may be <10 mg/ml e.g. <5 mg/ml, <4 mg/ml, <3 mg/ml, <2 mg/ml, <1 mg/ml, etc. In certain embodiments, the aluminum salt concentration may range is between 0.3 and 1 mg/ml.

In certain embodiments, mixture of both an aluminum hydroxide and an aluminum phosphate, or magnesium phosphate, may be used. In certain cases, there may be more aluminum phosphate than hydroxide, e.g., a weight ratio of at least 2:1, e.g., >5:1, >6:1, >7:1, >8:1, >9:1, etc., or vice versa.

Flavonoids

The adjuvant compositions may include one or more flavonoids or derivates, salts or salts of derivatives thereof. Flavonoids (also known as bioflavonoids) are phytochemicals found in fruits and vegetables. Flavonoids are of the following types: Flavones (e.g., apigenin, luteolin), Flavonols (e.g., quercetin, myricetin), Flavanones (e.g., naringenin, hesperidin), Catechins (e.g., epicatechin, catechin, gallate, such as, epigallocatechin, gallocatechin, epicatechin gallate and epigallocatechin gallate), Anthocyanidins/anthocyanins (e.g., cyanidin, pelargonidin), and Isoflavones (e.g., genistein, daidzein).

In a preferred embodiment, the flavonoid is a catechin. In certain embodiments, the adjuvant compositions may include epigallocatechin gallate (EGCG), a form of catechin (polyphenols). In some embodiments, the adjuvant compositions may include a catechin, such as, catechin hydrate. In some embodiments, the catechin is not a multimeric form of catechin.

In certain cases, the adjuvant compositions may include EGCG derivatives, such as those described in U.S. Pat. No. 7,544,816.

In certain embodiments, the adjuvant compositions may include phytochemicals, such as flavonoids, and analogues thereof, such as those described in U.S. Pat. No. 7,601,754.

Tannins

Tannins are a subclass of plant derived polyphenols and have a high binding affinity for proteins. "Tannin" is a general descriptive name for a group of polymeric phenolic substances capable of tanning leather or precipitating gelatin from solution, a property known as astringency. Their molecular weights range from 500 to 3,000, and they are found in almost every plant part: bark, wood, leaves, fruits, and roots. They are divided into two groups, hydrolyzable and condensed tannins. Hydrolyzable tannins are based on gallic acid, usually as multiple esters with D-glucose, while the more numerous condensed tannins (often called proanthocyanidins) are derived from flavonoid monomers. Tannins may be formed by condensations of flavan derivatives which have been transported to woody tissues of plants. Alternatively, tannins may be formed by polymerization of quinone units. One of the molecular actions of tananins is to complex with proteins through so-called nonspecific forces such as hydrogen bonding and hydrophobic effects, as well as by covalent bond formation. Thus, their mode of antimicrobial action may be related to their ability to inactivate microbial adhesins, enzymes, cell envelope transport proteins, etc. They also complex with polysaccharide. The antimicrobial significance of this particular activity has not been explored (Clinical Microbiology Reviews; October 1999, vol. 12; p. 564-582). Variable immune responses to tannins has stunted research into the properties of these plant metabolites. Increasing evidence demonstrates select binding affinities of individual tannin species that explains, in part, the discrepancies in immunological function. Gamma-delta TCR+T cells can be activated by a select group of tannins called procyanidins (also called condensed tannins) (Crit Rev Immunol. 2008; 28(5):377-402. Response of gammadelta T Cells to plant-derived tannins. Holderness J, Hedges J F, Daughenbaugh K, Kimmel E, Graff J, Freedman B, Jutila M A). Structurally, tannins are divided into gallotannins, Ellagitannins, complex tannins, and condensed tannins. (1) Gallotannins are all those tannins in which galloyl units or their meta-depsidic derivatives are bound to diverse polyol-, catechin-, or triterpenoid units. (2) Ellagitannins are those tannins in which at least two galloyl units are C—C coupled to each other, and do not contain a glycosidically linked catechin unit. (3) Complex tannins are tannins in which a catechin unit is bound glycosidically to a gallotannin or an ellagitannin unit. (4) Condensed tannins are all oligomeric and polymeric proanthocyanidins formed by linkage of C-4 of one catechin with C-8 or C-6 of the next monomeric catechin. Tannin examples include but are not limited to: tannic acid, gallica acid, (−)-Epigallocatechin gallate (EGCG), (−)-epicatechin gallate (ECG), Resveratrol, piceatannol, geraniin, pedunculagin and corilagin. Acertannin, Hamamelitannin, (*Nat. Prod. Rep.,* 2001, 18, 641-649).

Vitamins

The adjuvant compositions also include one or more vitamins, pro-vitamins, or vitamin derivatives, salts or salts of derivatives thereof. The one or more vitamins may be one or more of Vitamin A, Vitamin E, Vitamin D, Vitamin C and Vitamin B, vitamin K, and derivatives and salts thereof.

Vitamin A is a fat-soluble vitamin that is derived from two sources: preformed retinoids and provitamin carotenoids. Retinoids, such as retinal and retinoic acid, are found in animal sources like liver, kidney, eggs, and dairy produce. Carotenoids like beta-carotene (which has the highest vitamin A activity) are found in plants such as dark or yellow vegetables and carrots. Vitamin A is also known as retinol, retinoic acid, Axerophthol, Vitamin A alcohol, Vitamin A1, all-trans-3,7-Dimethyl-9-(2,6,6-trimethyl-1-cyclohexen-1-yl)-2,4,6,8-nonatetraen-1-ol. In certain cases, an acid derivation of Vitamin A, all-trans retinoic acid (ATRA), may be included in the adjuvant compositions. In certain cases, the adjuvant compositions may include retinoids, for example, isotretinoin (Ro 4-3780), etretinate (RO 10-9359; a synthetic retinoid), retinyl palmitate, or motretinide (Ro 11-1430). In certain cases, vitamin A palmitate (VA) may be included in the adjuvant compositions.

Vitamin E is also a fat-soluble vitamin. Of the eight natural substances exerting Vitamin E activity ($\alpha$-, $\beta$-, $\delta$-, and $\gamma$-tocopherols and $\alpha$-, $\beta$-, $\delta$-, and $\gamma$-tocotrienols), $\alpha$-tocopherol ($\alpha$-T) has traditionally been regarded as the most important vitamin because it exerts the highest biological activity of all vitamins when assessed in animal model systems. Vitamin E is also synonymous with ($\pm$)-$\alpha$-Tocopherol and DL-all-rac-$\alpha$-Tocopherol, 5, 7, 8-Trimethyltocol, D-$\alpha$-Tocopherol, 2,5,7,8-Tetramethyl-2-(4',8',12'-trimethyltridecyl)-6-chromanol, and a non-oxidizing version (+)-$\alpha$-Tocopherol acetate and the related all-rac-$\alpha$-Tocopheryl acetate. A related molecule is D-$\alpha$-Tocopherol succinate, Vitamin E succinate.

In certain embodiments, the vitamin E included in the adjuvant compositions may be $\alpha$-tocopherol ($\alpha$-T). In other cases, a Vitamin E analog, such as $\alpha$-tocopheryl succinate (alpha-TOS) may be included in the adjuvant compositions.

Vitamin D is a group of fat-soluble prohormones, the two major forms of which are vitamin $D_2$ (or ergocalciferol) and Vitamin $D_3$ (or cholecalciferol). Vitamin D obtained from sun exposure, food, and supplements, is biologically inert and must undergo two hydroxylation reactions to be activated in the body. Calcitriol (1, 25-Dihydroxycholecalciferol) is the active form of Vitamin D found in the body. The term Vitamin D refers to these metabolites and other analogues of these substances. In certain embodiments, the adjuvant compositions may include 1,25-Dihydroxyvitamin $D_3$ (DHV$D_3$).

Vitamin C is a water-soluble vitamin. Vitamin C or L-ascorbic acid is an essential nutrient for humans. Ascorbate (an ion of ascorbic acid) is required for a range of essential metabolic reactions in all animals and plants. The pharmacophore of Vitamin C is the ascorbate ion. In living organisms, ascorbate is an anti-oxidant, since it protects the body against oxidative stress, and is a cofactor in several vital enzymatic reactions. Vitamin C is purely the L-enantiomer of ascorbate; the opposite D-enantiomer has no physiological significance.

Vitamin B is a water soluble vitamin complex. In certain embodiments, the Vitamin B is Vitamin $B_9$ (folic acid).

Additives

In certain embodiments, the vegetable oil carrier of the adjuvant composition may include allyl isothiocyanate (AIT), as an additive at the preferred dose of 01-2% of the final dose volume. Allyl isothiocyanate (AIT) is also referred to as volatile oil of mustard or essential oil of mustard or oil of mustard. AIT is an organosulfur compound of the formula $CH_2CHCH_2NCS$. AIT is responsible for the pungent taste of mustard, horseradish, and wasabi. It is slightly soluble in water, but well soluble in most organic solvents. Allyl isothiocyanate comes from the seeds of black or brown Indian mustard. When these mustard seeds are broken, the enzyme myrosinase is released and acts on a glucosinolate known as sinigrin to give allyl isothiocyanate. Allyl isothiocyanate serves the plant as a defense against herbivores; since it is harmful to the plant itself, it is stored in the harmless form of the glucosinolate, separate from the myrosinase enzyme. When an animal chews the plant, the allyl isothiocyanate is released, repelling the animal. Allyl isothiocyanate is produced commercially by the reaction of allyl chloride and potassium thiocyanate: $CH_2$=$CHCH_2Cl$+ $KSCN \rightarrow CH_2$=$CHCH_2NCS$+$KCl$. The product obtained in this fashion is sometimes known as synthetic mustard oil. Allyl isothiocyanate can also be liberated by dry distillation of the seeds. The product obtained in this fashion is known as volatile oil of mustard and is usually around 92% pure. It is used principally as a flavoring agent in foods. Synthetic allyl isothiocyanate is used as an insecticide, bacterialcide, and nematocide, and is used in certain cases for crop protection.

In certain cases, particularly where the desired route of administration is mucosal, the adjuvant composition may comprise, a pharmaceutically acceptable carrier, AIT, at least one flavonoid and at least one a vitamin.

The adjuvant compositions may include saponin and its derivative QS-21.

Derivatives of phytol, a dietary diterpene alcohol, similar in structure to naturally occurring isoprenoid adjuvants, elicit increased titers of all major IgG subclasses, especially IgG2a and cytotoxic effector T cell responses. Accordingly, the adjuvant compositions may include phytol or its derivates. However, in certain embodiments it may be preferred to not include phytol.

The adjuvant compositions may include other additives or carriers, such as, gelatin, antibiotics, sorbitol, sucrose, lactose, other sugars, bioadhesives, mucoadhesives (e.g., hyaluronic acid or a derivatie thereof, for example, HYAFF), hydrophilic polymers and hydrogels, polyethylene oxide homopolymers, chitosan, Beeswax, and the like.

The adjuvant compositions may further include immunogenicity enhancing agents, such as, lipopolysaccharides, enterotoxins such as the heat labile toxin from *Escherichia coli* bacterium, cholera toxin from *Vibrio cholerae*, toll like receptor agonists (e.g., CpG or CpG oligonucleotides).

The adjuvant compositions may be combined with other delivery systems, such as, alum, liposomes, virosomes, oil-in-water emulsions, for example.

The adjuvant compositions may be formualted with large, slowly metabolized macromolecules such as proteins, polysaccharides, polylactic acids, polyglycolic acids, polymeric amino acids, amino acid copolymers, and inactive virus particles. Examples of particulate carriers include those derived from polymethyl methacrylate polymers, as well as microparticles derived from poly(lactides) and poly(lactide co glycolides), known as PLG.

The adjuvant compositions may include The mutant forms of a holotoxin, e.g. from *E. coli*, comprising the mutated A subunit and the B subunit, which may be oligomeric, as in the wild-type holotoxin. The B subunit is preferably not mutated. However, it is envisaged that a mutated A subunit may be used in isolation from the B subunit, either in an essentially pure form or complexed with other agents, which may replace the B subunit and/or its functional contribution. LT mutants for use in the compositions include mutants with one or more of the following mutations: a mutation in the A subunit of the serine at position 63, and a mutation in the A subunit of the alanine at position 72, for example, the serine at position 63 is replaced with a lysine and the alanine at position 72 is replaced with arginine.

The adjuvant compositions may include cholera toxin ("CT") or detoxified mutants thereof and microparticles (i.e., a particle of about 100 nm to about 150 µm in diameter, more preferably about 200 nm to about 30 µm in diameter, and still more preferably about 500 nm to about 10 µm in diameter) formed from materials that are biodegradable and non-toxic (e.g., a poly(.alpha.-hydroxy acid), a polyhydroxybutyric acid, a polyorthoester, a polyanhydride, a polycaprolactone, etc.).

The adjuvant compsotions disclosed herein may be formulated as microparticles using a poly(α-hydroxy acid), in particular, from a poly(lactide) ("PLA"), a copolymer of D,L-lactide and glycolide or glycolic acid, such as a poly (D,L-lactide-co-glycolide) ("PLG" or "PLGA"), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the coad-ministered antigen. If the composition includes an antigen, the antigen may be entrapped within the microparticles, or may be adsorbed onto their surface.

In certain embodiments, the compositions disclosed herein include, an immuno-modulatory factor, for example, a protein that is capable of modulating an immune response. Non-limiting examples of immunomodulatory factors include lymphokines (also known as cytokines), such as IL-6, TGF-beta, IL-1, IL-2, IL-3, etc.); and chemokines (e.g., secreted proteins such as macrophage inhibiting factor, RANTES, macrophage inflammatory 1 alpha (MIP1-alpha), etc.). Certain cytokines, for example TRANCE, flt-3L, and a secreted form of CD40L are capable of enhancing the immunostimulatory capacity of APCs. Non-limiting examples of cytokines which may be used alone or in combination in the compositions disclosed herein include, interleukin-2 (IL-2), stem cell factor (SCF), interleukin 3 (IL-3), interleukin 6 (IL-6), interleukin 12 (IL-12), G-CSF, granulocyte macrophage-colony stimulating factor (GM-CSF), interleukin-1 alpha (IL-1 alpha), interleukin-11 (IL-11), MIP-1 gamma, leukemia inhibitory factor (LIF), c-kit ligand, thrombopoietin (TPO), CD40 ligand (CD40L), tumor necrosis factor-related activation-induced cytokine (TRANCE) and flt3 ligand (flt-3L).

In certain embodiments, where the pharmaceutically acceptable carrier is oil-based and the composition comprises an oil based emulsion. In such embodiments, the oil-based emulsion may not include organic phosphates, such as those used in phosphate buffered saline (PBS).

In certain embodiments, the oil-based emulsion may not include ethanol or other alcohols and no quaternary ammonium compounds, such as those selected from the group consisting of Alkyl dimethyl benzyl ammonium chloride, dialkyl dimethyl ammonium chloride, n-Alkyl dimethyl benzyl ammonium chloride, and n-Alkyl dimethyl ethylbenzyl ammonium chloride.

In certain embodiments, the oil-based emulsion may not include cationic halogen containing compounds selected from the group consisting of cetylpyridinium halides, cetyltrimethylammonium halides, cetyldimethylethylammonium halides, cetyldimethylbenzylammonium halides, cetyltributylphosphonium halides, dodecyltrimethylammonium halides, and tetradecyltrimethylammonium halides.

The adjuvant compositions may further include emulsifiers, such as, lecithin, for example phospholipids and/or surfactants that are amphiphilic and acceptable for human and/or veterinary use.

Surfactants are well known to the skilled artisan, and include, interalia, ionic surfactants (e.g. Tween 80), cationic surfactants (e.g. CTAB) or zwitterionic surfactants (e.g. CHAPS). The acceptability of a surfactant for human and/or veterinary use may be determined by those of skill in the art. A surfactant is amphiphilic if a part of the surfactant molecule is hydrophobic and a part is hydrophilic. Examples of surfactants useful in the adjuvant compositions disclosed herein include, but are not limited to, a Tween surfactant and a Span surfactant. Tween and Span surfactants include, but are not limited to, monolaureate (Tween 20, Tween 21, Span 20), monopalmitate (Tween 40, Span 40), monostearate (Tween 60, Tween 61, Span 60), tristearate (Tween 65, Span 65), monooleate (Tween 80, Tween 81, Span 80) and tri-oleate (Tween 85, Span 85).

The adjuvant compositions may include pharmaceutically acceptable auxiliary substances as required to approximate physiological conditions such as pH adjusting and buffering agents, and the like, for example, sodium acetate, sodium chloride, potassium chloride, calcium chloride, sodium lactate, phosphate buffer saline, and the like.

The adjuvant compositions may include medicinal rubefacients, such as, Capsaicin (derived from Cayenne, *Capsicum minimum*), Salicylates (such as Oil of Wintergreen, *Methyl Salicylate*), Nicotinate esters, Rubbing alcohol, common herbal rubefacients include: Cloves (*Eugenia caryphyllus*), Garlic (*Allium sativum*), Ginger (*Zingiber officinale*), Horseradish (*Cochlearia armoracia*), Mustard (e.g., *Brassica alba* or *B. nigra*), Nettle (*Urtica dioica*), Rosemary Oil (*Rosmarinus officinalis*), Rue (*Ruta graveolens*).

Antigens

The adjuvant compositions disclosed herein may be administered in combination with one or more antigen components. Any antigen against which it is desirable to induce an immune response may be used. Such an antigen component may be obtainable from virus, fungi, or bacteria or other human and/or animal pathogens, or cancer cells. The antigen component may be an allergen. Full length protein or a fragment thereof, as well as modified or unmodified protein, may be used as an antigen component. Antigen components also include polysaccharides. In some cases, the antigen component may be a DNA or RNA that codes for an antigen, e.g., DNA or RNA derived from a pathogen or cancer cells.

Many human cancers express cell surface molecule that are specific to the cancer cell, i.e., they are not expressed at a detectable level or a significant level by normal human somatic cells. Examples of such antigens include but are not limited to the following: various glycolipids and polysaccharides, Alpha-fetoprotein (AFP) and Cancer Antigens CA125, CA15-3, and CA19-9.

AFP: Elevation of serum AFP to abnormally high values occurs in several malignant diseases—including nonseminomatous testicular cancer and primary hepatocellular carcinoma—and some benign ones, including hepatitis and cirrhosis.

CA125: Cancer Antigen 125 (CA125) is a surface antigen associated with epithelial ovarian cancer, and to date CA125 is the most sensitive marker for residual epithelial ovarian cancer. CA125 may also be elevated in patients with lung, cervical, fallopian tube, and uterine cancer and endometriosis.

CA15-3: Cancer antigen 15-3 (CA15-3) is useful for monitoring breast cancer patients post-operatively for recurrence, particularly metastatic diseases. CA15-3 has been shown to be useful in early detection of relapse of ovarian cancer. CA15-3 levels are also increased in colon, lung, and hepatic tumors.

CA19-9: Serum CA19-9 level is frequently elevated in subjects with certain gastrointestinal malignancies, such as pancreatic, colorectal, gastric and hepatic carcinomas. A persistently rising serum CA 19-9 value may be associated with progressive malignant disease and poor therapeutic response. A declining CA 19-9 value may be indicative of a favorable prognosis and good response to treatment.

Transmissible spongiform encephalopathies (TSEs) are a group of neurodegenerative diseases characterized by a rapidly progressive deterioration (in cognitive function and/or coordination) which always leads to death. TSEs occur in humans and in animals. The most likely cause of the TSEs is the prion protein form designated PrPSc, named after scrapie, the oldest known form of prion disease, which originated in sheep and goats. How prions cause brain damage is unclear at present, but all hypotheses suggest that posttranslational modification of the native prion protein (PrPC) by PrPSc to form amyloid fibrils is a central event in pathogenesis.

In humans, Creutzfeldt-Jakob disease (CJD) is the most widespread TSE (incidence 1/million/year). Clinically, patients can be diagnosed as possible or probable CJD patients but neuropathological conformation is necessary to obtain a definite diagnosis. Neuropathological investigation is based on a triad of histological lesions: spongiosis, neuron loss, and reactive astrogliosis.

The prion protein (PrP) was initially described as an essential component of the infectious agents responsible for transmissible spongiform encephalopathies (TSE). TSE are a group of neurodegenerative disorders that include Creutzfeldt-Jakob disease and kuru in humans, bovine spongiform encephalopathy, sheep scrapie, and chronic wasting disease in deer and elk. Although the pathophysiology of TSE remains poorly understood, an almost invariable feature is the accumulation of an abnormal isoform of PrP (scrapie PrP, designated PrPSc) in infected tissues of affected individuals. PrP was found to be encoded by a unique gene of the host, Prnp (PRNP in humans), the structure of which is remarkably conserved between species. Its physiological product is expressed as a GPI-anchored membrane protein termed cellular PrP (PrPC), in many tissues at variable levels.

The antigen components for use in combination with the adjuvant compositions described herein include antigen components derived from any pathogens including viruses, bacteria or fungi, or cancers. Such antigen components include, for instance, the structural as well as nonstructural proteins of a pathogen, such as Env, Gag and Pol of HIV or F protein of RSV, or HA of influenza, in their native form or in a form optimized for enhanced immunogenicity.

Other antigen components which may be included in the adjuvant compositions are: A protein antigen from *N. meningitidis* serogroup B, such as those in International patent application publications: WO99/24578; WO99/36544; WO99/57280; WO00/22430; and WO96/29412, for example; an outer membrane vesicle (OMV) preparation from *N. meningitidis* serogroup B, such as those disclosed in. International patent application WO0152885; an oligosaccharide antigen from *N. meninigitidis* serogroup A, C, W135 and/or Y; A saccharide antigen from *Streptococcus pneumoniae*, an antigen from hepatitis A virus, such as inactivated virus, an antigen from hepatitis B virus, such as the surface and/or core antigens, an antigen from hepatitis C virus, *Bordetella pertussis*, such as pertussis holotoxin (PT) and filamentous haemagglutinin (FHA) from *B. pertussis*, optionally also in combination with pertactin and/or agglutinogens 2, a diphtheria antigen, such as a diphtheria toxoid, a tetanus antigen, such as a tetanus toxoid, a saccharide antigen from *Haemophilus influenzae* B, an antigen from *N. gonorrhoeae*) e.g. International patent application publication WO99/24578; WO99/36544; WO99/57280). Other antigens of interest include antigens from: *Chlamydia pneumoniae* (e.g. International patent application WO0202606; International patent application publications: WO99/27105; WO00/27994; WO00/37494), *Chlamydia trachomatis* (e.g. International patent application WO99/28475), *Porphyromonas gingivalis*, polio antigen(s) such as IPV or OPV, rabies antigen(s) such as lyophilised inactivated virus (e.g. 77, RabAvert™), measles, mumps and/or rubella antigens, influenza antigen(s), such as the haemagglutinin and/or neuraminidase surface proteins, the Respiratory syncytial virus, e.g. the F or the G proteins, the caliciviridae family of viruses, e.g. norovirus and sapovirus, the reoviridae family, e.g. Rotavirus, herpes simplex viruses, prions, the *Salmonella* bacteria, *Escherichia coli* bacteria, the *Vibrio cholera* bacteria, *Moraxella catarrhalis*, *Streptococcus agalactiae* (group B *streptococcus*) [e.g. International patent application PCT/GB01/04789], *Streptococcus pyogenes* (group A *streptococcus*) [e.g. International patent application PCT/GB01/04789], *Staphlylococcus aureus*, the Respiratory syncytial virus, e.g. the F or the G proteins, the caliciviridae family of viruses, e.g. norovirus and sapovirus, the reoviridae family, e.g. Rotavirus, herpes simplex viruses, *Salmonella* bacteria.

A saccharide or carbohydrate antigen component may be conjugated to a carrier protein Exemplary carrier proteins are bacterial toxins or toxoids, such as diphtheria, cholera, *E. coli* heat labile or tetanus toxoids, CRM.sub.197 diphtheria toxoid, *N. meninigitidis* outer membrane protein [European patent application 0372501], synthetic peptides [European patent applications 0378881 & 0427347], heat shock proteins [International patent application WO93/17712], pertussis proteins [International patent application WO98/58668; see also EP 04711771, protein D from *H. influenzae* [International patent application WO00/56360], toxin A or B from *C. difficile* [International patent application WO00/61761], for example. Any suitable conjugation reaction can be used, with any suitable linker where necessary.

The immunomodulatory/adjuvant compositions disclosed may include an antigen component that is a nucleic acid which encodes a polypeptide antigen or a protein antigen as described above. Examples of nucleic acid antigen components that can be provided as DNA or RNA-based vaccines and vector vaccines include vaccines for HIV, herpes, hepatitis and influenza.

Examples of Compositions

Exemplary compositions are provided in Table 1 below.

TABLE 1

| Adjuvant Comp | Oil Carrier | Flavonoid and/or tannins | Vitamin |
|---|---|---|---|
| 1 | Mustard Oil (+/− AIT) | Catechin hydrate and/or gallic acid | VA |
| 2 | Mustard Oil (+/− AIT) | Catechin hydrate and/or gallic acid | VE |

TABLE 1-continued

| Adjuvant Comp | Oil Carrier | Flavonoid and/or tannins | Vitamin |
|---|---|---|---|
| 3 | Mustard Oil (+/− AIT) | Catechin hydrate and/or gallic acid | VC |
| 4 | Mustard Oil (+/− AIT) | Catechin hydrate and/or gallic acid | VD |
| 5 | Mustard Oil (+/− AIT) | Catechin hydrate and/or gallic acid | VA + VE |
| 6 | Mustard Oil (+/− AIT) | Catechin hydrate and/or gallic acid | VA + VD |
| 7 | Mustard Oil (+/− AIT) | Catechin hydrate and/or gallic acid | — |
| 8 | Mustard Oil (+/− AIT) | — | VA |
| 9 | Mustard Oil (+/− AIT) | — | VE |
| 10 | Mustard Oil (+/− AIT) | — | VC |
| 11 | Mustard Oil (+/− AIT) | — | VD |
| 12 | Mustard Oil (+/− AIT) | — | VA + VE |
| 13 | Mustard Oil (+/− AIT) | — | VA + VD |
| 14 | Olive Oil (+/− AIT) | Catechin hydrate and/or gallic acid | VA |
| 15 | Olive Oil (+/− AIT) | Catechin hydrate and/or gallic acid | VE |
| 16 | Olive Oil (+/− AIT) | Catechin hydrate and/or gallic acid | VC |
| 17 | Olive Oil (+/− AIT) | Catechin hydrate and/or gallic acid | VD |
| 18 | Olive Oil (+/− AIT) | Catechin hydrate and/or gallic acid | VA + VE |
| 19 | Olive Oil (+/− AIT) | Catechin hydrate and/or gallic acid | — |
| 20 | Olive Oil (+/− AIT) | Catechin hydrate and/or gallic acid | VA + VD |
| 21 | Olive Oil (+/− AIT) | — | VA |
| 22 | Olive Oil (+/− AIT) | — | VE |
| 23 | Olive Oil (+/− AIT) | — | VC |
| 24 | Olive Oil (+/− AIT) | — | VD |
| 25 | Olive Oil (+/− AIT) | — | VA + VE |
| 26 | Olive Oil (+/− AIT) | — | VA + VE |

The adjuvant compositions 1-26 described above are exemplary and may include additional components, such as, an additional oil carrier, e.g., sunflower seed oil, coconut oil, soybean oil. In other embodiments, compositions 1-26 described above do not contain additional oil carriers, e.g., sunflower oil, coconut oil, soybean oil.

The adjuvant compositions 1-26 described in Table 1 as well as other adjuvant compositions described in the specification may include additional components, such as, additives, e.g., antigens, preservatives, colorants, flavorants, buffers, salts, etc.

Components of the Adjuvant Compositions and their Relative Amounts

The adjuvant compositions described herein may be used to induce an immune response, such as, a Th-1 response. Th-1 response may be particularly suited to respond to viral infections, intracellular pathogens, and tumor cells because it includes IL-2 and IFN-α, which activate CTLs.

The adjuvant compositions described herein may be used to induce an immune response, such as, a Th-2 response. Th-2 response may be more suited to respond to extracellular bacteria and helminthic parasites and may also mediate allergic reactions, since IL-4 and IL-5 are known to induce IgE production and eosinophil activation.

Vitamin A (e.g., All-trans retinoic acid (ATRA), an acid derivation of Vitamin A) may be included in the adjuvant compositions if a higher Th-2 response is desired. In certain cases, it may be desirable to elicit a Th-1 type immune response. In these cases, the adjuvant compositions may include a pharmaceutically acceptable carrier, Vitamin C (e.g., ascorbate) and/or Vitamin D and/or Vitamin E and a flavonoid, and/or a tannin, e.g. gallic acid.

The adjuvant composition may include a pharmaceutically acceptable carrier and: a flavonoid and Vitamin A; or a flavonoid, Vitamin C and Vitamin A; or a flavonoid, Vitamin D and Vitamin A; or a flavonoid, Vitamin E and Vitamin A; or a flavonoid, Vitamin C and E and Vitamin A; or a flavonoid, Vitamin C and D and Vitamin A; or a flavonoid, Vitamin D and E and Vitamin A in the adjuvant compositions. It is understood that each of the foregoing compositions may include the vitamin named or a salt or derivative thereof. Similarly, the flavonoid may be a flavonoid or a salt or derivative thereof.

In certain embodiments, the inclusion of a pharmaceutically acceptable carrier (e.g., fish oil or mustard oil), a flavonoid, and a vitamin (such as, Vitamin A, C, D and/or E) in the adjuvant compositions may produce an enhanced immune response (for example, a synergistic effect) compared to the effect of an adjuvant composition that includes a pharmaceutically acceptable carrier (e.g., mustard oil) and a flavonoid or a pharmaceutically acceptable carrier (e.g., mustard oil) and a vitamin (such as, Vitamin A, C, D and/or E).

The adjuvant compositions disclosed herein may include fish oil or mustard oil or another pharmaceutically acceptable oil carrier. Pharmaceutically acceptable oil carrier with rubefacient properties, for example mustard oil, is suitable for preparation of adjuvant compositions for administration through epithelial cells of the mucosal membranes or the skin or directly injected by e.g. intra-muscular or intra-dermal administrations. When the route of administration is a mucosal route, compositions comprising allyl isothiocyanate are believed to be particularly preferred.

The volume of pharmaceutically acceptable oil carrier, e.g., fish oil, oleic acid and/or mustard oil, used in liquid form in the adjuvant compositions described herein may be in the range of 1-95% of the total volume of an adjuvant composition. Thus, in certain cases, the pharmaceutically acceptable oil carrier may make up at least about 1%, at least about 5%, at least about 10%, at least about 20%, at least about 30%, at least about 40%, at least about 50%, at least about 60%, at least about 70%, at least about 80%, at least about 90%, or at least about 95% by volume of the total volume of a subject adjuvant composition. In certain embodiments, the pharmaceutically acceptable oil, such as MO, comprises from about 1% to about 95% v/v of the compositions of the invention, more preferably from about 5% to 90%, 10% to 75%, 10% to 50%, 50% to 75%, 50% to 90% v/v of the composition. In a particularly preferred embodiment, the composition is capable of enhancing an immune response and comprises from about 50% to 75% MO, and more preferably 50% or 75% MO. In a further preferred embodiment, the composition is capable of suppressing an immune response and comprises from about 10% MO. In a further preferred embodiment, the composition comprises from about 10% to about 50% oleic acid, and more preferably about 40% oleic acid.

The volume of pharmaceutically acceptable carrier, e.g., Alum, may be in the range of from about 1% to about 75% of the total volume of the adjuvant composition and more preferably from about 2.5% to about 50% of the total volume. In particularly preferred embodiments the composition comprises 2.5% or 50% Alum.

The amount of a vitamin (or its salt or derivative) that may be included in the subject adjuvant compositions may be determined based on the body weight of the subject. In general, the recommended daily allowance may be used to ascertain the amount of vitamin that may be present in the subject adjuvant compositions.

For example, the amount of Vitamin A that may be included in the subject adjuvant compositions may be in the range of 1-250 μg/kg body weight, e.g., 1 μg/kg, 5 μg/kg, 10 μg/kg, 20 μg/kg, 30 μg/kg, 50 μg/kg, 70 μg/kg, 90 μg/kg, 110 μg/kg, 130 μg/kg, 150 μg/kg, 170 μg/kg, 190 μg/kg, 210 μg/kg, 230 μg/kg, or 250 μg/kg body weight.

For example, the amount of Vitamin C that may be included in the subject adjuvant compositions may be in the range of 1-100 mg/kg body weight, e.g., 1, 5, 10, 15, 30, 50, 70, 80, 90, or 100 mg/kg body weight.

For example, the amount of Vitamin D that may be included in the subject adjuvant compositions may be in the range of 0.01-10 μg/kg body weight, e.g., 0.01, 0.5, 1, 2, 5, 7, 8, 9, or 10 μg/kg body weight.

For example, the amount of Vitamin E that may be included in the subject adjuvant compositions may be in the range of 0.01-10 mg/kg body weight, e.g., 0.01, 0.05, 0.1, 0.5, 1, 2, 5, 7, 8, 9, or 10 mg/kg body weight.

The amount of a flavonoid (or its salt or derivative) that may be included in the subject adjuvant compositions may be determined based on the body weight of the subject. The amount of the flavonoid, e.g., catechin (such as catechin hydrate), may be in the range of 1-100 mg/kg body weight of a subject, e.g., 1, 5, 10, 15, 30, 50, 70, 80, 90, or 100 mg/kg body weight.

The amount of a tannin (or its salt or derivative) that may be included in the subject adjuvant compositions may be determined based on the body weight of the subject. The amount of the flavonoid, e.g., catechin (such as catechin hydrate), may be in the range of 1-100 mg/kg body weight of a subject, e.g., 1, 5, 10, 15, 30, 50, 70, 80, 90, or 100 mg/kg body weight.

The adjuvant compositions may be in the form of a suspension, tablet (to be swallowed or chewed), fast-dissolving tablets or gels or strips, capsule, powder, gel, cream, lotion, ointment, aerosol or the like.

An exemplary adjuvant composition for administration to a human subject may include 3-80% vol/vol of oil, e.g., at least about 3%, at least about 10%, at least about 15%, at least about 20%, at least about 25%, at least about 30%, at least about 40%, at least about 50%, at least about 60%, at least about 70%, or at least about 80% vol/vol of oil.

An exemplary adjuvant composition for administration to a human subject may include 0.1-100 mg of Vitamin A, e.g., 0.1, 0.5, 1, 5, 10, 15, 30, 50, 70, 80, 90, or 100 mg of Vitamin A.

An exemplary adjuvant composition for administration to a human subject may include 0.1-400 mg of Vitamin E, e.g., 0.1, 0.5, 1, 5, 10, 15, 30, 50, 70, 80, 90, 100, 200, 300, or 400 mg of Vitamin E.

An exemplary adjuvant composition for administration to a human subject may include 0.1-2000 mg of Vitamin C, e.g., 0.1, 0.5, 1, 10, 30, 100, 130, 200, 300, 600, 900, 1000, 1300, 1500, 1800, or 2000 mg of Vitamin C.

An exemplary adjuvant composition for administration to a human subject may include 0.1-2000 mg of Vitamin B9, e.g., 0.1, 0.5, 1, 10, 30, 100, 130, 200, 300, 600, 900, 1000, 1300, 1500, 1800, or 2000 mg of Vitamin B9

An exemplary adjuvant composition for administration to a human subject may include 0.1-2000 mg of Catechin hydrate or epigallo catechin gallate, e.g., 0.1, 0.5, 1, 10, 30, 100, 130, 200, 300, 600, 900, 1000, 1300, 1500, 1800, or 2000 mg of Catechin hydrate or epigallo catechin gallate.

An exemplary adjuvant composition for administration to a human subject may include 0.001-10 mg of AIT, e.g., 0.001, 0.005, 0.01, 0.05, 0.1, 0.5, 1, 2, 5, 7, 8, 9, or 10 mg of AIT.

As used in herein vol/vol refers to the volume of a component in the total volume of the adjuvant composition.

Th1-type immune response can be induced in mammals by administration of certain immunomodulatory polynucleotides. The immunomodulatory polynucleotides include sequences referred to as immunostimulatory sequences ("ISS"), often including a CG dinucleotide. See, e.g., PCT Publications WO 98/55495, WO 97/28259, U.S. Pat. Nos. 6,194,388 and 6,207,646. Thus, in certain embodiments, the subject adjuvant compositions may include ISS.

In certain embodiments, the subject adjuvant compositions may include an emulsifier (such as, lecithin, or a surfactant, e.g., detergents) as described above. The concentration of an emulsifier in the adjuvant composition is dependent on different factors. For example, the higher the concentration of the pharmaceutically acceptable oil in the adjuvant composition the more emulsifier is required. In general, the concentration of a surfactant or other emulsifier in the subject adjuvant composition is from 1.5% to 5% v/v, or 1.5% to 3% v/v, or 1.5% to 2.5%, or 2% v/v. When more than one surfactant is used, the sum of the concentrations of all surfactants used in the adjuvant composition is also from 1.5% to 5%, or 1.5% to 3%, or 1.5% to 2.5%, or 2% v/v.

The adjuvant compositions disclosed herein may not include an antigen component. An adjuvant composition that does not include an antigen component may be used to generally and non-specifically enhance or suppress immune responses, for example to serve as a general immunopotentiator or immuno-suppressor to be taken daily. Alternatively, an adjuvant composition that does not include an antigen can be administered in conjunction with an antigen, i.e., before, simultaneously, or after vaccinations.

Adjuvant Compositions Including an Antigen Component

In certain embodiments, the subject adjuvant compositions may include one or more antigen components.

The concentration of the antigen component in adjuvant compositions can vary widely, and will be selected primarily based on fluid volumes, viscosities, body weight and the like in accordance with the particular mode of administration selected and the subject's needs. The concentration of an antigen component in the pharmaceutical formulations can vary widely, i.e., from less than about 0.1%, usually at or at least about 2% to as much as 20% to 30% or more by weight/volume, and will be selected primarily by nature of the antigen, fluid volumes, viscosities, etc., in accordance with the particular mode of administration selected. In certain embodiments, the antigen may be 0.1%-30% w/v of the adjuvant composition, for example, 0.1%-25%, 0.5%-20%, 1%-15%, 2%-10%, 3%-8%, or 5%-6% w/v of the adjuvant composition.

Method of Making Adjuvant Composition

Also provided herein are methods of making the adjuvant compositions. The methods comprise admixing a pharmaceutically acceptable carrier, a flavonoid and/or tannin and a vitamin to produce the compositions.

The components of the subject adjuvant composition may be obtained from a variety of sources using a number of methods. Alternatively, the components may be synthesized chemically. In certain cases, the components may be isolated from a natural source and may be additionally modified, e.g., chemically modified. For example, mustard oil may be extracted from mustard plant seeds. Alternatively, the pharmaceutically acceptable vegetable oil or animal oil carrier may be purchased from a vendor. Vitamins A, C, D, and E may be purchased from Sigma Aldrich chemical company, prepared and produced by standard biochemical methods. The flavonoids, e.g., catechins, for example, catechin hydrate, may be purchased from Sigma Aldrich chemical company, prepared and produced by standard biochemical methods.

In general, Catechins may either be extracted from green tea or synthesized chemically. Korean and Chinese green tea, and pu-erh, Indian black, Longjing, Tieguanyin, Bamboo, Jasmine, Oolong, Flower, Red teas may be used for extracting catechins, such as, epigallocatechin, catechin, epicatechin, epigallocatechin gallate and epicatechin gallate. Chinese green tea is a rich source of catechin. Green tea is a better source of catechin compared to the other types of tea.

Vitamin A (e.g., retinoic acid), Vitamin D (e.g., Calcitriol (1,25-Dihydroxycholecalciferol), Vitamin E (e.g., alpha-tocopherol) and catechin hydrate may be dissolved in ethanol, for example, 200 proof ethanol. Vitamin C and Vitamin B may be dissolved in an alkaline solution such as sodium bicarbonate buffer. An antigen may be dissolved in water, a buffer (e.g., PBS), or saline solution. A stock solution of the individual components of the adjuvant composition may be made and the appropriate volumes of the components may then be mixed together to obtain the subject adjuvant composition. The total volume of the subject adjuvant composition may be adjusted with PBS or saline.

In certain embodiments, a pharmaceutically acceptable oil and a falvonoid and/or a tannin and optionally a vitamin may be mixed together in amounts as described above along with a surfactant such as Tween®-80. Before administrating, the adjuvant composition may be emulsified by repeatedly withdrawing and releasing the mixture of a pharmaceutically acceptable oil, a surfactant(s), and another component(s).

In certain embodiments, a pharmaceutically acceptable organic or inorganic carrier may be mixed with watersoluble flavonoids, tannins, and vitamin dervatives.

The components of the adjuvant compositions may be sterilized prior to admixing or after forming the adjuvant compositions. The adjuvant compositions may be mixed with a gel, or formulated into microparticles, etc. before administration.

The adjuvant compositions disclosed herein may be formulated into a spray (e.g., nasal spray), drops (e.g., nasal drops), gel, powder, tablets or capsules, patch, and the like. Of particular interest are adjuvant compositions suitable for administration via inhalation including but not limited to, liquid suspensions for forming aerosols as well as powder forms for dry powder inhalation delivery systems. Devices suitable for administration by inhalation of subject adjuvant composition include, but are not limited to, atomizers, vaporizers, nebulizers, and dry powder inhalation delivery devices.

The adjuvant compositions disclosed herein may be formulated into liquids or emulsions. In the course of the formulation process any type of emulsion may be formed, including without limitation an oil-in-water emulsion, a water-in-oil emulsion, a multiple (e.g. double, tri-multiple, quarter-multiple, etc.) emulsion, and reverse emulsion. The compositions of the present invention may be in the form two phases where one phase is uniformly dispersed in the other phase, resulting in a homogenous macroscopic appearance. Where compositions comprising two or more non-uniformly dispersed phases are formed, the phases may be shaken or stirred prior to use of the emulsion. In certain embodiments, as noted above, oil-in-water emulsions may be produced by use of a high pressure homogenization process, which applies pressures of 500-30000 psi to force the emulsion through a narrow nozzle, resulting in a homogeneous emulsion with droplets/particle sizes of 30-100 nm.

In certain embodiments, the compositions provided herein do not include a solubilizing agent as described in United States Patent Application No. 20080254188. In certain embodiments, the compositions described herein are not water-soluble formulations, rather, they are water insoluble formulations, such as, emulsions. The term water-soluble means that the formulation when added to an aqueous medium (e.g., water) dissolves in the aqueous medium to produce a solution that is essentially clear. In one example, the formulation dissolves in the aqueous medium without heating the resulting mixture above ambient temperature (e.g., 25° C.). Essentially clear means that the composition is transparent and essentially free of visible particles and/or precipitation (e.g., not visibly cloudy, hazy or otherwise non-homogenous).

Method of Using Adjuvant Compositions

The present disclosure provides methods for modulating an immune response in a subject, such as, stimulating or suppressing an innate, cellular and/or a humoral immune response. The adjuvant compositions disclosed herein can be useful for prophylaxis, prevention, and/or treatment of various infections and neoplastic diseases.

Conditions

In certain embodiments, the adjuvant compositions disclosed herein may find use in the context of administering an antigen, such as a vaccine. The vaccine may be a prophylactic/preventative vaccine or a therapeutic vaccine. A prophylactic/preventative vaccine is given before infection to prevent or otherwise protect against the disease, whereas a therapeutic vaccine is given after the onset of infection or disease.

A prophylactic/preventative vaccine comprises one or more epitopes associated with a disorder for which the subject may be at risk (e.g., *M. tuberculosis* antigens as a vaccine for prevention of tuberculosis).

Therapeutic vaccines comprise one or more epitopes associated with a particular disorder affecting the individual, such as *M. tuberculosis* or *M. bovis* surface antigens in tuberculosis patients, antigens to which the individual is allergic (i.e., allergy desensitization therapy) in individuals subject to allergies, tumor cells from an individual with cancer (e.g., as described in U.S. Pat. No. 5,484,596), or tumor associated antigens in cancer patients.

The adjuvant composition may be given in conjunction with the antigen (e.g., in the same composition or a simultaneously using separate compositions) or the adjuvant composition may be administered separately (e.g., at least 12 hours before or after administration of the antigen). In certain embodiments, the antigen(s) is admixed with the adjuvant composition.

Administration of the subject adjuvant composition and antigen may result in amelioration of one or more symptoms or a later onset of one or more symptoms of the disorder which the vaccine is intended to treat. As will be apparent to one of skill in the art, the exact symptoms and manner of their improvement will depend on the disorder sought to be treated. For example, where the therapeutic vaccine is for tuberculosis, administration of adjuvant composition with antigen may result in reduced or delayed onset of coughing, pleural or chest wall pain, fever, and/or other symptoms known in the art. Where the vaccine is an allergen used in allergy desensitization therapy, the administration of adjuvant composition with antigen may result in a reduction or a delay in onset of the symptoms of allergy (e.g., reduction in rhinitis, allergic conjunctivitis, circulating levels of IgE, and/or circulating levels of histamine).

The subject adjuvant composition may also be used prophylactically to increase resistance to infection by a wide range of bacterial or viral pathogens, including natural or genetically modified organisms employed as agents of biological warfare or bio-terrorism.

Other embodiments relate to immunomodulatory therapy of subjects having a pre-existing disease or disorder, such as cancer or an infectious disease. Cancer is an attractive target for immunomodulation because most cancers express tumor-associated and/or tumor specific antigens which are not found on other cells in the body. Stimulation of a Th1-type immune response results in the death of tumor cells, either by direct action of cellular immune system cells (e.g., CTLs) or components of the humoral immune system, or by bystander effects on cells proximal to cells targeted by the immune system including macrophages and natural killer T(NKT) cells.

The adjuvant composition disclosed herein can also be administered to subjects with infectious diseases caused by extracellular pathogens (e.g., bacteria or protozoans) or by intracellular pathogens (e.g., viruses).

In certain embodiment, a subject suffering from a disorder associated with a Th2-type immune response, such as (without limitation) allergies, allergy-induced asthma, atopic dermatitis, eosinophilic gastrointestinal inflammation, eosinophilic esophagitis, and allergic bronchopulmonary aspergillosis may be treated by administering an adjuvant composition disclosed herein. For example, an adjuvant composition comprising a pharmaceutically acceptable oil carrier, a flavonoid and at least one Vitamin C, D and E may be administered to the subject suffering from a disorder associated with a Th2-type immune response increasing levels of one or more Th1-type response associated cytokines, which may result in a reduction of the Th2-type response features associated with the subject's response to the allergen. Immunomodulation of a subject with Th2-type response associated disorders results in a reduction or improvement or delay in the onset of one or more of the symptoms of the disorder. Where the disorder is allergy or allergy-induced asthma, improvement in one or more of the symptoms includes a reduction one or more of the following: rhinitis, allergic conjunctivitis, circulating levels of IgE, circulating levels of histamine and/or requirement for "rescue" inhaler therapy (e.g., inhaled albuterol administered by metered dose inhaler or nebulizer).

Route of Administration

The adjuvant compositions disclosed herein may be administered to a subject via a number of routes of administration. Exemplary routes of administration include mucosal, e.g., oral, sublingual, intra-nasal, inhalation, ocular, intra-vaginal, intra-rectal; and systemic, e.g., intra-muscular, intra-dermal, trans-dermal, intraperitoneal, subcutaneous or trans-cutaneous. In certain embodiments, a combination of at least two routes of administration may be used to induce an immune response. For example, a combination of a mucosal route and a systemic route of administration may be used.

The route of administration may vary based on the individual subject and the stage of the disease and other factors evident to one skilled in the art.

When the route of administration is a mucosal or trans-epithelial (through the skin) route, compositions comprising allyl isothiocyanate are preferred.

In certain embodiments, the adjuvant compositions described herein may be administered through the mucosal surface without breaking the mucosal surface.

The subject adjuvant compositions may be used with or without an antigen(s). When used with an antigen, the adjuvant composition and the antigen may be administered simultaneously or the adjuvant composition may be administered before or after the administration of the antigen. When used with an antigen, the antigen may be mixed with the adjuvant composition.

The adjuvant compositions disclosed herein may be provided as micro- or nano-particles in gel or tablet (such as, fast dissolving) forms. Such formulations may be administered via oral or sublingual routes, for example. For intranasal administration, the adjuvant compositions may be formulated as nasal sprays in an emulsion form or drops, for example. For transcutaneous administration, adjuvant compositions may be given in a gel, lotion or ointment form. For systemic injections, the adjuvant compositions can be given formulated as an emulsion and/or micro/nanoparticles. For rectal administration, the adjuvant compositions can be formulated as suppository or gels, for example. For vaginal administration, the adjuvant compositions formulated as gel, emulsion, ointment, for example.

In certain embodiments, the adjuvant compositions disclosed herein may be administered to a subject via a combination of different routes in the order indicated below:
 i. systemic, mucosal;
 ii. systemic, systemic, mucosal, mucosal;
 iii. systemic, mucosal, systemic;
 iv. mucosal, mucosal, systemic, systemic;
 v. mucosal, systemic, systemic;
 vi. mucosal, systemic, mucosal, for example.

When an adjuvant composition is administered systemically or mucosally more than once, the two or more systemic or mucosal administrations may be by the same systemic (for example, two intramuscular injections) or mucosal route (two intra-nasal (IN)/sublingual (SL) administrations) or different (for example, one intramuscular injection and one intravenous injection; one IN administration and one SL administration).

Dosages

The dosage of the adjuvant compositions described herein to be administered to a subject comprising may be determined based on the route of administration and body weight and may range from 0.001 ml/kg body weight to 1 ml/kg body weight. The number of times an adjuvant composition is administered may vary and may be determined based upon numerous factors. These factors are evident to a person of skill in the art and may include, the disease to be prevented or treated, the type of pathogen or cancer, the structural nature of the antigen, the route of administration, the level of immune response induced in the subject, the type of immune response, etc.

Subjects

The adjuvant compositions described herein may be used to elicit an immune response in a variety of subjects capable of mounting an immune response. In certain cases, the adjuvant compositions described herein may be administered to any member of the subphylum chordata, including, mammals (humans, other non-human primates, domesticated animals, e.g., livestock), avians, fishes, or any other animal in need thereof. In certain cases, the adjuvant compositions may be administered to humans. In certain cases, the adjuvant compositions may be administered to cows. In certain cases, the adjuvant compositions may be administered to chickens, horse, sheep, goats. In certain cases, the adjuvant compositions may be administered to porcines. In certain cases, the adjuvant compositions may be administered to cats and dogs.

Detection of Immune Response

Modulation of an immune response may be humoral and/or cellular, and may be measured using standard techniques in the art. An immune response in a subject can be detected in any number of ways, including measuring expression levels of antigen-specific antibodies, one or more of IFN-gamma, IFN-alpha, IL-2, IL-12, TNF-alpha, IL-6, IL-4, IL-5, IL-10, IL-12, IL-13, IL-15, IL-18, IL-22, and other cytokines as well as detecting responses such as T cell proliferation, activation of specific populations of lymphocytes such as CD4$^+$T cells, NK cells or CTLs, and dendritic cell and macrophage maturation and activation.

Methods for measuring specific antibody responses include enzyme-linked immunosorbent assay (ELISA) and are well known in the art. Measurement of numbers of specific types of lymphocytes such as CD4$^+$T cells can be achieved, for example, with fluorescence-activated cell sorting (FACS). Cytotoxicity and CTL assays can be as described in Raz et al. (1994) Proc. Natl. Acad. Sci. USA 91:9519-9523, for example. Cytokine concentrations can be measured, for example, by ELISA. These and other assays to evaluate the immune response to an immunogen are well known in the art. See, for example, SELECTED METHODS IN CELLULAR IMMUNOLOGY (1980) Mishell and Shiigi, eds., W.H. Freeman and Co.

Kits

Kits that include one or more sterile containers of components of the adjuvant compositions described herein are also provided. Individual components may be present in separate sterile containers or two or more components may be present in a single container. Optionally, the kit may also include a container containing a desired antigen(s).

In some embodiments, the sterile containers may optionally have an access port(s) for withdrawing a specific volume/amount of a component, for example, a port for introducing a syringe to withdraw a certain volume of a pharmaceutically acceptable carrier.

In some embodiments, the containers of the components of the adjuvant compositions described herein may not be sterile but are reasonably clean.

The kits may further include a suitable set of instructions, generally written instructions, relating to the use of the adjuvant composition for immunomodulation (e.g., ameliorating symptoms of an infectious disease, increasing IFN-gamma levels, increasing IFN-alpha levels, or ameliorating an IgE-related disorder).

The kits may comprise the components of the adjuvant composition packaged in any convenient, appropriate packaging. For example, if a component is a dry formulation (e.g., freeze dried or a dry powder), a vial with a resilient stopper may be used, so that the component may be easily resuspended by injecting fluid through the resilient stopper. Ampoules with non-resilient, removable closures (e.g., sealed glass) or resilient stoppers may be used for liquid component(s) of the adjuvant composition. Also contemplated are packages for use in combination with a specific device, mucosal administration devices, such as, an inhaler, nasal administration device (e.g., an atomizer) or eye drops.

The instructions relating to the use of adjuvant composition generally include information as to dosage, dosing schedule, and route of administration for immunomodulation. The containers of containing the components of adjuvant composition or the premixed adjuvant composition may be unit doses, bulk packages (e.g., multi-dose packages) or sub-unit doses. Instructions supplied in the kits disclosed herein are typically written instructions on a label or package insert (e.g., a paper sheet included in the kit), but machine-readable instructions (e.g., instructions carried on a magnetic or optical storage disk) may also be included.

EXAMPLES

Figure 1B:
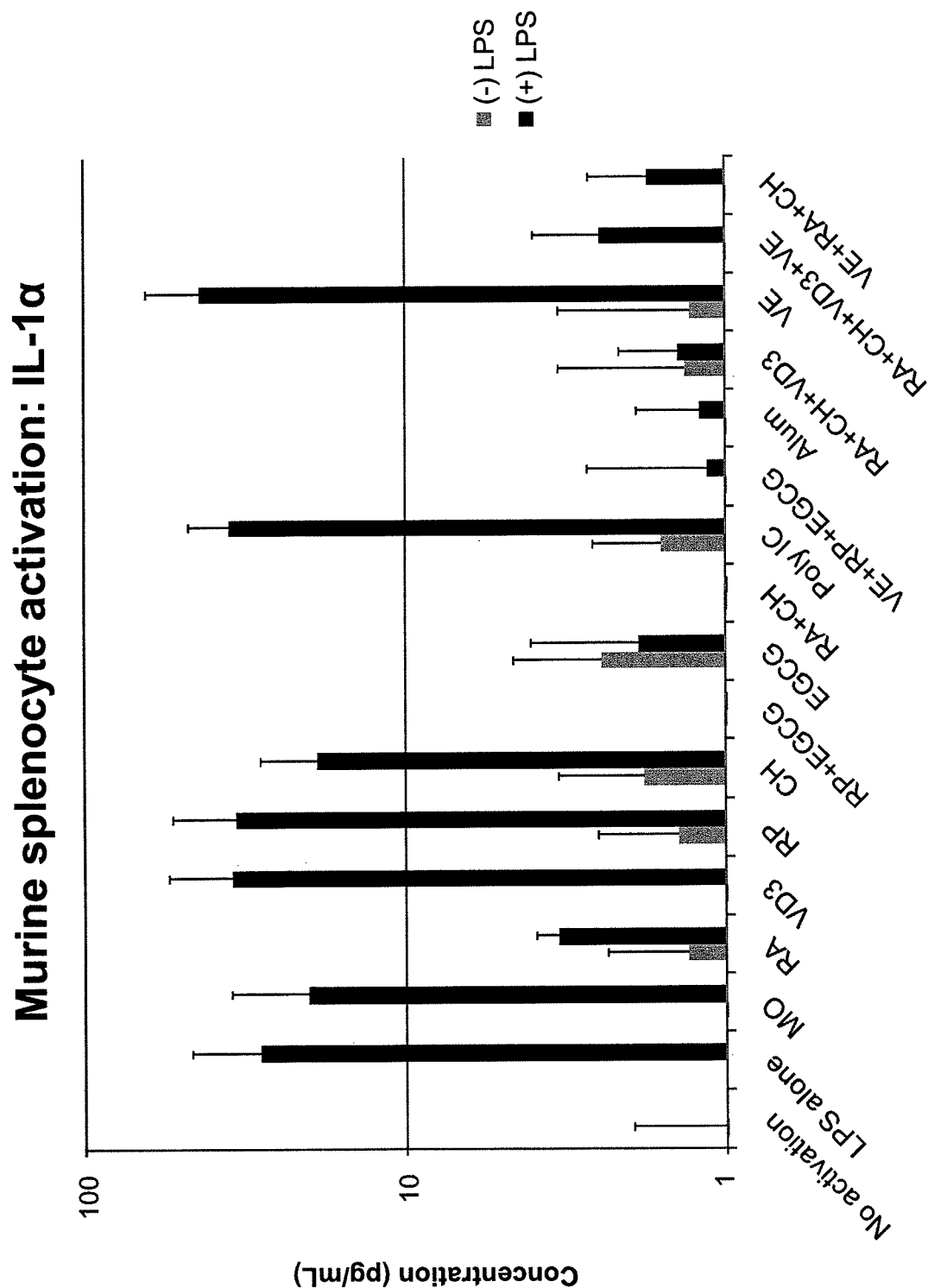
FIG. 1B is a bar graph showing Interleukin 1-alpha production by murine splenocytes following four days of in vitro activation with various components (MO: mustard oil; RA: retinoic acid; VD3: vitamin D3; RP: retinyl palmitate; CH: catechin hydrate; EGCG: epigallo catechin gallate; VE: vitamin E (α-tocopherol)), poly (I:C), alum (imject) or no activation, in the presence or absence of LPS.
Figure 1C:
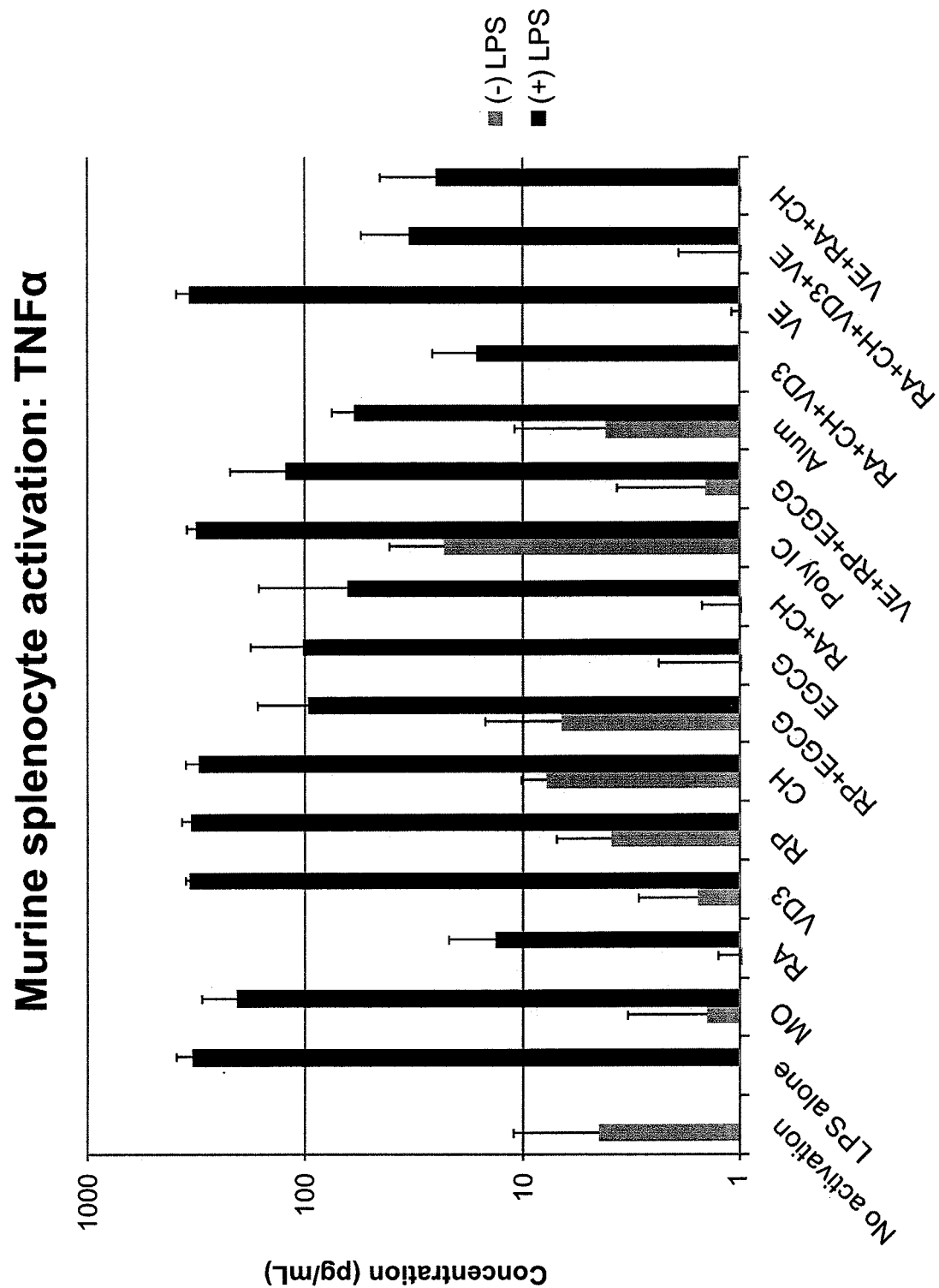
FIG. 1C is a bar graph showing TNF-alpha production by murine splenocytes following four days of in vitro activation with various components (MO: mustard oil; RA: retinoic acid; VD3: vitamin D3; RP: retinyl palmitate; CH: catechin hydrate; EGCG: epigallo catechin gallate; VE: vitamin E (α-tocopherol)), poly (I:C), alum (imject) or no activation, in the presence or absence of LPS.

Example 1: Synergistic Immumodulatory Effect of Vitamin A and a Flavonoid Following Activation of Eukaryotic Cells with Lipopolysaccharide To determine the immonomodulatory roles of the flavonoids, catechin hydrate (CH), epigallo catechin gallate (EGCG), and vitamins, vitamin D3 (VD3), vitamin E (α-tocopherol; VE), retinoic acid (RA; vitamin A derivative) and retinyl palmitate (RP; vitamin A derivative) alone or in combinations in the presence or absence of lipopolysaccharide (LPS), murine spleen cells were activated in vitro for 4 days and culture supernatants were analyzed by ELISA for the presence of IL-6. The combination of RA and CH had a surprisingly synergistic effect on reducing the production of IL-6, and IL-1α in the presence of LPS. (FIGS. 1A and 1B). Moreover, in the absence of LPS activation, the combination of RA and CH synergistically reduced TNFα production (FIG. 1C).

Figure 2A:
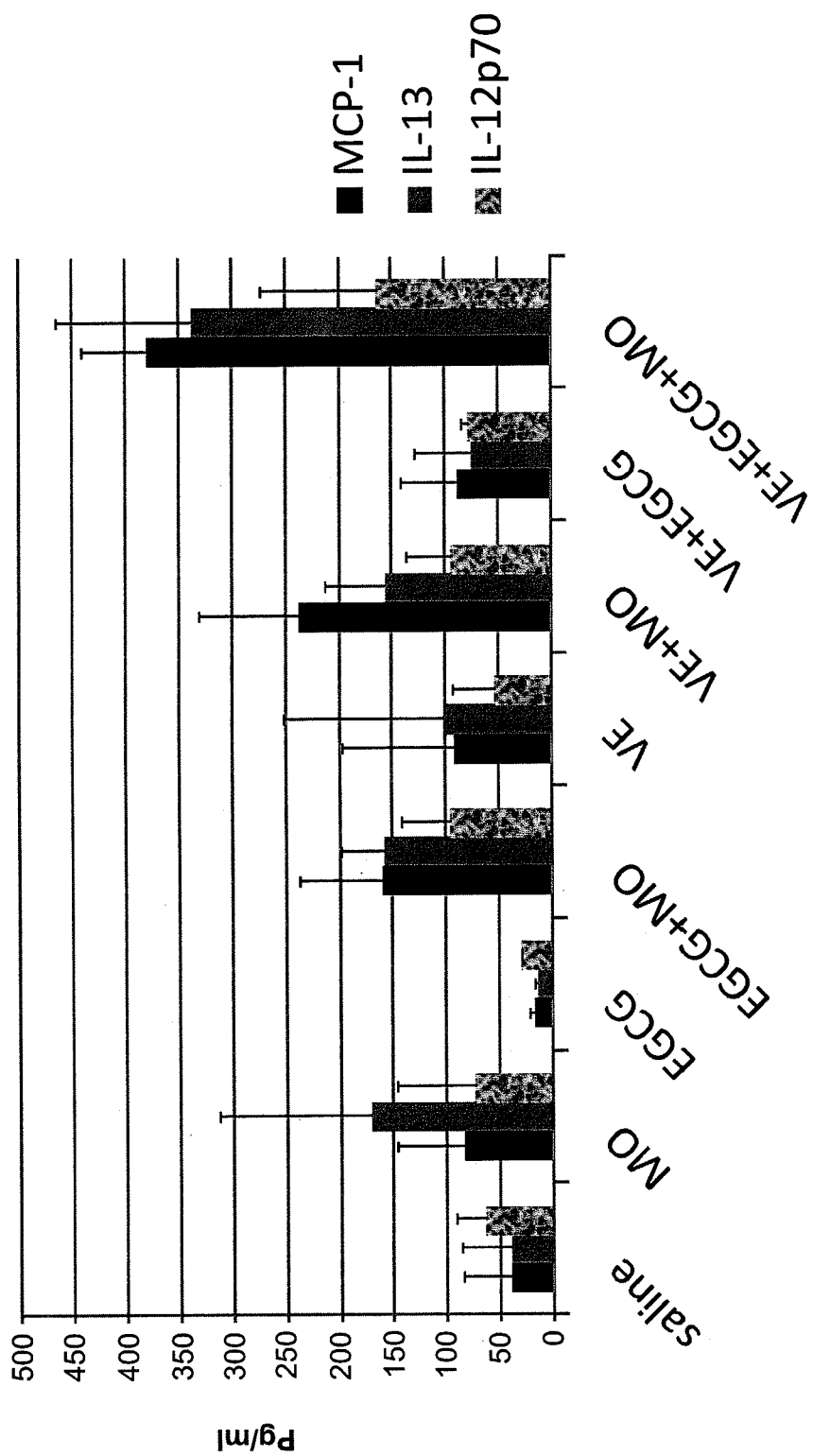
FIG. 2A is a bar graph showing synergistic effect of the flavonoid (EGCG), vitamin E (VE) and mustard seed oil (MO) for enhancement of monocyte chemotactic protein-1 (MCP-1; also known as CCL2), interleukin 13 (IL-13), interleukin 12p70 (IL-12p70)

Example 2: Synergistic effects of combinations of a flavonoid and a vitamin on early immune responses in vivo Female BALB/c mice (age 6-8 weeks) were given a single intra-muscular injection of gp120 from HIV-1$_{BaL}$ combined with EGCG, α-tocopherol (vitamin E; VE), each or in combination with mustard seed oil (MO), and compared to vaccinations with no adjuvant (saline). At 16 hours after the injection the serum levels of MCP1, IL-12p70 and IL-13 were synergistically enhanced with EGCG, VE and MO (FIG. 2A).

Figure 2B:
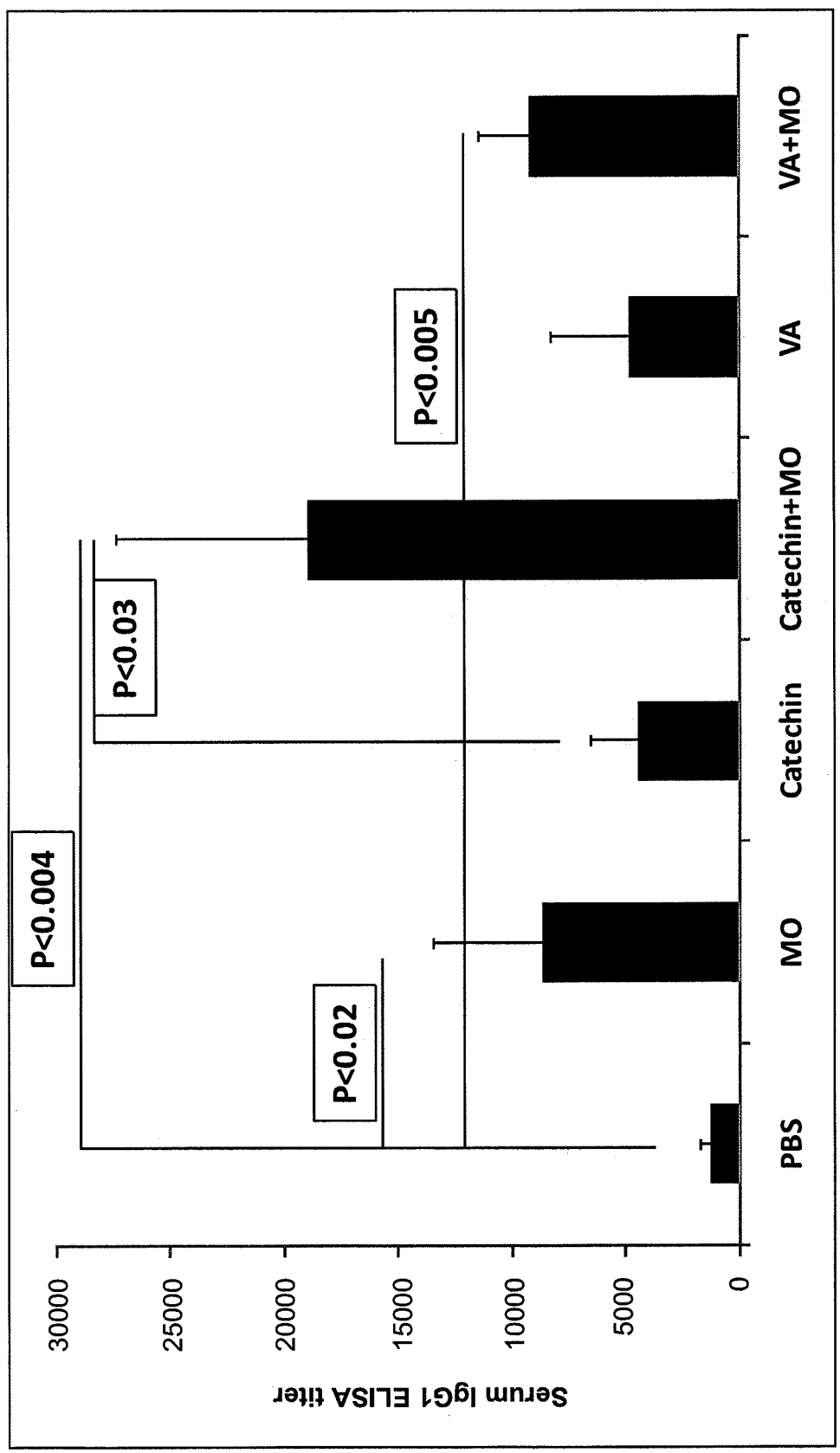
FIG. 2B is a bar graph showing mustard seed oil (MO) as a vaccine delivery system for vitamin A (VA; retinoic acid) or catechin (catechin hydrate) increased serum anti-influenza HA IgG1 responses following a single intra-muscular (IM) vaccination in which the responses are shown as serum IgG1 ELISA titers measured at 3 weeks after one IM vaccination and the p values are also shown.

In initial in vivo studies in BALB/c mice, using hemagglutinin (HA) from a seasonal influenza strain (H1N1; 0.5 µg), the combinations of vitamin A (VA; 30 µg), or catechin hydrate (cat; 120 µg) with mustard seed oil (MO) enhanced serum anti-HA IgG1 responses compared to vaccinations with no MO following a single intramuscular (IM) vaccination (FIG. 2B).

Figure 3:
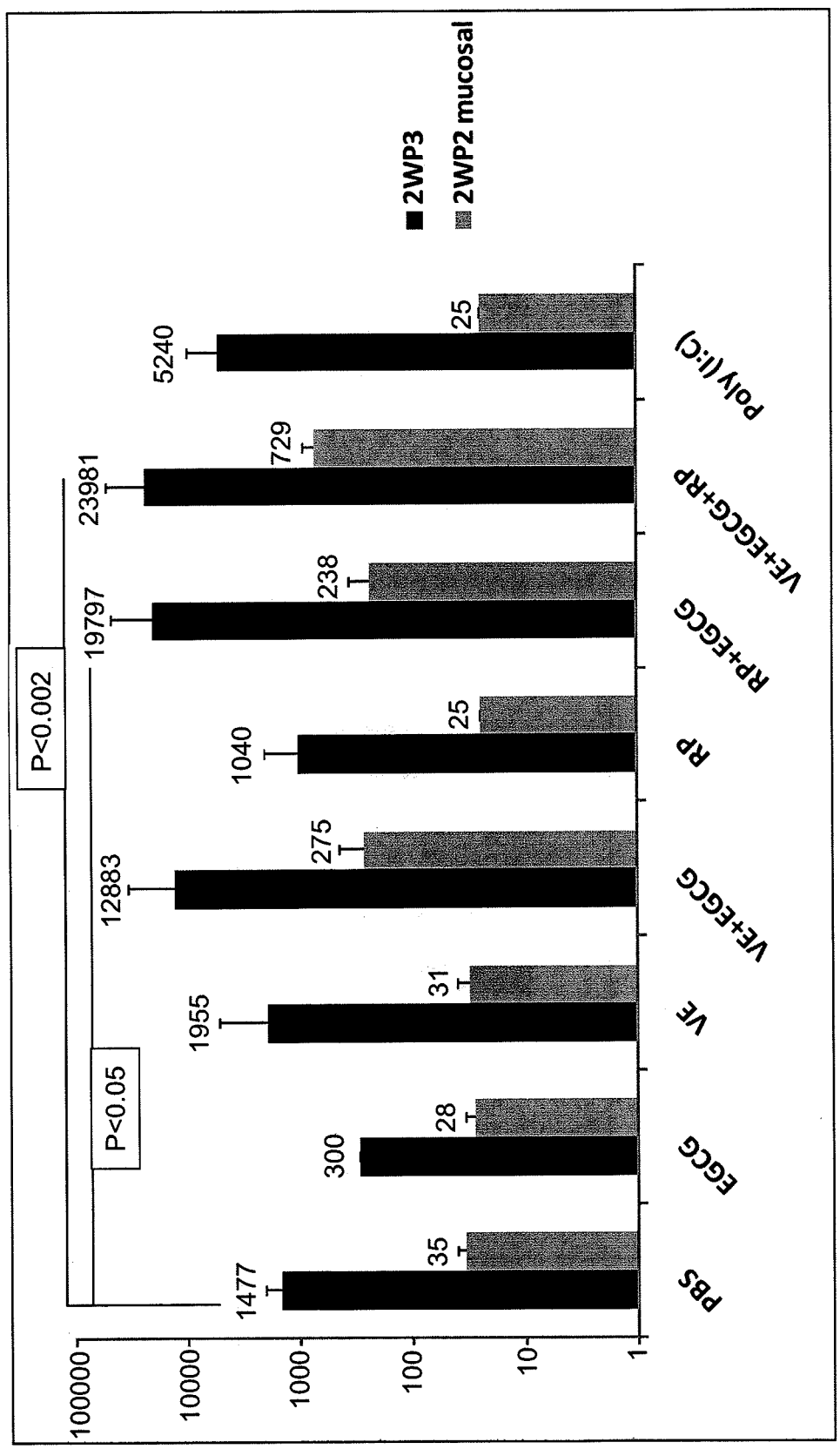
FIG. 3 is a bar graph showing the serum IgG1 anti-HIVgp120BaL titers at two weeks following two mucosal (combinations of intra-nasal and sublingual (IN/SL)) (2WP2) or two mucosal followed by one systemic (intra-muscular) vaccinations (2WP3) with HIVgp120BaL formulated in various components, i.e vitamin E (VE; alpha-tocopherol), epigallo catechin gallate (EGCG), retinyl palmitate (RP; vitamin A) in mustard seed oil (MO) compared to PBS and poly (I:C) (TLR3 agonist, dsRNA homologue)
Figure 4:
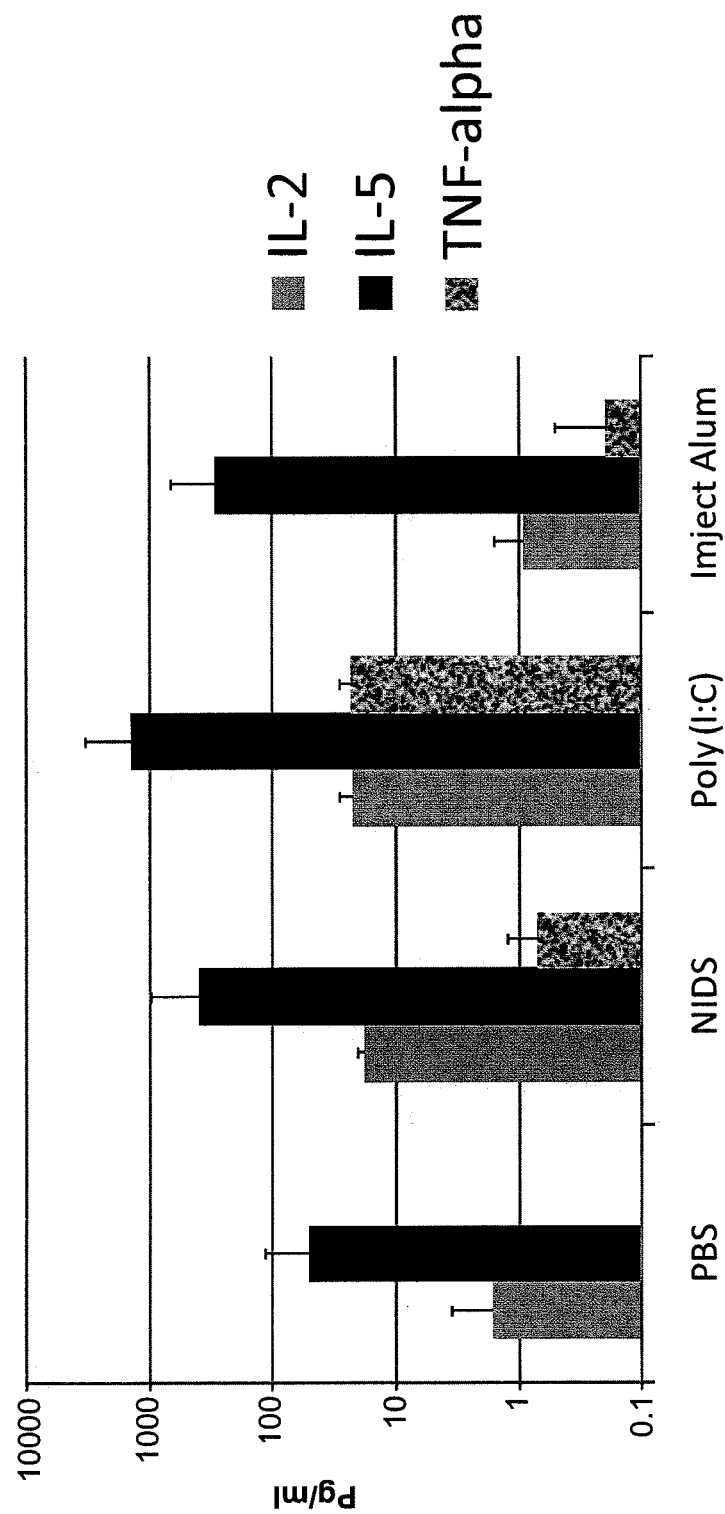
FIG. 4 is a bar graph showing enhanced local TH1 and TH2 cytokine responses in iliac lymph nodes following two mucosal (IN/SL) and one systemic (IM) boosting vaccinations with Nutritive Immune-enhancing Delivery System (NIDS, which comprises vitamin A, vitamin E, EGCG and MO), and Poly (I:C) vs. three IM vaccinations with Imject "Alum"

Combinations of Catechin and Vitamin A with Mustard Seed Oil Synergistically Enhanced Local and Systemic B and T Cell Responses Following Mucosal and Systemic Vaccinations Combinations of VA (retinyl palmitate; RP; 30 µg), VE (2 mg) and cat (120 µg) with 50% (vol/vol) MO that resulted in significantly higher serum IgG responses following mucosal and systemic vaccinations were determined. Combinations of VA+cat+MO or VA+VE+cat+MO induced the highest serum IgG responses after two mucosal and followed by two IM vaccinations (FIG. 3). Moreover, significantly enhanced TH1 (IL-2 and TNFα) and TH2 (IL-5) responses in the iliac lymph nodes that drain the vaginal mucosa were detected (FIG. 4). In this study, a comparison was made of the NIDS (VA+E+EGCG+MO) to the TLR3 agonist poly (I:C) which showed that the NIDS induced higher antibody responses than poly (I:C) following mucosal and systemic vaccinations.

Figure 5A:
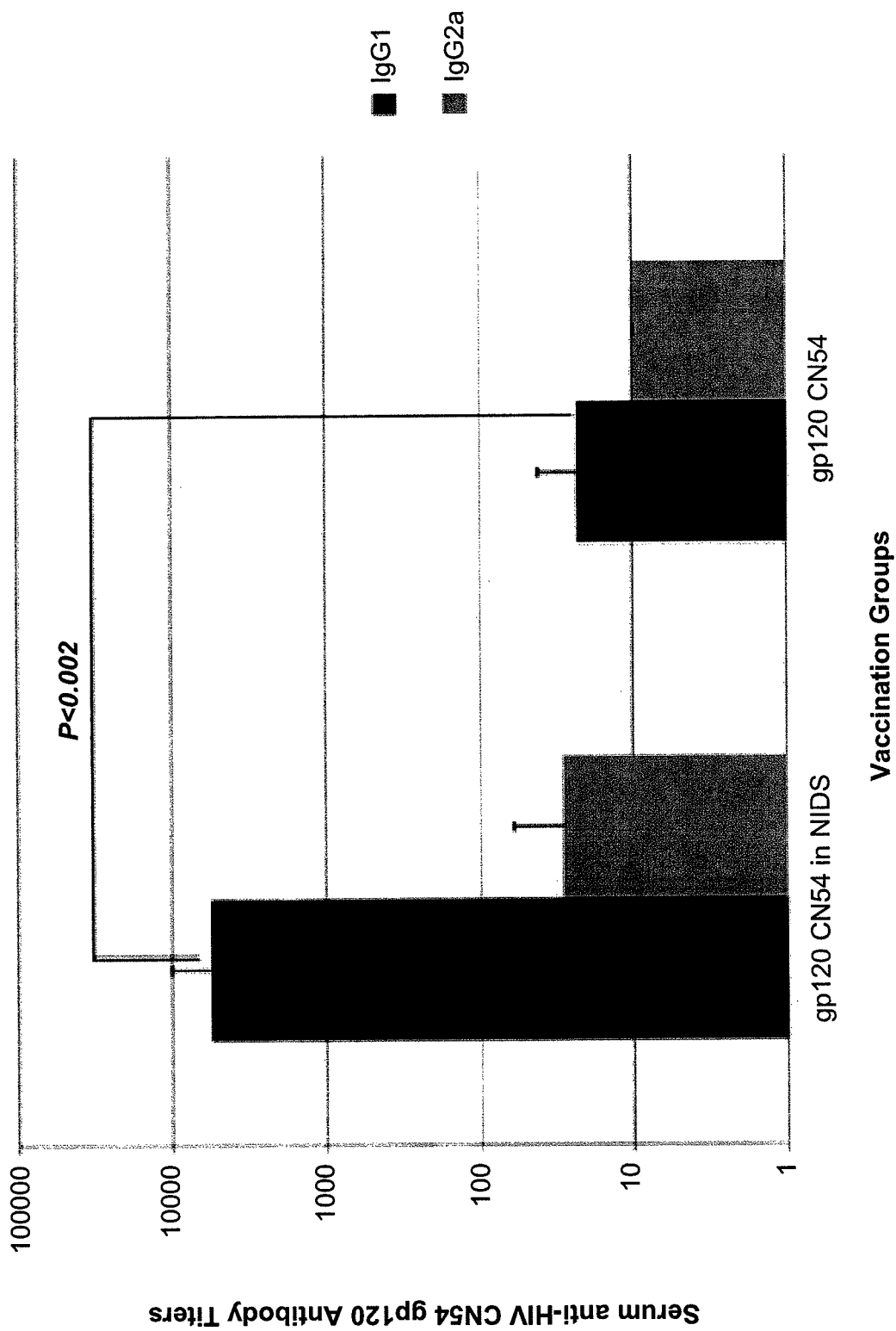
FIG. 5 is a bar graph showing serum antibody responses following two mucosal (left) and two mucosal followed by two systemic (right) vaccinations with gp120CN54 in NIDS or alone.
Figure 5B:
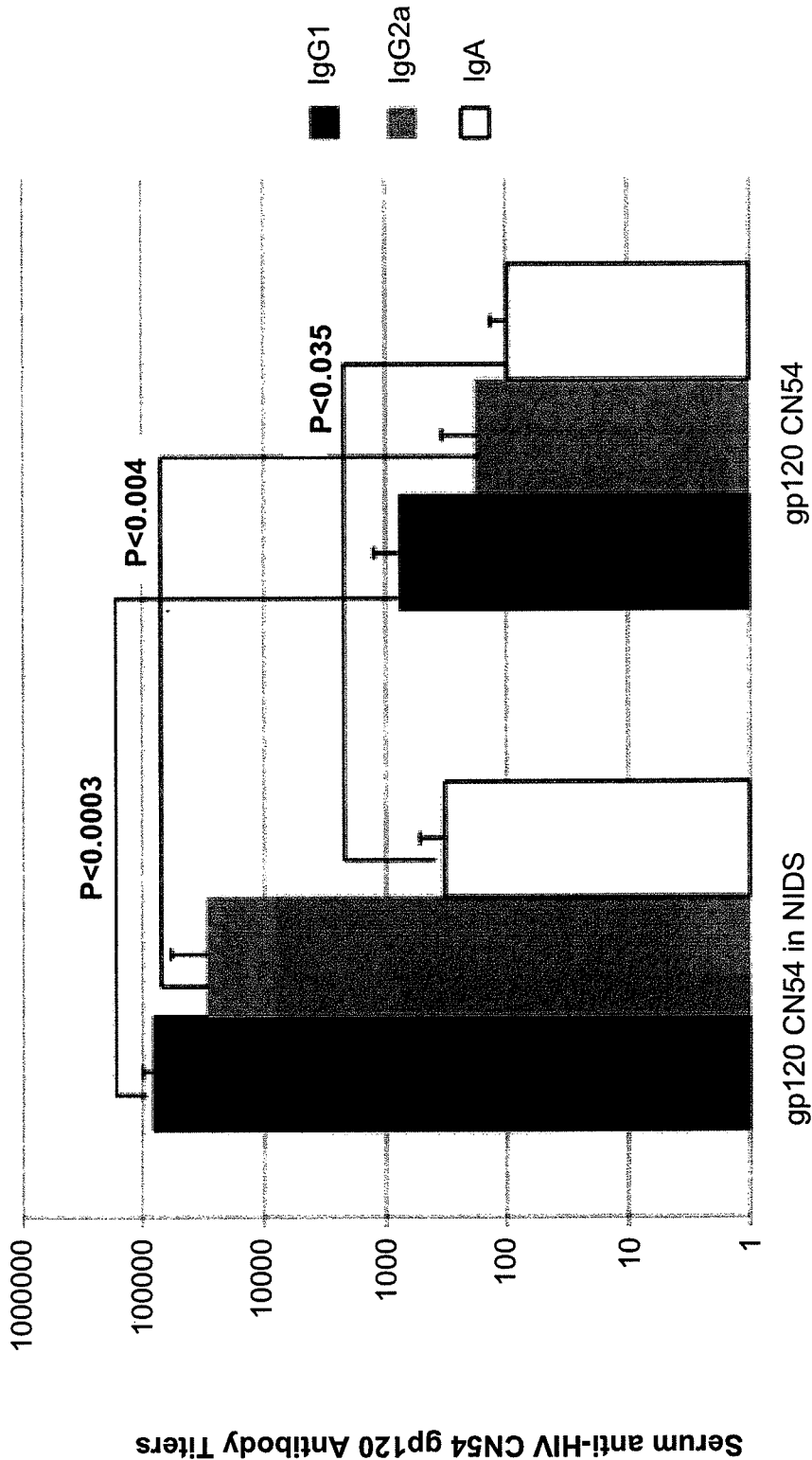
Figure 6:
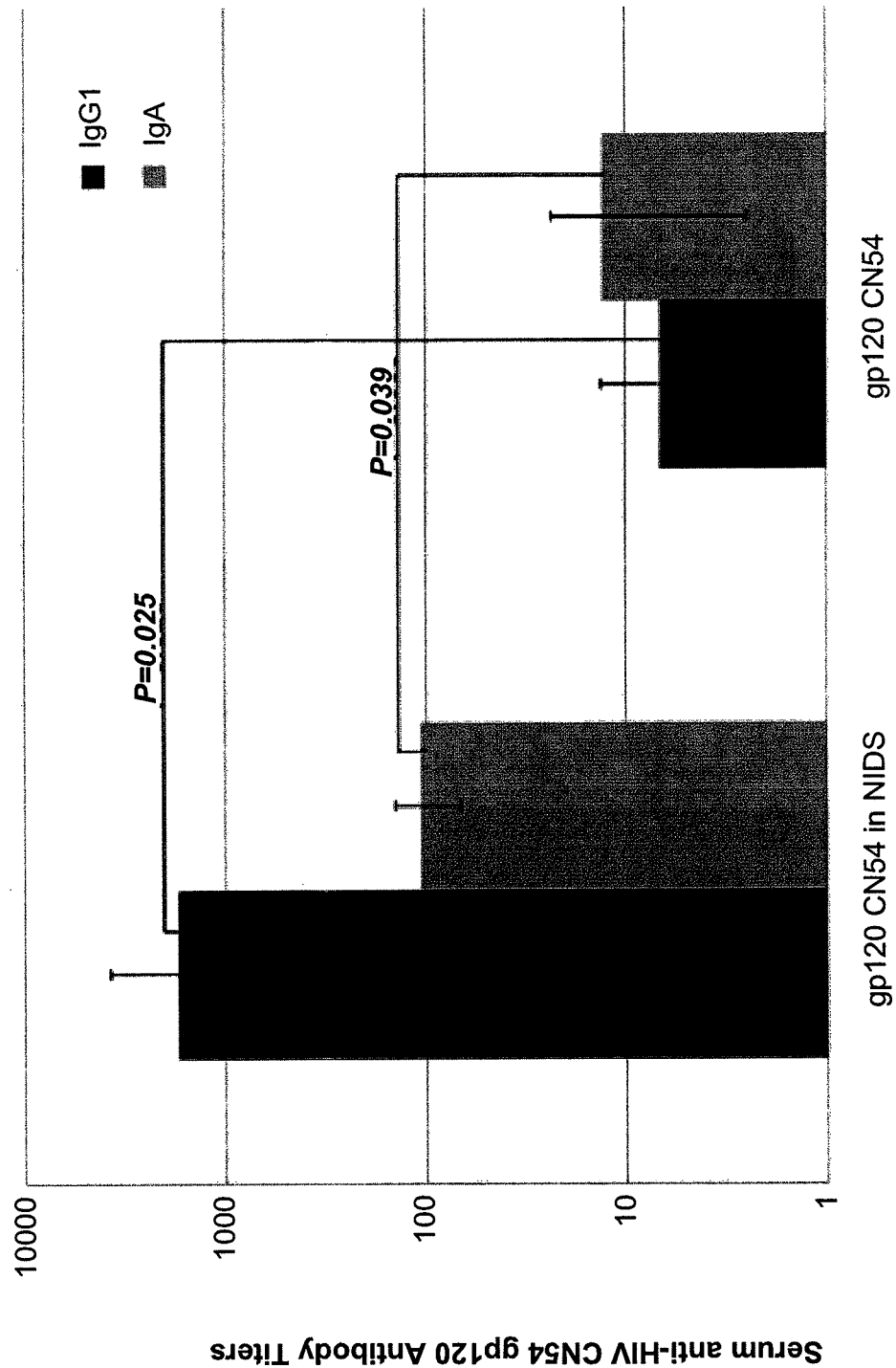
FIG. 6 is a bar graph showing anti-gp120CN54 IgG1 and IgA responses in vaginal washes at one week following two mucosal and two systemic vaccinations with gp120CN54 in NIDS or alone.

A study was performed using VA+cat+MO in mucosa followed by systemic vaccinations, which showed significantly enhanced serum IgG1, IgG2a, and IgA (FIG. 5) as well as enhanced vaginal lavage IgG1 and IgA (FIG. 6) following vaccinations with VA+cat+MO compared to no adjuvant, using the subtype C gp120CN54. Intriguingly, there were significant increases of serum IgG1 antibody titers not only against gp120 derived from the homologous CN54 subtype B/C, but also against several heterologous subtype B HIV-1 strains, i.e. BaL, CM, SF162 and IIIB. These data have been published (Yu M, Vajdy M. A novel retinoic acid, catechin hydrate and mustard oil-based emulsion for enhanced cytokine and antibody responses against multiple strains of HIV-1 following mucosal and systemic vaccinations. Vaccine. 2011 Mar. 16; 29(13):2429-36. Epub 2011 Jan. 25).

Figure 7:
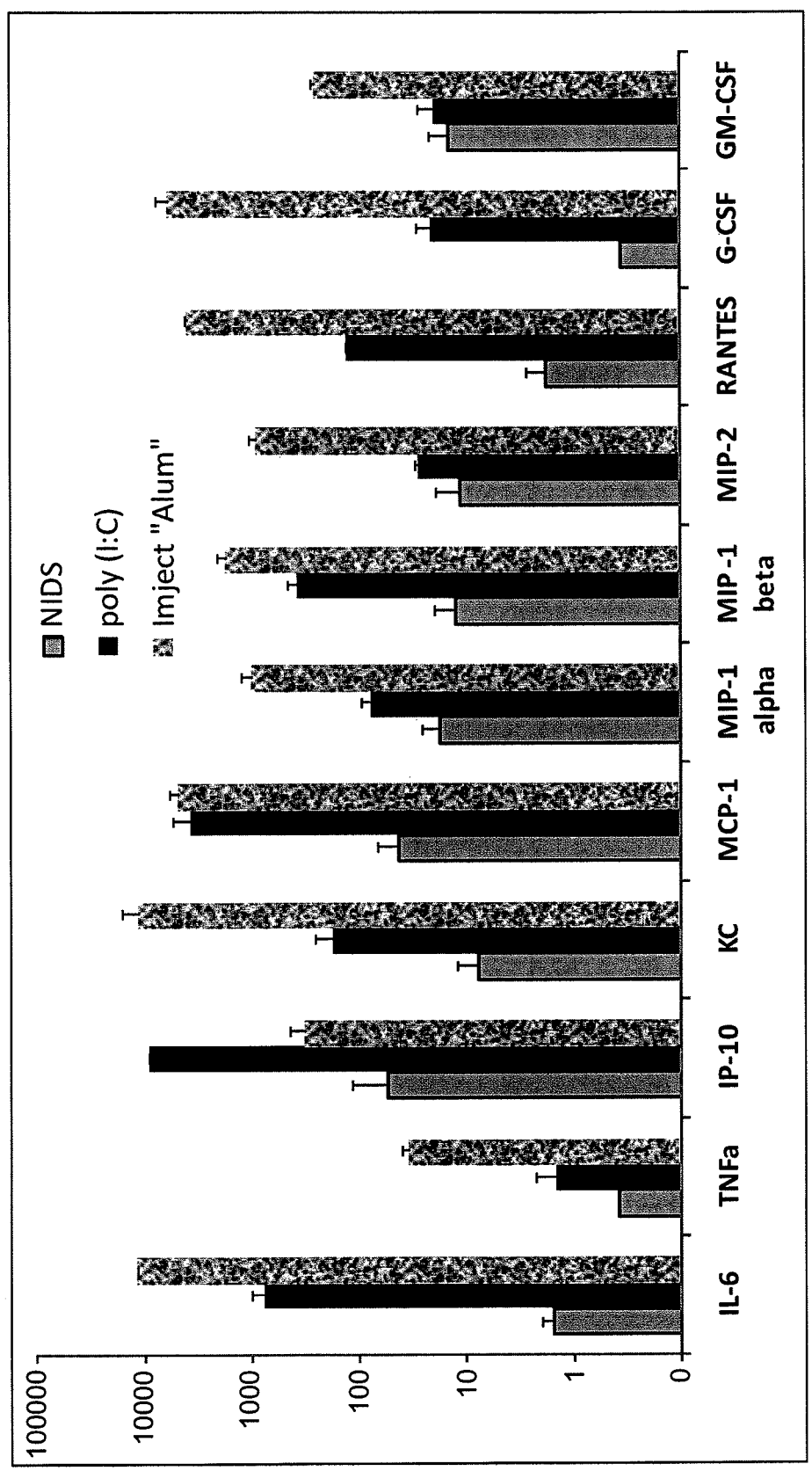
FIG. 7 is a bar graph showing significantly lower pro-inflammatory cytokines and chemokines following air pouch skin injection of NIDS (containing vitamins A and E and catechin in mustard seed oil) vs. poly (I:C) TLR3 agonist, vs. Imject Alum, in which the values are average of 3 mice per group in pg/ml (Y-axis) of fluid in the pouch collected at six hours post injection.

Example 3: NIDS Induced Dramatically Less Early Proinflammatory Cytokine and Chemokine Production Compared to Poly I:C and Imject Alum in the Murine Air Pouch Model of Cytotoxicity A local cytotoxicity test was performed by employing the murine air pouch model. This model also established whether the in vivo immune-enhancing effect of the NIDS can be delineated by early local cytokine and chemokine production. Seven times the mouse vaccine dose equivalents of NIDS (each dose containing 30 μg retinyl palmitate, 2 mg vitamin E (alpha-tocopherol, 120 μg epigallo catechin gallate, and 50% vol/vol mustard seed oil), poly (I:C) and imject alum was injected into the air pouches, supernatants were collected 6 hours later, and a multiplex Luminex assay was performed measuring multiple innate cytokine and chemokines. Significantly higher TNFα, IL-6, IP-10, KC, MCP-1, MIP1-a, MIP-1b, MIP-2, RANTES, and G-CSF were found following injection of poly (I:C) and imject alum compared to injection of NIDS (FIG. 7).

Figure 8:
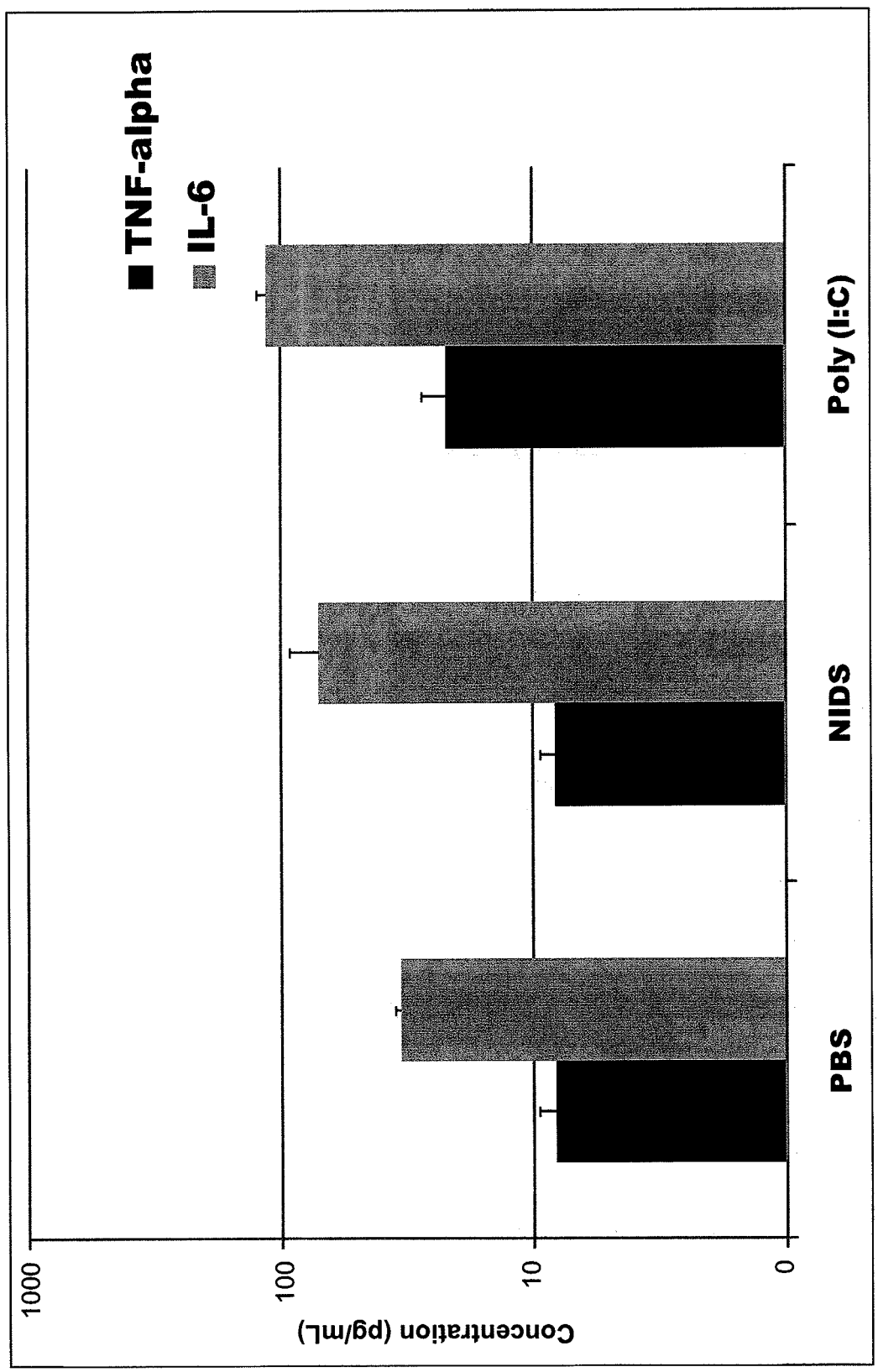
FIG. 8 is a bar graph showing serum TNF-alpha and IL-6 at six hours following an intra-muscular vaccination of mice with NIDS (containing vitamins A and E and EGCG in 50% mustard seed oil), in which the values are shown as average pg/ml of 6 mice per group.

To find further in vivo support of the above air pouch model results, in vivo production of early pro-inflammatory cytokines TNFα and IL-6 were determined in sera of mice at 6 hours following a single IM injection of NIDS vs. poly (I:C) vs. no adjuvant. We found that serum TNFα and IL-6 were significantly enhanced following IM vaccination with poly (I:C) vs. NIDS or no adjuvant (FIG. 8).

Figure 9:
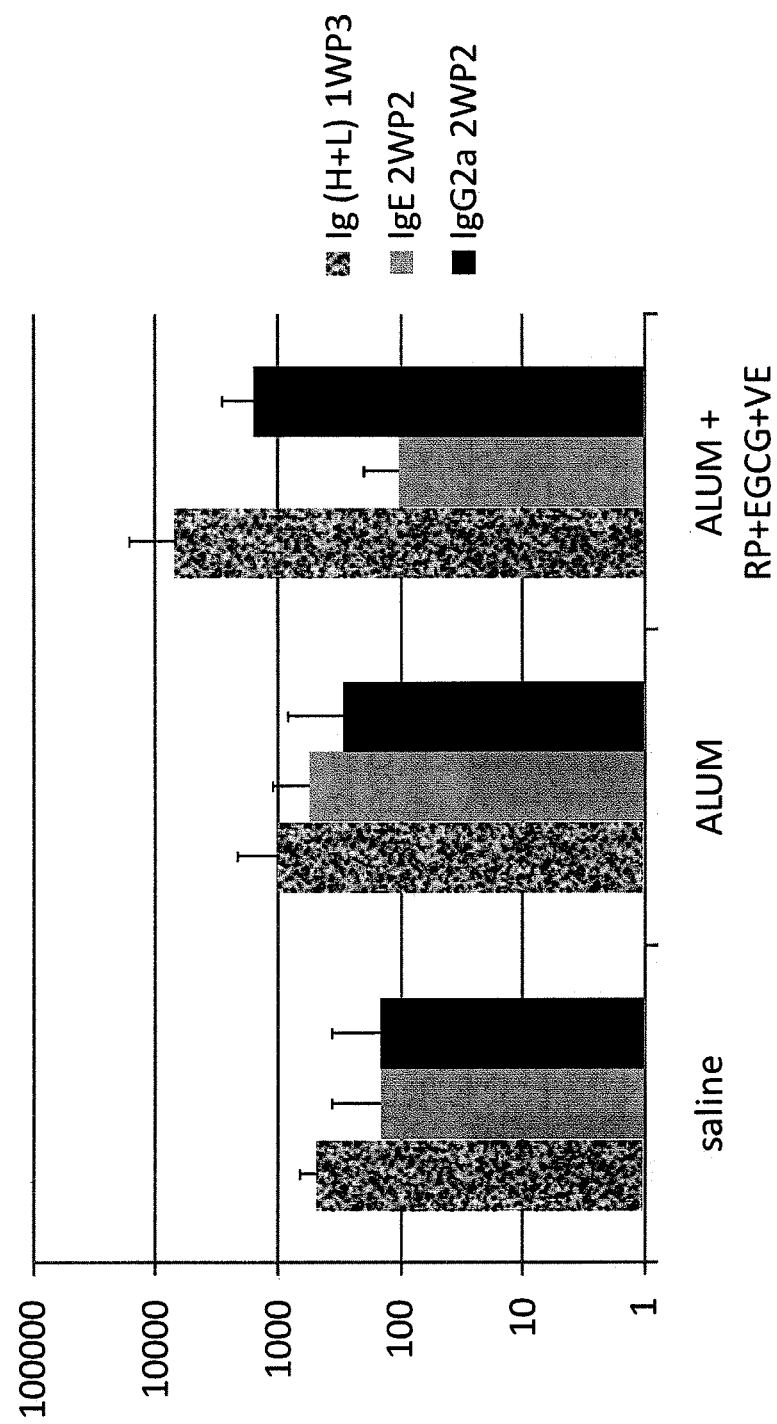
FIG. 9 is a bar graph showing IM vaccination with a combination of vitamins A, E and a flavonoid with Alum enhances serum responses compared to vaccination with Alum alone.

In another study, the immuno-modulatory effect of the combinations of vitamins A and E and a flavonoid was determined to assess whether this effect was dependent on the presence of mustard seed oil or whether it was also valid with other pharmaceutical carriers. To this end, female BALC/c mice were vaccinated intra-muscularly (IM) once or twice with gp120 from HIV-1 strain BaL, with Alum (aluminum Hydroxide 2.5%; Invivogen) in the presence or absence of the combination of vitamins A+E and EGCG. Following a single IM vaccination, the addition of vitamins A+E and EGCG to Alum, significantly enhanced serum antibody (Ig (H+ L)) responses (FIG. 9). Moreover, the addition of vitamins A+E and EGCG to Alum reduced antigen-specific serum IgE (indicative of overt TH2 responses), while it increased antigen-specific serum IgG2a responses following two IM vaccinations (FIG. 9).

Example 4: Immuno-Suppression by Reduction of MO and Immune Enhancement Using the Inorganic Carrier, Alum Groups of 4 female BALB/C mice were vaccinated intra-muscularly with various vaccine formulations containing 2.5 μg gp120 from the BaL strain of HIV-1 twice at a 3 weeks interval. Serum gp120-specific IgG1 titers were measured by ELISA at 2 weeks post second vaccination (2WP2). Two groups of mice were vaccinated with combinations of retinyl palmitate (RP; 54 IU), epigallo catechin gallate (EGCG; 120 μg) in either 50% mustard seed oil (MO) or 10% MO. Another two groups of mice were vaccinated with combinations of vitamin D3 (VD3; 20 IU), vitamin E (VE; 2 mg) and EGCG in either 50% MO or 10% MO. Another two groups of mice were vaccinated with 2.5% aluminum phosphate (Alum) alone or mixed with combinations of vitamin D3 (VD3), vitamin E (VE) and EGCG. A group of mice was vaccinated with gp120 in saline.

Figure 10:
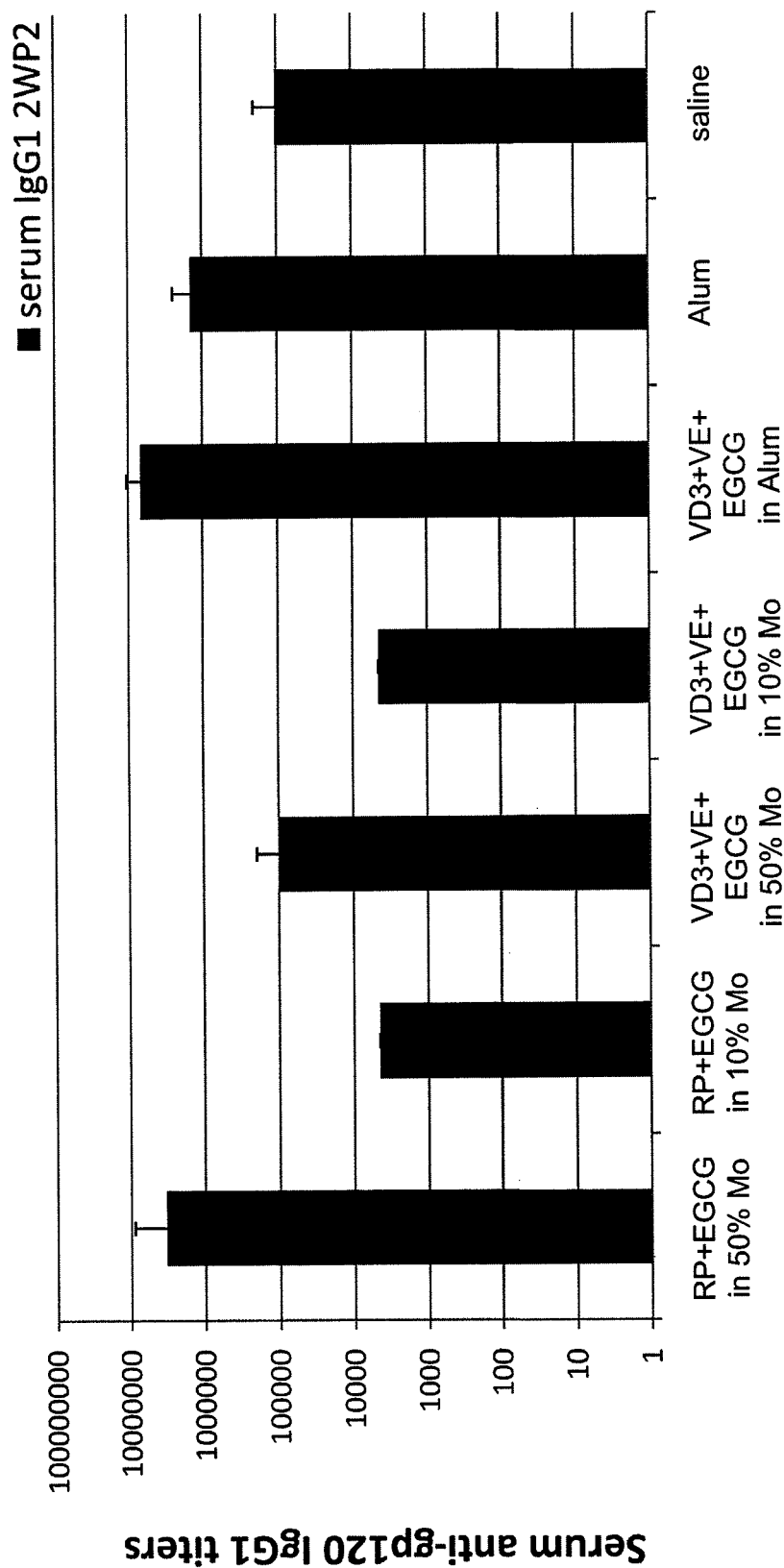
FIG. 10 is a bar graph showing antigen specific immuno-suppression with 10% MO and immuno-enhancement using Alum.

With reference to FIG. 10, reduction of mustard seed oil (MO) from 50% to 10% in the presence of retinyl palmitate (RP) and epigallo catechin gallate (EGCG) significantly suppressed the serum IgG1 antigen-specific responses. Reduction of MO from 50% to 10% in the presence of VD3, VE and EGCG significantly suppressed the serum IgG1 antigen-specific responses. Further, addition of VD3, VE and EGCG to Alum significantly enhanced serum IgG1 antigen-specific responses compared to vaccinations with Alum alone.

Figure 11:
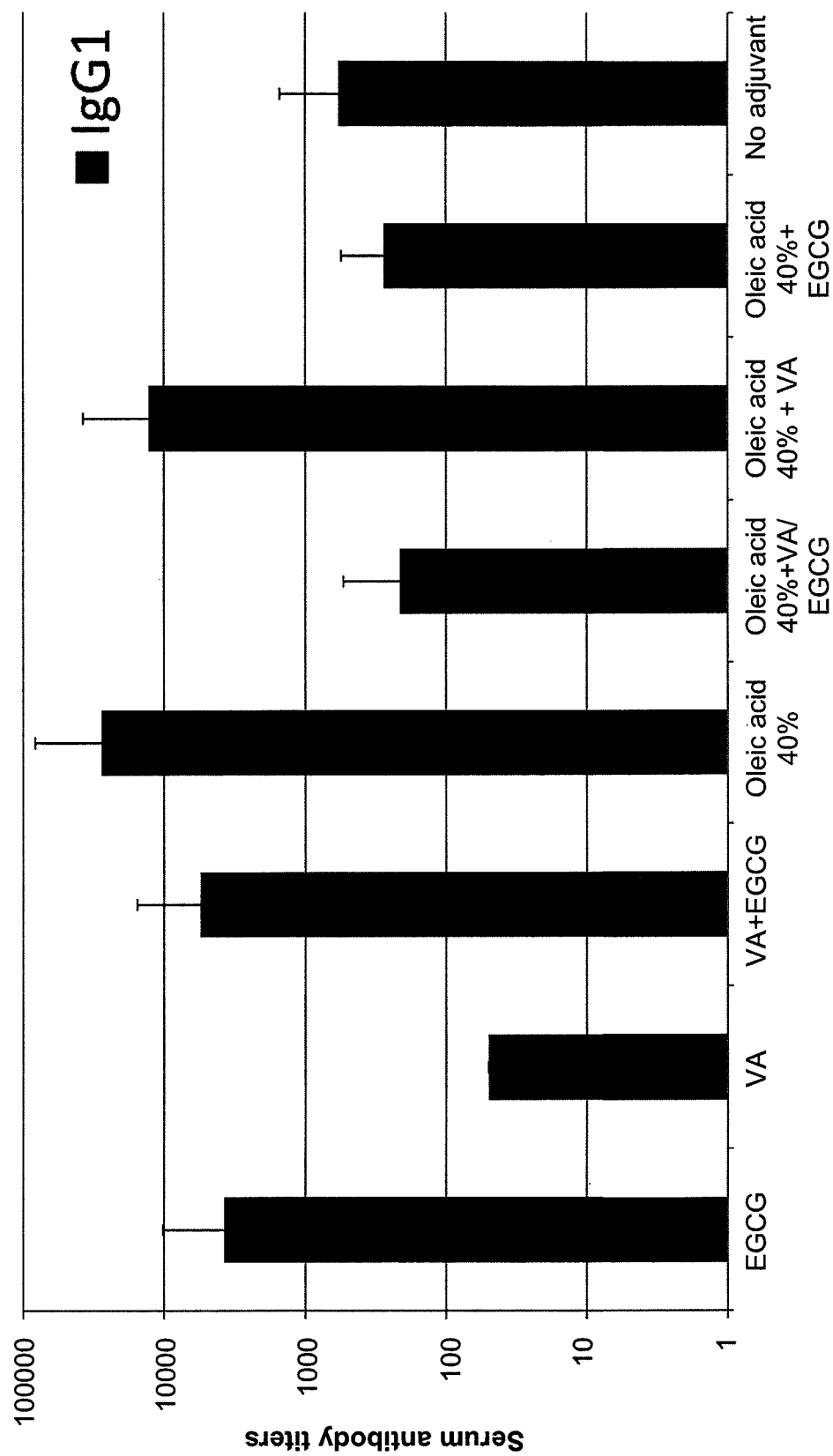
FIG. 11 is a bar graph showing antigen specific immune-enhancement following IM vaccinations with oleic acid alone or with vitamin A and synergistic immuno-suppression by combinations of epigallo catechin gallate and vitamin A in oleic acid.

Example 5: Antigen-Specific Immune-Enhancement Following Vaccinations with Oleic Acid (a Fatty Acid, 40% Vol/Vol) Alone or with Vitamin a, and Synergistic Immuno-Suppression by Combinations of Epigallo Catechin Gallate and Vitamin a in Oleic Acid Groups of 4 female BALB/C mice were vaccinated intra-muscularly with various vaccine formulations containing 2.5 ug gp120 from the BaL Glade of HIV-1 twice at a 3 weeks interval. Serum gp120-specific IgG1 titers were measured by ELISA at 2 weeks post second vaccination (2WP2). The mice were vaccinated with combinations of retinyl palmitate (RP; 54 IU), epigallo catechin gallate (EGCG; 120 ug) in either 40% oleic acid, each alone or in various combinations. As shown in FIG. 11, a single fatty acid, oleic acid, alone or combined with RP and enhanced serum IgG1 antigen-specific responses compared to oleic acid plus EGCG, VA plus EGCG alone or no adjuvant. Further, FIG. 11 shows that Addition of EGCG to RP and Oleic acid synergistically suppressed serum IgG1 antigen-specific responses compared to oleic acid alone or no adjuvant.

Synergistic antigen-unspecific immunosuppression following vaccinations with oleic acid (a fatty acid, 40% vol/vol) alone compared to oleic acid combined with vitamin A, and catechin.

Groups of 4 female BALB/C mice were vaccinated intra-muscularly once with various vaccine formulations containing 2.5 ug gp120 from the BaL strain of HIV-1. Serum cytokines and chemokines were measured by ELISA at 6 hours following the vaccination. The mice were vaccinated with combinations of vitamin A (VA; retinyl palmitate 54 IU), epigallo catechin gallate (EGCG; 120 ug) in either 40% oleic acid, each alone or in various combinations.

Figure 12:
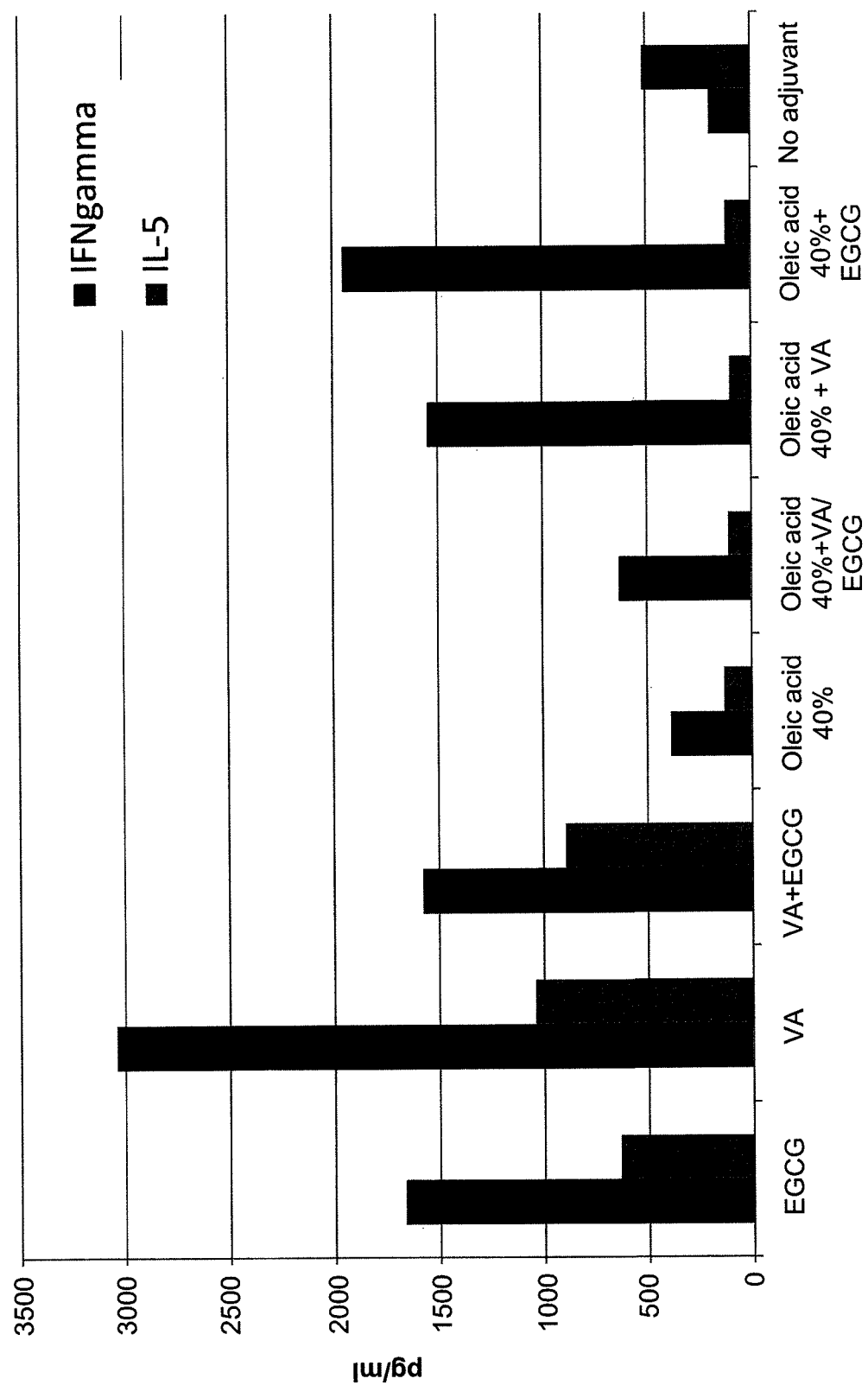
FIG. 12 is a bar graph showing antigen specific TH1 enhancement and TH2 suppression following vaccination with oleic acid alone, oleic acid+EGCG, oleic acid+VA, oleic acid+cat and oleic acid+VA+cat.

FIG. 12 shows the synergistic antigen-unspecific immunosuppression following a single injection with oleic acid (a fatty acid, 40% vol/vol) combined with vitamin A, and catechin compared to oleic acid alone, oleic acid plus vitamin A, or oleic acid combined with EGCG Example 7: Synergistic Antigen-Unspecific Immunosuppression Following Vaccinations with Oleic Acid (a Fatty Acid, 40% Vol/Vol) Alone Compared to Oleic Acid Combined with Vitamin a, and Catechin Groups of 4 female BALB/C mice were vaccinated intra-muscularly once with various vaccine formulations containing 2.5 μg gp120 from the BaL strain of HIV-1. Serum cytokines and chemokines were measured by ELISA at 6 hours following the vaccination. The mice were vaccinated with combinations of vitamin A (VA; retinyl palmitate 54 IU), epigallo catechin gallate (EGCG; 120 µg) in either 40% oleic acid, each alone or in various combinations.

Figure 13:
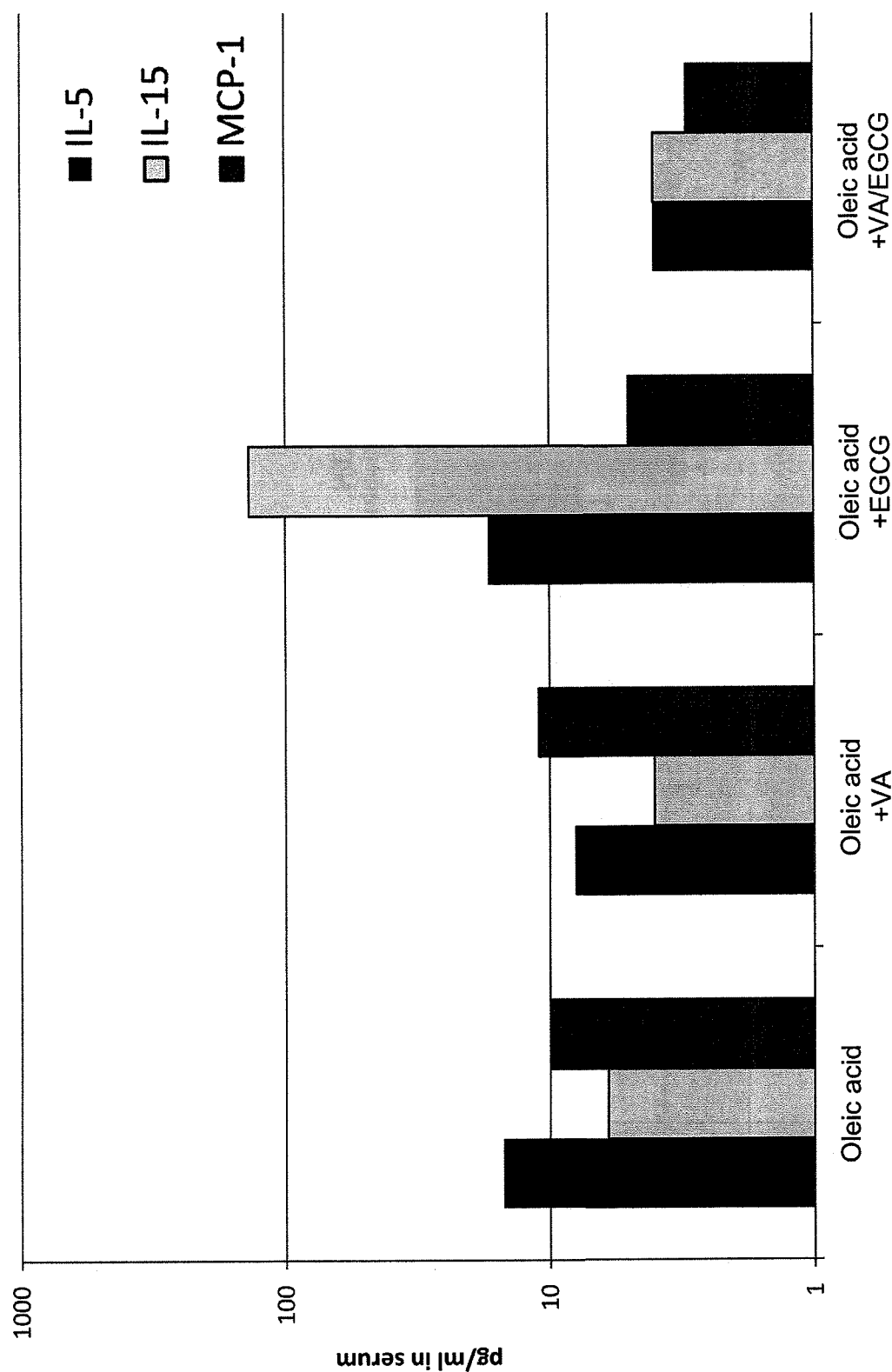
FIG. 13 is a bar graph showing synergistic antigen-nonspecific immuno-suppression following vaccinations with oleic acid lone compared to oleic acid combined with VA and EGCG.

FIG. 13 shows the results from this study demonstrating synergistic antigen-unspecific immunosuppression following a single injection with oleic acid (a fatty acid, 40% vol/vol) combined with vitamin A, and catechin compared to oleic acid alone, oleic acid plus vitamin A, or oleic acid combined with EGCG.

Figure 14:
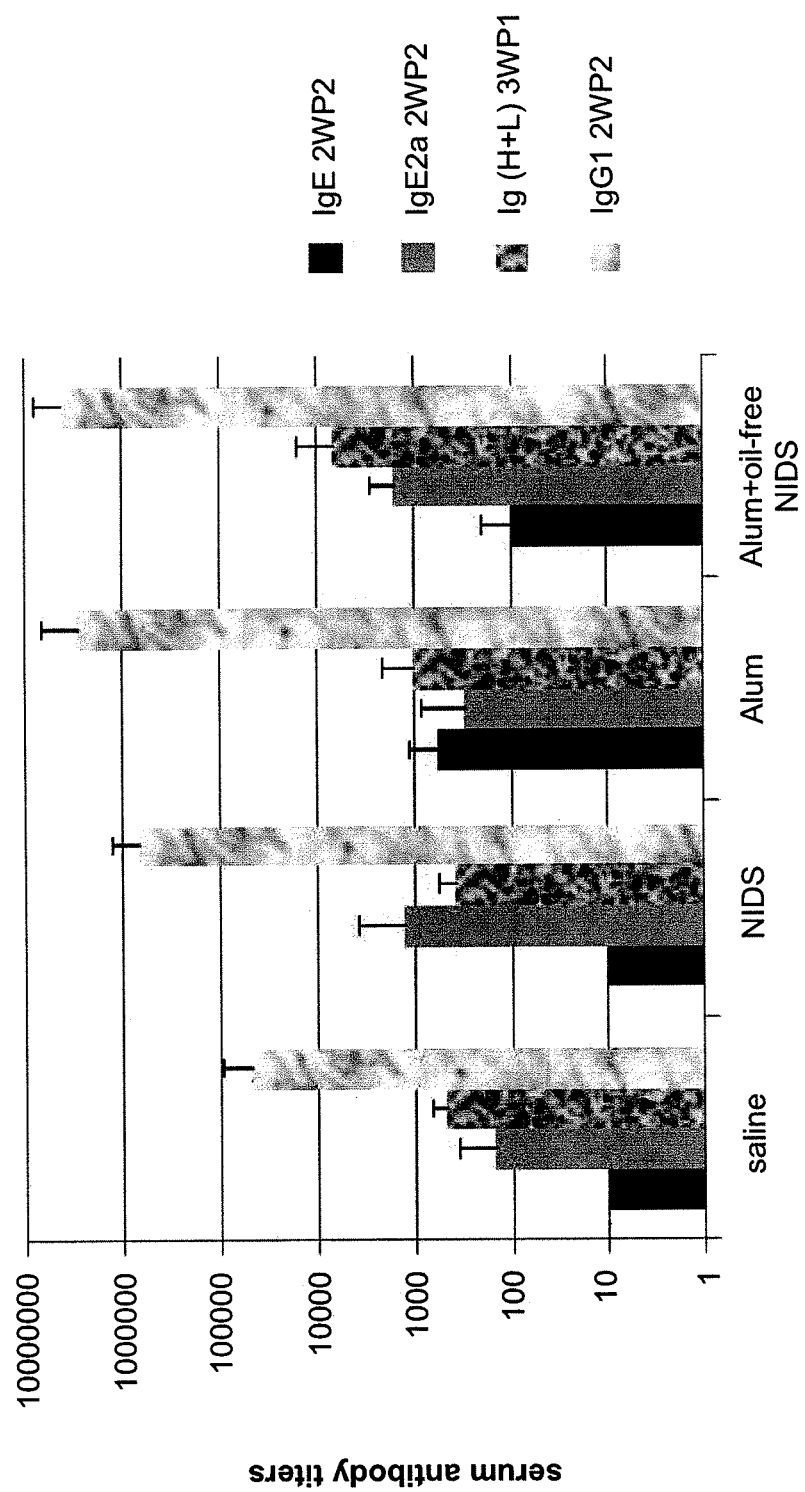
FIG. 14 is a bar graph showing immune-enhancement following IM vaccination with NIDS (retinyl palmitate, epigallo catechin gallate (EGCG), α-tocopherol, 50% mustard seed oil), versus Alum versus oil free NIDS+Alum.

Example 8: Enhancement of Anti-HIV-120 Ig Responses and IgG2a Responses with Reduced IgE Responses with NIDS, or Alum, or Oil Free NIDS & Alum Groups of 4 female BALB/c mice were vaccinated intra-muscularly once or twice for comparison of NIDS (54 IU retinyl palmitate, plus 120 µg epigallo catechin gallate, plus 2 mg alpha tocopherol in 50% MO) vs. Alum, vs. Alum+oil free NIDS for induction of TH1 vs. TH2 antibody responses against HIV-120 BaL (2.5 µg per dose) following one (3WP1) two (2WP2) IM vaccinations FIG. 14 shows that addition of vitamins A and E and a catechin significantly enhanced serum total anti-env Ig responses following a single IM vaccination, and significantly enhanced serum IgG2a while reducing serum IgE responses comparing NIDS vs. Alum vs. Alum plus oil-free NIDS.

Example 9: Antigen-Unspecific Enhancement of Serum IL-5 Responses at 6 Hours Following a Single Intra-Muscular Injection with VE, EGCG and Alum Groups of 3 female BALB/C mice were injected once intra-muscularly with various formulations containing retinyl palmitate (RP; vitamin A; 54 IU), epigallo catechin gallate (EGCG; 120 µg), and/or 2.5% Alum (50% vol/vol from Invivogen, San Diego, Calif.). Sera were collected at six hours post injection and IL-5 cytokine response was measured by the multiplex luminex assay.

Figure 15:
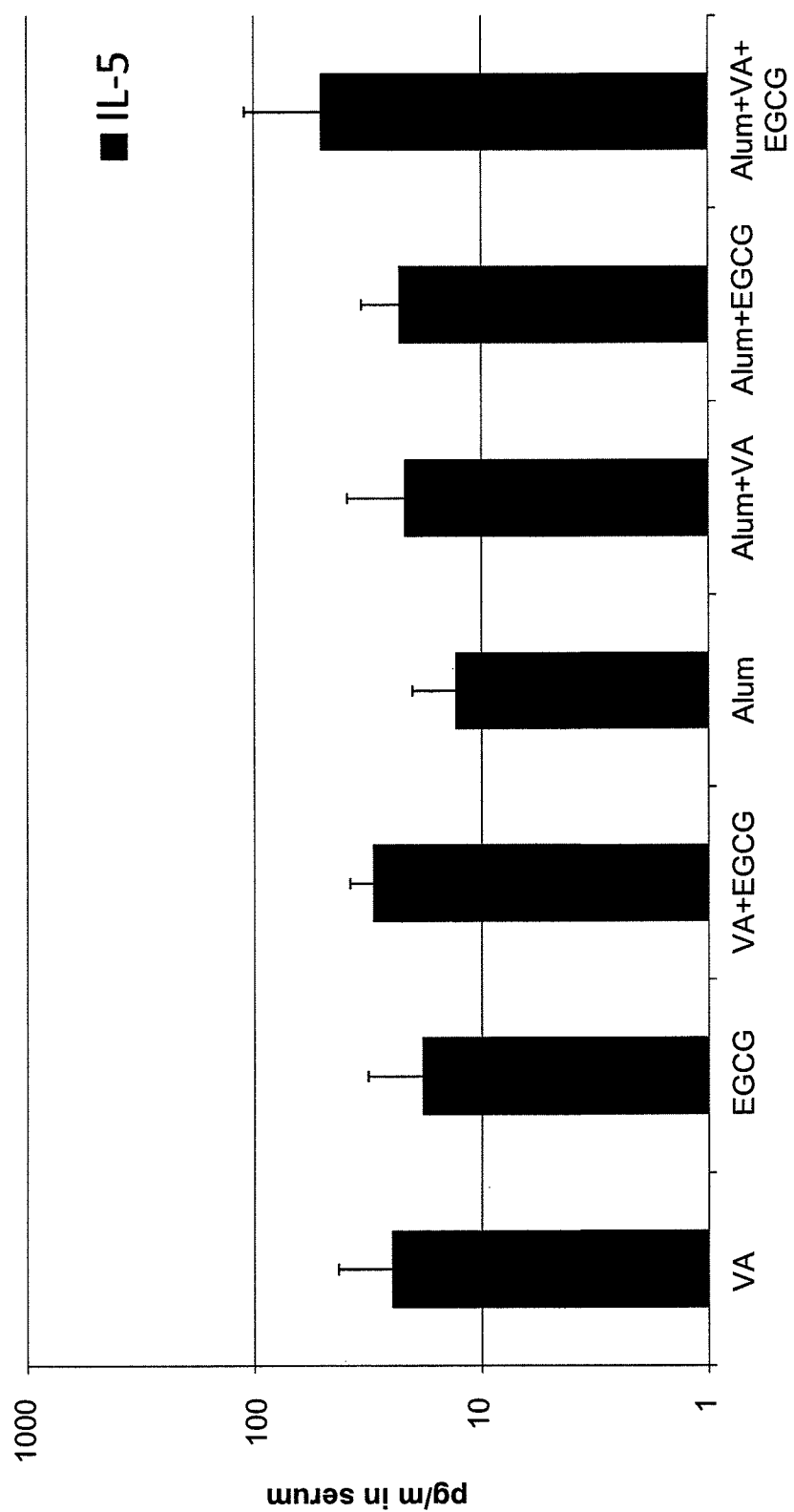
FIG. 15 is a bar graph showing antigen-unspecific enhancement of serum IL-5 responses at 6 hours following a single intra-muscular injection with VE, EGCG, aluminum hydroxide (Alum)

Combinations of Vitamin A and EGCG induce antigen-unspecific synergistic enhancement of serum IL-5 at 6 hours following a single intra-muscular injection with Alum (FIG. 15).

Example 10: Antigen-Specific Immuno-Enhancement Through Synergistic Effect of Gallic Acid (a Polyphenolic Tannin), Vitamin a and Mustard Seed Oil (MO)

Groups of 3-4 female BALB/C mice were vaccinated intra-muscularly with various vaccine formulations containing 2.5 ug gp120 from the BaL strain of HIV-1 twice at a 3 weeks interval. Serum gp120-specific IgG1 titers were measured by ELISA at 2 weeks post second vaccination (2WP2). The vaccines contained per dose vitamin A (VA; retinyl palmitate; 54 IU), gallic acid (120 µg) in 50% MO, each alone or in various combinations.

Figure 16:
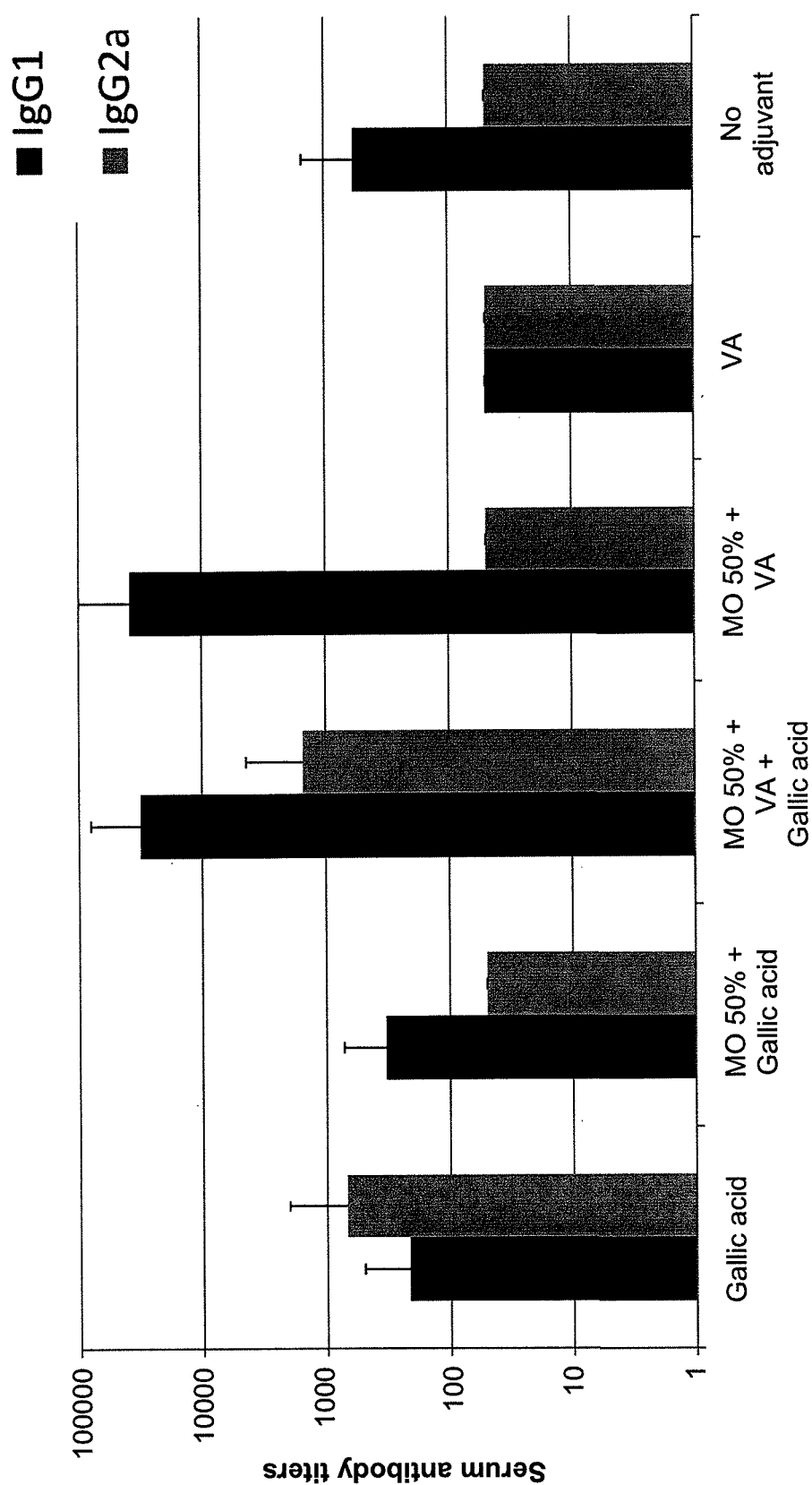
FIG. 16 is a bar graph showing antigen-specific immuno-enhancement through synergistic effect of tannin (gallic acid), vitamin A and MO.

The data from these studies showed that antigen-specific Immuno-enhancement through synergistic effect of gallic acid (a polyphenolic tannin), vitamin A and mustard seed oil (MO) synergistically enhanced serum antigen specific IgG1 (TH2) and IgG2a (TH1) antibody responses (FIG. 16).

Example 11: Suppression of TH2 and Enhancement of TH1 Cytokine Responses Following Vaccinations with Vitamins a and E with Catechin in 10% or 50% or 75% Mustard Seed Oil (MO)

Groups of 4 female BALB/C mice were vaccinated intra-muscularly with various vaccine formulations containing 2.5 µg gp120 from the BaL strain of HIV-1 twice at a 3 weeks interval. Serum gp120-specific IgG1 titers were measured by ELISA at 2 weeks post second vaccination (2WP2). At 2WP2 single cell suspensions were prepared from spleens and activated ex vivo with 2 µg/ml of gp120 overnight and supernatants were collected the day after and various cytokines were measured by the multiplex Luminex assay. Groups of mice were vaccinated with combinations of retinyl palmitate (RP; 54 IU), vitamin E (VE; 2 mg), epigallo catechin gallate (EGCG; 120 µg) in either 10%, 50% or 75% mustard seed oil (MO). Another two groups of mice were vaccinated with combinations of vitamin D3 (VD3; 20 IU), vitamin E (VE) and EGCG in either 50% MO or 10% MO. Another two groups of mice were vaccinated with 2.5% aluminum phosphate (Alum) alone or mixed with combinations of vitamin C (VC), VE and EGCG with and without RP. A group of mice was vaccinated with gp120 in saline or in a squalene oil based carrier (AdjuMF59; Invivogen, San Diego, Calif.).

Figure 17:
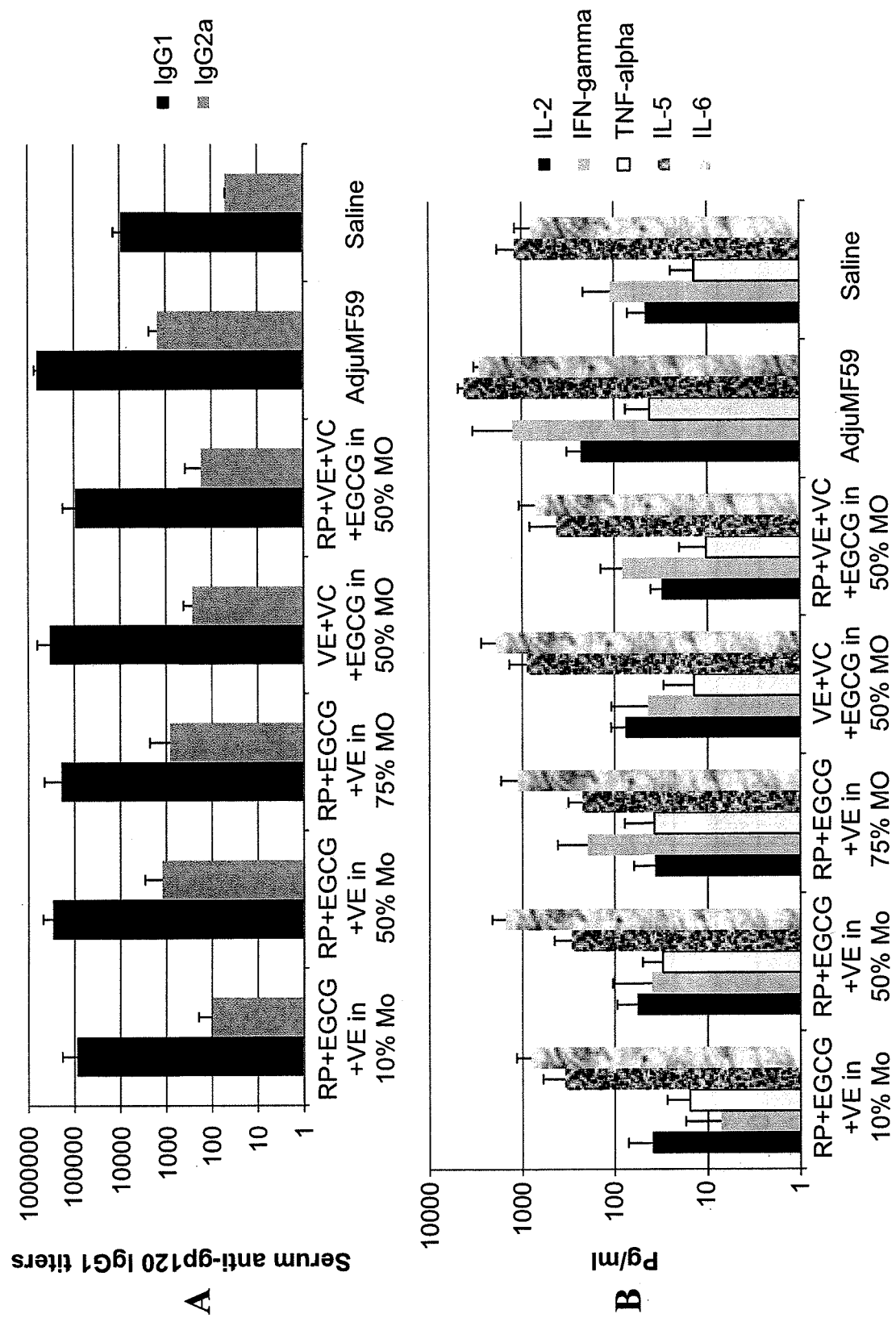
FIGS. 17 A & B are a bar graphs showing suppression of TH2 and enhancement of TH1 cytokine responses following vaccinations with vitamins A and E with catechin in 10%, 50% or 75% mustard seed oil.

RP (54 IU)+VE (2 mg)+EGCG (120 µg) in 75% MO significantly enhanced serum IgG1 and IgG2a (TH1), and splenic IFNγ (TH1), while reducing IL-5 (TH2) responses compared to vaccinations with saline (FIGS. 17A and 17B). RP+VE+EGCG in 75% MO significantly enhanced serum IgG2a (TH1), and splenic IFN-gamma (TH1) responses compared to vaccinations with RP+VE+EGCG in 10% MO (FIGS. 17A and 17B)

Example 12: Vitamin a and Catechin Synergistically Enhance Serum Antibody Responses Against HIV-1 (BaL Strain) Gp120 Protein Groups of 4 female BALB/C mice were vaccinated intra-muscularly twice at 2.5 weeks interval with 2.5 ug of gp120 in liposomes measuring 150 nm in diameter ((composed of Dimyristoylphosphotidylcholine (2% W/V), Dimyristoyl-phosphotidylglycerol (0.6% W/V), Cholesterol (0.4% W/V), Sucrose (9% W/V), Disodium succinate hexahydrate (0.27% W/V)) alone, with vitamin A (VA: retinyl palmitate; 54 IU), or epigallo catechin gallate (EGCG; 120 µg) or combinations of VA and EGCG. Total serum immunoglobulins (Ig Heavy and Light chains) were measured by ELISA at 2 weeks after the final vaccination.

Figure 18:
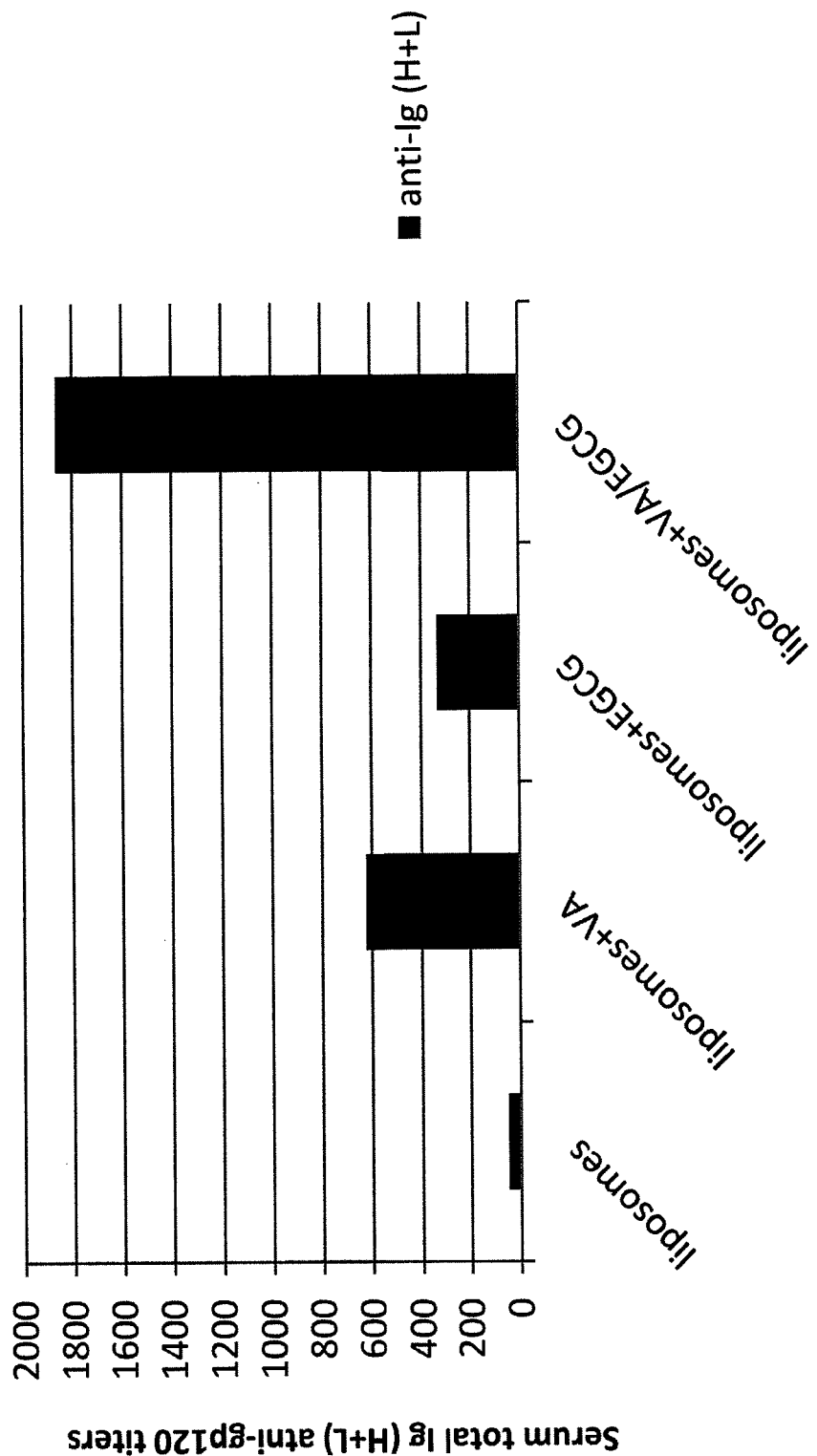
FIG. 18 is a bar graph showing the synergistic enhancement of serum antibody responses again HIV-1 gp120 protein in liposomes by VA and EGCG.

FIG. 18 shows that combinations of VA and EGCG mixed with liposomes synergistically enhance serum antibody responses.

Example 13: Synergistic Immune Enhancement Effect of Vitamin a and E and Catechin Squalene Oil-Based Carrier Groups of 4 female BALB/C mice were vaccinated intra-muscularly with various vaccine formulations containing 2.5 µg gp120 from the BaL strain of HIV-1 twice at a 3 weeks interval. Serum gp120-specific IgG1 titers were measured by ELISA at 2 weeks post second vaccination (2WP2). Two groups of mice were vaccinated with combinations of retinyl palmitate (RP; 54 IU), epigallo catechin gallate (EGCG; 120 µg) in 5% vol/vol squalene oil.

Figure 19:
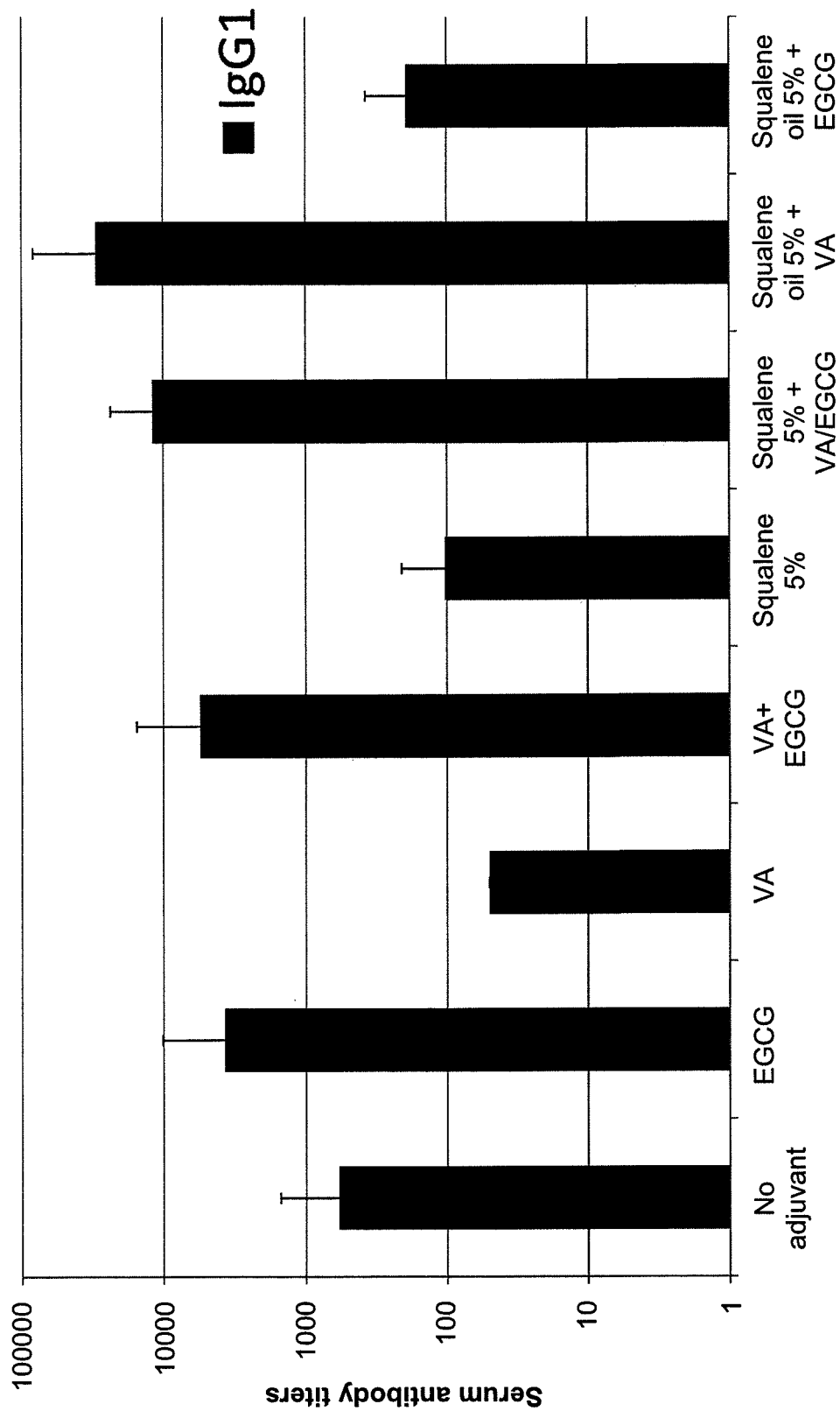
FIG. 19 is a bar graph showing synergistic immune enhancement after vaccination with VA, VE, EGCG and squalene oil-based carrier.

FIG. 19 shows that addition of VA and EGCG to squalene oil-based carrier synergistically enhanced serum IgG1 responses.

Example 14: Synergistic Immune Enhancement Effect of Vitamin a and E and Catechin with Various Oil-Based Carriers Groups of 4 female BALB/C mice were vaccinated intra-muscularly with various vaccine formulations containing 2.5 μg gp120 from the BaL strain of HIV-1 twice at a 3 weeks interval. Serum gp120-specific IgG1 titers were measured by ELISA at 2 weeks post second vaccination (2WP2). Two groups of mice were vaccinated with combinations of retinyl palmitate (RP; 54 IU), epigallo catechin gallate (EGCG; 120 μg) in either 50% (vol/vol) corn oil, or 50% (vol/vol) olive oil or 50% (vol/vol) grape seed oil, or 5% (vol/vol) squalene oil or 40% (vol/vol) mineral oil.

Figure 20:
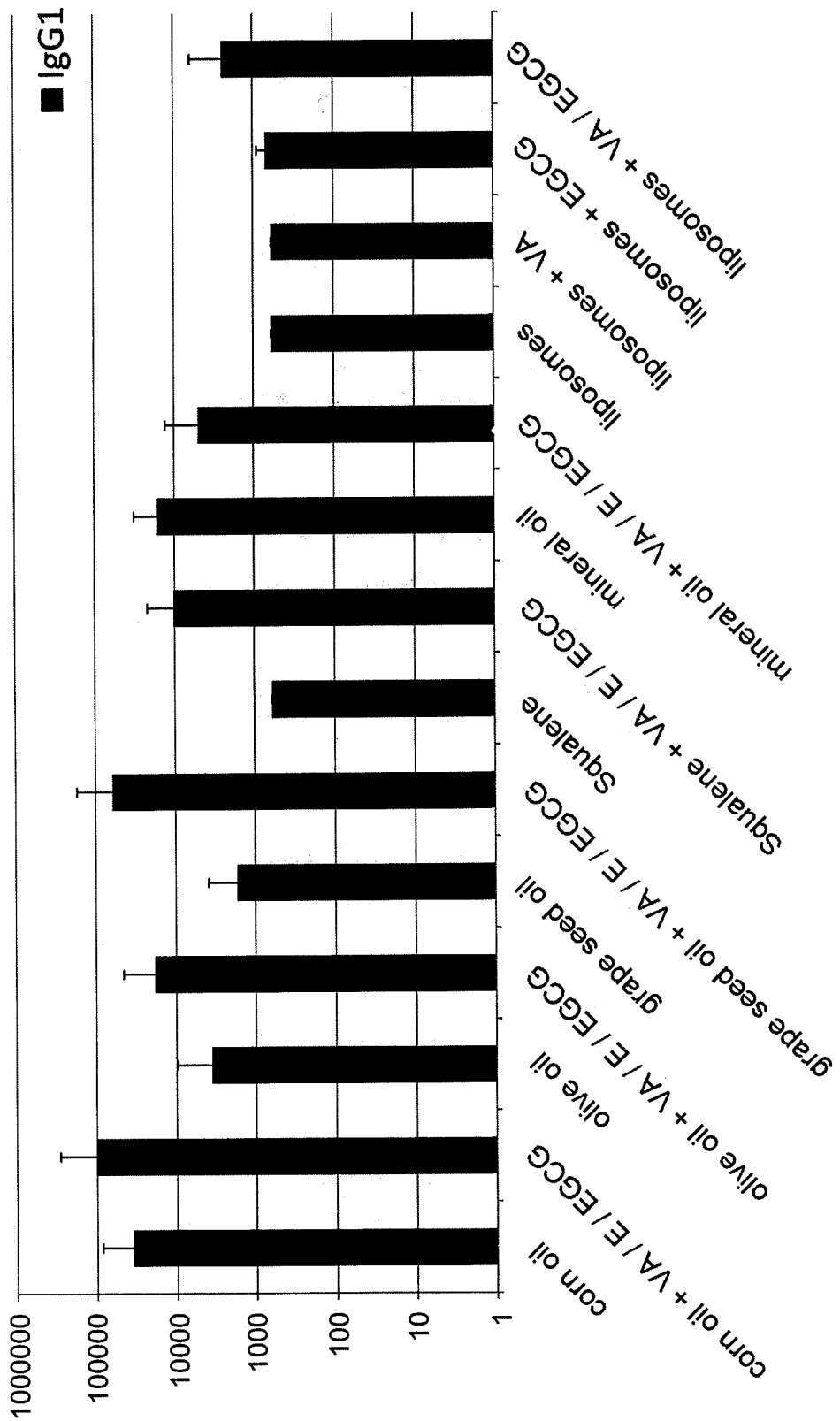
FIG. 20 is a bar graph showing synergistic immune-enhancement (serum IgG1 antibody titers on Y-axis) by VA, VE and EGCG with various oil based carriers.

The results of this study are shown in FIG. 20 which demonstrates that addition of VA, VE and EGCG to any of the oil carrier except mineral oil significantly enhanced serum IgG1 antigen-specific responses compared to vaccinations with each oil carrier alone.

Example 15: Antigen-Unspecific Enhancement of Serum IL-15 Cytokine Responses Following at 6 Hours Following a Single Intra-Muscular Injection with VA, EGCG, and MO Groups of 3 female BALB/C mice were injected once intra-muscularly with various formulations containing retinyl palmitate (RP; 54 IU), epigallo catechin gallate (EGCG; 120 μg), and/or 50% vol/vol mustard seed oil (MO). Sera were collected at six hours post injection and IL-15 cytokine response was measured by the multiplex Luminex assay.

Figure 21:
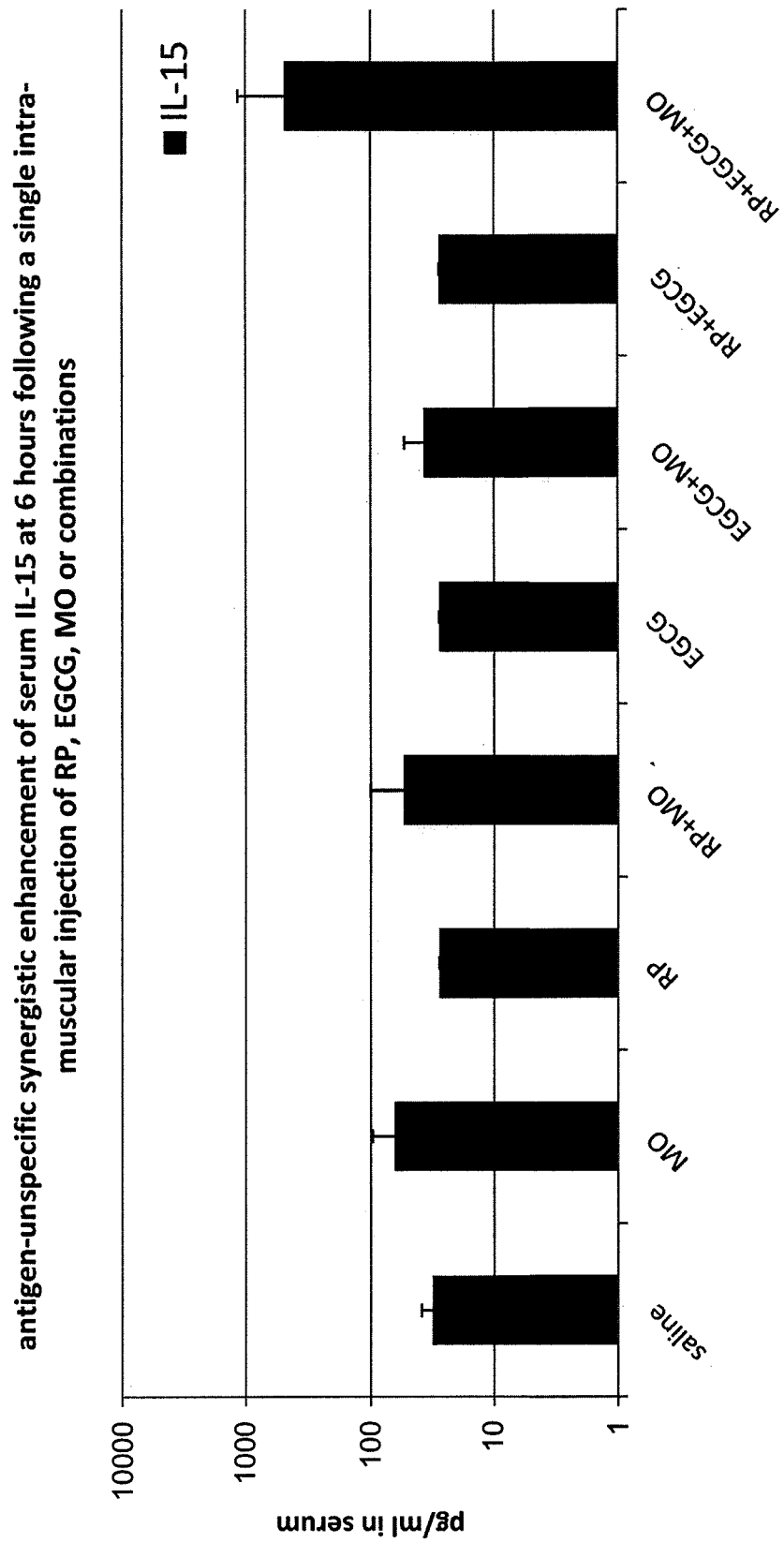
FIG. 21 is a bar graph showing antigen unspecific enhancement of serum IL-15 cytokine responses at 6 hours following a single IM injection with VA, EGCG and MO.

FIG. 21 shows that combinations of RP, EGCG, MO induce antigen-unspecific synergistic enhancement of serum IL-15 at 6 hours following a single intra-muscular injection.

Example 16: Antigen-Unspecific Enhancement of Serum IL-5 and IL-12p70 Cytokine Responses Following at 6 Hours Following a Single Intra-Muscular Injection with Vitamin E, Epigallo Catechin Gallate, Mustard Seed Oil (MO)

Groups of 3 female BALB/C mice were injected once intra-muscularly with various formulations containing alpha-tocopherol (vitamin E; 2 mg), epigallo catechin gallate (EGCG; 120 μg), and/or 50% vol/vol mustard seed oil (MO). Sera were collected at six hours post injection and IL-13 and IL-12p70 cytokine response was measured by the multiplex Luminex assay.

Figure 22:
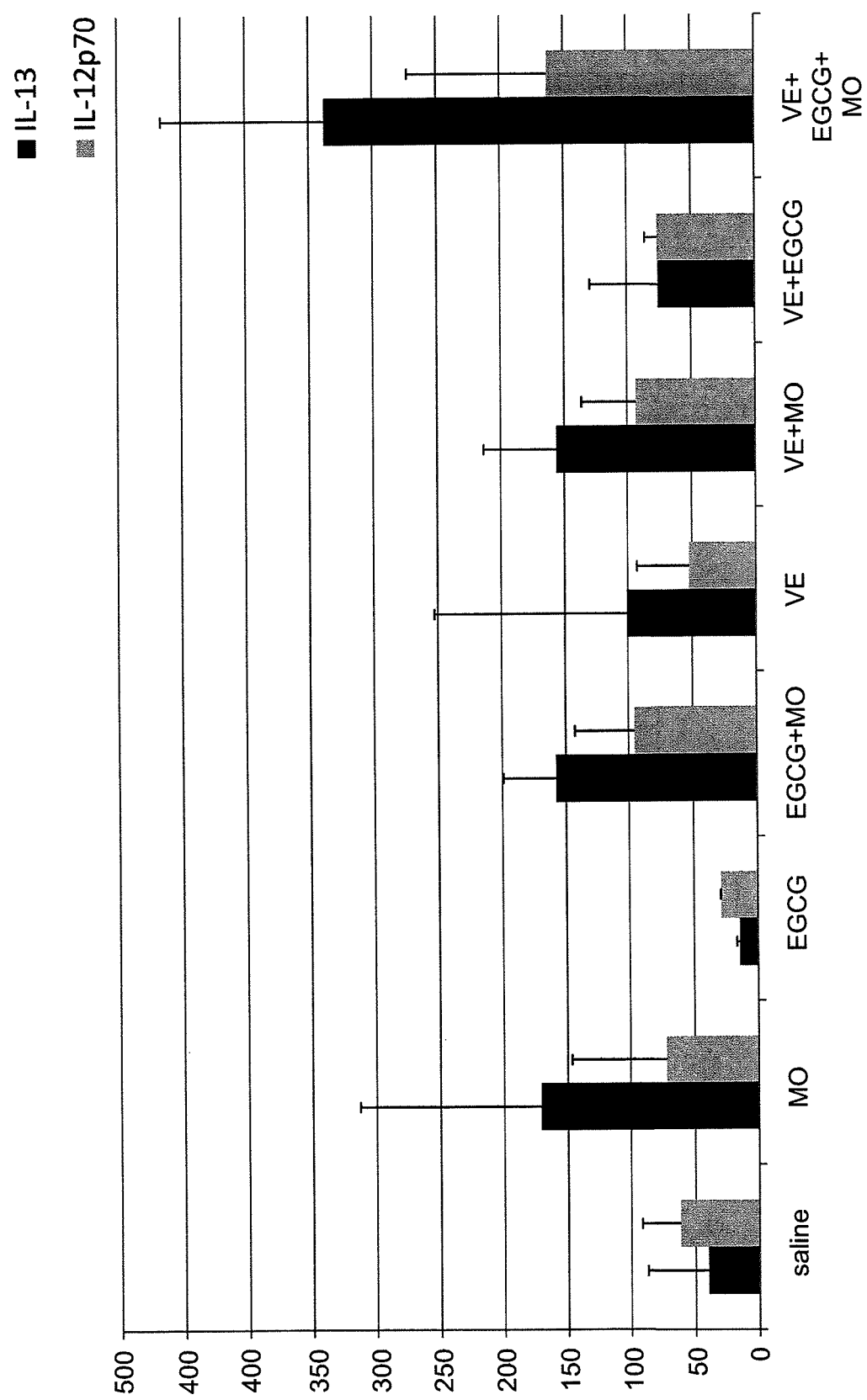
FIG. 22 is a bar graph showing antigen unspecific enhancement of serum IL-5 and IL-12p70 cytokine responses (pg/ml on Y-axis) at 6 hours following a single IM injection with VE, EGCG and MO.

FIG. 22 shows that combinations of Vitamin E, EGCG, MO induce antigen-unspecific synergistic enhancement of serum IL-13 and IL-12p70 at 6 hours following a single intra-muscular injection.

What is claimed is:

1. A composition consisting essentially of an emulsion, wherein the emulsion consists essentially of:
    (i) at least one vitamin selected from the group consisting of Vitamin A, Vitamin D, Vitamin E and a mixture thereof, wherein the vitamin A, if present, comprises an amount of about 0.1 to about 10 mg, and wherein the vitamin E, if present, comprises an amount of about 0.1 to about 40 mg;
    (ii) a pharmaceutically acceptable oil carrier selected from the group consisting of grape seed oil and squalene oil, wherein the grape seed oil, if present, comprises a volume of about 10% to about 50% v/v, and wherein the squalene oil, if present, comprises a volume of about 1% to about 5%; and
    (iii) at least one flavonoid, wherein the flavonoid comprises an amount of about 0.1 to about 2000 mg.

2. The composition according to claim 1, wherein the composition includes Vitamin A and Vitamin E.

3. The composition according to claim 1 or 2, wherein the flavonoid is a catechin.

4. The composition of claim 3, wherein the catechin is epigallo catechin gallate (EGCG).

5. A composition consisting essentially of an emulsion, wherein the emulsion consists essentially of:
    (i) at least one vitamin selected from the group consisting of Vitamin A, Vitamin D, Vitamin E and a mixture thereof, wherein the vitamin A, if present, comprises an amount of about 0.1 to about 10 mg, and wherein the vitamin E, if present, comprises an amount of about 0.1 to about 40 mg;
    (ii) a pharmaceutically acceptable oil carrier selected from the group consisting of grape seed oil and squalene oil, wherein the grape seed oil, if present, comprises a volume of about 10% to about 50% v/v, and wherein the squalene oil, if present, comprises a volume of about 1% to about 5%;
    (iii) at least one flavonoid, wherein the flavonoid comprises an amount of about 0.1 to about 2000 mg; and
    (iv) at least one antigen.

6. A composition consisting essentially of an emulsion, wherein the emulsion consists essentially of:
    (i) at least one vitamin selected from the group consisting of Vitamin A, Vitamin D, Vitamin E and a mixture thereof, wherein the vitamin A, if present, comprises an amount of about 0.1 to about 10 mg, and wherein the vitamin E, if present, comprises an amount of about 0.1 to about 40 mg;
    (ii) aluminum hydroxide, wherein the aluminum hydroxide comprises an amount of about 1% to about 50% w/v, and
    (iii) at least one flavonoid, wherein the flavonoid comprises an amount of about 0.1 to about 2000 mg.

7. The composition according to claim 6, wherein the flavonoid is a catechin.

8. The composition according to claim 7, wherein the catechin is epigallo catechin gallate (EGCG).

9. The composition according to claim 8, comprising from about 2.5% to 50% w/v aluminum hydroxide.

10. The composition according to claim 9, comprising 2.5% w/v aluminum hydroxide.

11. The composition according to claim 9, comprising 50% w/v aluminum hydroxide.

12. The composition according to claim 1, wherein the pharmaceutically acceptable oil is grape seed oil.

13. The composition according to claim 1, wherein the pharmaceutically acceptable oil is squalene oil.

14. The composition of claim 1, wherein the flavonoid is a tannin.

15. The composition of claim 6, wherein the flavonoid is a tannin.

16. A composition consisting essentially of an emulsion, wherein the emulsion consists essentially of:
    (i) at least one vitamin selected from the group consisting of Vitamin A, Vitamin D, Vitamin E and a mixture thereof, wherein the vitamin A, if present, comprises an amount of about 0.1 to about 10 mg, and wherein the vitamin E, if present, comprises an amount of about 0.1 to about 40 mg;
(ii) grape seed oil, wherein the grape seed oil comprises a volume of about 10% to about 50% v/v; and
(iii) at least one flavonoid, wherein the flavonoid comprises an amount of about 0.1 to about 2000 mg.

17. The composition according to claim 16, wherein the composition includes Vitamin A and Vitamin E.

18. The composition according to claim 16 or 17, wherein the flavonoid is a catechin or a tannin.

19. The composition of claim 18, wherein the flavonoid is epigallo catechin gallate (EGCG).

20. The composition of claim 19, wherein the flavonoid is a tannin.

21. The composition of claim 20, wherein the tannin is gallic acid.

22. A composition consisting essentially of an emulsion, wherein the emulsion consists essentially of:
(i) at least one vitamin selected from the group consisting of Vitamin A, Vitamin D, Vitamin E and a mixture thereof, wherein the vitamin A, if present, comprises an amount of about 0.1 to about 10 mg, and wherein the vitamin E, if present, comprises an amount of about 0.1 to about 40 mg;
(ii) grape seed oil, wherein the grape seed oil comprises a volume of about 10% to about 50% v/v;
(iii) at least one flavonoid, wherein the flavonoid comprises an amount of about 0.1 to about 2000 mg; and
(iv) at least one antigen.

23. The composition of claim 18, wherein the composition modulates an immune response in a subject when administered to the subject.

24. A composition consisting essentially of an emulsion, wherein the emulsion consists essentially of:
(i) at least one vitamin selected from the group consisting of Vitamin A, Vitamin D, Vitamin E and a mixture thereof, wherein the vitamin A, if present, comprises an amount of about 0.1 to about 10 mg, and wherein the vitamin E, if present, comprises an amount of about 0.1 to about 40 mg;
(ii) squalene oil, wherein the squalene oil comprises a volume of about 1% to about 5%; and
(iii) at least one flavonoid, wherein the flavonoid comprises an amount of about 0.1 to about 2000 mg.

25. The composition according to claim 24, wherein the composition includes Vitamin A and Vitamin E.

26. The composition according to claim 24 or 25, wherein the flavonoid is a catechin or a tannin.

27. The composition of claim 26, wherein the flavonoid is epigallo catechin gallate (EGCG).

28. The composition of claim 27, wherein the flavonoid is a tannin.

29. The composition of claim 28, wherein the tannin is gallic acid.

30. A composition consisting essentially of an emulsion, wherein the emulsion consists essentially of:
(i) at least one vitamin selected from the group consisting of Vitamin A, Vitamin D, Vitamin E and a mixture thereof, wherein the vitamin A, if present, comprises an amount of about 0.1 to about 10 mg, and wherein the vitamin E, if present, comprises an amount of about 0.1 to about 40 mg;
(ii) squalene oil, wherein the squalene oil comprises a volume of about 1% to about 5%;
(iii) at least one flavonoid, wherein the flavonoid comprises an amount of about 0.1 to about 2000 mg; and
(iv) an antigen.

31. The composition of claim 30, wherein the composition modulates an immune response in a subject when administered to the subject.

32. A composition consisting essentially of an emulsion, wherein the emulsion consists essentially of:
(i) at least one vitamin selected from the group consisting of Vitamin A, Vitamin D, Vitamin E and a mixture thereof, wherein the vitamin A, if present, comprises an amount of about 0.1 to about 10 mg, and wherein the vitamin E, if present, comprises an amount of about 0.1 to about 40 mg;
(ii) oleic acid, wherein the oleic acid comprises a volume of about 10% to about 50% v/v; and
(iii) at least one flavonoid, wherein the flavonoid comprises an amount of about 0.1 to about 2000 mg.

33. The composition according to claim 32, wherein the composition includes Vitamin A and Vitamin E.

34. The composition according to claim 32 or 33, wherein the flavonoid is a catechin or a tannin.

35. The composition of claim 34, wherein the flavonoid is epigallo catechin gallate (EGCG).

36. The composition of claim 35, wherein the flavonoid is a tannin.

37. The composition of claim 36, wherein the tannin is gallic acid.

38. A composition consisting essentially of an emulsion, wherein the emulsion consists essentially of:
(i) at least one vitamin selected from the group consisting of Vitamin A, Vitamin D, Vitamin E and a mixture thereof, wherein the vitamin A, if present, comprises an amount of about 0.1 to about 10 mg, and wherein the vitamin E, if present, comprises an amount of about 0.1 to about 40 mg;
(ii) oleic acid, wherein the oleic acid comprises a volume of about 10% to about 50% v/v;
(iii) at least one flavonoid, wherein the flavonoid comprises an amount of about 0.1 to about 2000 mg; and
(iv) an antigen.

39. The composition of claim 38, wherein the composition modulates an immune response in a subject when administered to the subject.

40. A composition consisting essentially of an emulsion, wherein the emulsion consists essentially of:
(i) at least one vitamin selected from the group consisting of Vitamin A, Vitamin D, Vitamin E and a mixture thereof, wherein the vitamin A, if present, comprises an amount of about 0.1 to about 10 mg, and wherein the vitamin E, if present, comprises an amount of about 0.1 to about 40 mg;
(ii) mustard seed oil, wherein the mustard seed oil comprises a volume of about 10% to about 50% v/v; and
(iii) at least one tannin, wherein the tannin comprises an amount of about 0.1 to about 2000 mg.

41. The composition according to claim 40, wherein the composition includes Vitamin A and Vitamin E.

42. The composition of claim 41, wherein the tannin is gallic acid.

43. A composition consisting essentially of an emulsion, wherein the emulsion consists essentially of:
(i) at least one vitamin selected from the group consisting of Vitamin A, Vitamin D, Vitamin E and a mixture thereof, wherein the vitamin A, if present, comprises an amount of about 0.1 to about 10 mg, and wherein the vitamin E, if present, comprises an amount of about 0.1 to about 40 mg;
  (ii) mustard seed oil, wherein the mustard seed oil comprises a volume of about 10% to about 50% v/v;
  (iii) at least one tannin, wherein the tannin comprises an amount of about 0.1 to about 2000 mg; and
  (iv) an antigen.

44. The composition of claim 43, wherein the composition modulates an immune response in a subject when administered to the subject.

45. The composition of any one of claim 1, 6, 16, 24, 32, or 40, wherein the emulsion is an oil-in-water emulsion.

46. The composition of claim 1 or 16, wherein the grape seed oil comprises a volume of about 50% v/v.

47. The composition of claim 1 or 24, wherein the squalene oil comprises a volume of about 5% v/v.

48. The composition of claim 32, wherein the oleic acid comprises a volume of about 40% v/v.

49. The composition of claim 40, wherein the mustard seed oil comprises a volume of about 50% v/v.

50. A composition consisting essentially of an emulsion, wherein the emulsion consists essentially of:
  (i) at least one vitamin selected from the group consisting of Vitamin A, Vitamin D, Vitamin E and a mixture thereof, wherein the vitamin A, if present, comprises an amount of about 0.1 to about 10 mg, and wherein the vitamin E, if present, comprises an amount of about 0.1 to about 40 mg;
  (ii) aluminum hydroxide, wherein the aluminum hydroxide comprises an amount of about 1% to about 50% w/v;
  (iii) at least one flavonoid, wherein the flavonoid comprises an amount of about 0.1 to about 2000 mg; and
  (iv) an antigen.

* * * * *